(12) United States Patent
Cosford et al.

(10) Patent No.: US 8,748,632 B2
(45) Date of Patent: Jun. 10, 2014

(54) POSITIVE ALLOSTERIC MODULATORS OF GROUP II MGLURS

(75) Inventors: Nicholas D. P. Cosford, La Jolla, CA (US); Dhanya Raveendra Panickar, La Jolla, CA (US); Shyama Sidique, La Jolla, CA (US); Svetlana Semenova, La Jolla, CA (US); Athinia Markou, La Jolla, CA (US)

(73) Assignees: Sanford-Burnham Medical Research Institute, La Jolla, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/051,798

(22) Filed: Mar. 18, 2011

(65) Prior Publication Data

US 2012/0071503 A1 Mar. 22, 2012

Related U.S. Application Data

(60) Provisional application No. 61/315,854, filed on Mar. 19, 2010.

(51) Int. Cl.
*C07D 209/46* (2006.01)
*A61K 31/4035* (2006.01)

(52) U.S. Cl.
CPC .......... *C07D 209/46* (2013.01); *A61K 31/4035* (2013.01)
USPC .......................................... 548/472; 514/416

(58) Field of Classification Search
CPC ........................... C07D 209/46; A61K 31/4035
USPC .......................................... 548/472; 514/416
See application file for complete search history.

(56) References Cited

U.S. PATENT DOCUMENTS

2008/0300260 A1 12/2008 Geneste et al.

FOREIGN PATENT DOCUMENTS

WO    WO 2006/057860 A1    6/2006

OTHER PUBLICATIONS

Kubinyi (3D QSAR in Drug Design: Ligand-Protein Interactions and Molecular Similarity, vol. 2-3, Springer, 1998, 800 pages). pp. 243-244 provided.*
Rodriguez et al. (Bioorganic & Medicinal Chemistry Letters 19 (2009) 3209-3213).*
Williams et al. (Bioorganic & Medicinal Chemistry Letters 19 (2009) 4967-4970).*
Govek et al. (Bioorganic & Medicinal Chemistry Letters 15 (2005) 4068-4072).*
Wermuth, The Practice of Medicinal Chemsitry, 2d ed. (2003), 768 pages. Chs. 9-10 provided.*
Gnerre et al. (Journal of Medicinal Chemistry (2000), 43(25), 4747-4758).*
Uno et al. (CAPLUS Abstract of: Chemical & Pharmaceutical Bulletin (1978), 26(2), 549-55).*
Hoarau et al. (CAPLUS Abstract of: Synthesis (2000), (5), 655-660).*
Bonnefous et al, "Biphenyl-indanones: allosteric potentiators of the metabotropic glutamate subtype 2 receptor", *Bioorg. Med. Chem. Lett.*, 15(19):4354-8 (2005).
Dhanya et al., "Design and synthesis of an orally active metabotropic glutamate receptor subtype-2 (mGluR2) positive allosteric modulator (PAM) that decreases cocaine self-administration in rats", *J. Med. Chem.*, 54(1):342-53 (2010).
Galici et al., "Biphenyl-indanone A, a positive allosteric modulator of the metabotropic glutamate receptor subtype 2, has antipsychotic- and anxiolytic-like effects in mice", *J. Pharmacol. Exp. Ther.*, 318(1):173-85 (2006).
International Search Report (ISR) from PCT/US2011/029100.

* cited by examiner

*Primary Examiner* — Robert Havlin
(74) *Attorney, Agent, or Firm* — DLA Piper LLP (US)

(57) ABSTRACT

The disclosure provides compounds and compositions, and methods of using these compounds and compositions, as positive allosteric modulators of the metabotropic glutamate subtype 2 (mGlu2) receptor, and for treating CNS disorders associated with the mGlu2 receptor including schizophrenia, anxiety, addiction, e.g. cocaine addiction, nicotine addiction, and the like.

17 Claims, No Drawings

POSITIVE ALLOSTERIC MODULATORS OF GROUP II MGLURS

STATEMENT OF GOVERNMENT SUPPORT

This invention was made in part with government support under Grant No. R01 DA023926 awarded by the National Institute on Drug Abuse (NIDA). The government has certain rights in the invention.

CROSS REFERENCE TO RELATED APPLICATIONS

This application claims the benefit of priority under 35 U.S.C. §119(e) to U.S. Provisional Application No. 61/315,854 filed on Mar. 19, 2010, the disclosure of which is hereby incorporated by reference in its entirety for all purposes.

BACKGROUND OF THE INVENTION

1. Field of the Invention

The disclosure generally relates to compounds and compositions, and methods of using these compounds and compositions, as positive allosteric modulators of the metabotropic glutamate receptor subtype 2 receptor (mGluR2), and mGluR3 (collectively Group II mGluRs), and for treating CNS disorders associated with Group II mGluRs (mGluII receptors) including schizophrenia, anxiety and addiction, e.g. cocaine addiction, nicotine addiction, alcohol addiction and the like.

2. Background Information

Glutamate receptors play a role in numerous neurological, neurodegenerative, psychiatric, and psychological disorders, and a variety of mammalian disease states are associated with aberrant activity of these receptors. Glutamate receptors have been classified as either "ionotropic" or "metabotropic". Ionotropic receptors are directly coupled to the opening of cation channels in the cell membranes of the neuron. Metabotropic receptors belong to the family of G-protein-coupled receptors and are coupled to systems that lead to enhanced phosphoinositide hydrolysis, activation of phospholipase D, increases or decreases in cAMP formation, and changes in ion channel function.

Metabotropic glutamate receptors (mGluRs) are divided into three groups based on amino acid sequence homology, transduction mechanism and binding selectivity: Group I, Group II and Group III. Group I includes metabotropic glutamate receptors 1 and 5 (mGluR1 and mGluR5), Group II includes metabotropic glutamate receptors 2 and 3 (mGluR2 and mGluR3), and Group III includes metabotropic glutamate receptors 4, 6, 7, and 8 (mGluR4, mGluR6, mGluR7 and mGluR8). Each mGluR type may be found in several subtypes. For example, subtypes of mGluR1 include mGluR1a, mGluR1b and mGluR1c.

Recently researchers have begun to elucidate physiological roles for each mGluR group. For example, Group II metabotropic glutamate receptors (mGluII), including mGlu2 and mGlu3 receptors, are inhibitory autoreceptors located primarily on glutamatergic afferents throughout the mammalian brain where they decrease excitatory glutamate transmission (Cartmell and Schoepp, J Neurochem 75:889-907, 2000). $GABA_B$ receptors, which share close structural and functional homology to mGluII receptors (Schoepp, J. Pharmacol. Exp. Ther., 299:12-20, 2001), also negatively regulate glutamate transmission. Recently, activation of mGluII and $GABA_B$ receptors was shown to decrease excitatory glutamate transmission in the ventral tegmental area (VTA) and nucleus accumbens (NAcc) (Bonci et al., Eur. J. Neurosci., 9:2359-2369, 1997; Xi et al., J. Pharmacol. Exp. Ther., 300:162-171, 2002; Erhardt et al., Naunyn Schmiedebergs Arch. Pharmacol., 365:173-180, 2002), suggesting that these receptors may regulate the activity of the brain's reward circuitry. Accordingly, LY314582 and CGP44532, agonists at mGluII and $GABA_B$ receptors respectively, were shown to elevate intracranial self-stimulation (ICSS) reward thresholds in drug-naive rats (Macey et al., Neuropharmacology, 40:676-685, 2001; Harrison et al., Psychopharmacology, 160:56-66, 2002), demonstrating that mGluII and $GABA_B$ receptors negatively regulate brain reward function.

Moreover, there is accumulating evidence that the function of mGluII and $GABA_B$ receptors increases during the development of drug dependence. For example, prolonged morphine, cocaine or amphetamine treatment increased inhibitory regulation of glutamate transmission by mGluII and $GABA_B$ receptors located in the VTA and NAcc (Manzoni and Williams, J. Neurosci., 19:6629-6636, 1999; Xi et al., Soc. Neurosci., Abstr 27: 2596, 2001; Giorgetti et al., Neuroscience, 109:585-595, 2002).

Attempts at elucidating the physiological roles of Group II mGluRs suggest that activation of these receptors elicits neuronal excitation. Evidence indicates that this excitation is due to direct activation of postsynaptic mGluRs, but it also has been suggested that activation of presynaptic mGluRs occurs, resulting in increased neurotransmitter release (Baskys, Trends Pharmacol. Sci. 5:92, 1992, Schoepp, Neurochem. Int. 24:439, 1994, Pin et al., Neuro-pharmacology 34:1, 1995.) Thus, it has been proposed that antagonists for the Group II mGluRs may be useful in treating neurological disorders such as senile dementia, Parkinson's disease, Alzheimer's disease, Huntington's Chorea, pain, epilepsy, and head trauma.

However, less is known about the potential therapeutic benefits that may be realized as a result of simultaneous antagonism of mGluRs belonging to different groups. Furthermore, little is known about whether antagonists of mGluRs are useful for treating disorders such as substance abuse such as cocaine addiction, depression and schizophrenia. The disclosure addresses these issues and further provides related advantages

SUMMARY OF THE INVENTION

The disclosure provides compounds and compositions, and methods of using these compounds and compositions, as positive allosteric modulators of Group II metabotropic glutamate receptors (mGluII receptors). The disclosed compounds and compositions are useful for treating CNS disorders associated with mGluII receptors including schizophrenia, anxiety, addiction, e.g. cocaine addiction, nicotine addiction, and the like.

Thus, in one embodiment the disclosure provides compound of Formula I

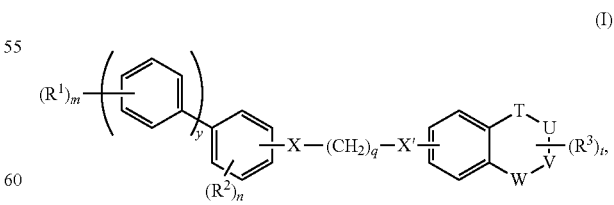

or a pharmaceutically acceptable salt or solvate thereof, wherein:

X and X' are each independently absent or are each independently selected from O, S, and $NR^4$;

y is independently an integer selected from 0 and 1;

q is independently an integer selected from 0, 1, 2, 3, 4, 5 and 6;

m, n, and t are each independently an integer selected from 0, 1, 2, 3, and 4;

T, U, V and W are each independently absent, or are each independently selected from C=O, CHR$^3$, O, S, SO, SO$_2$, and NR$^3$, or T and U, U and V, or V and W each independently form —CR$^3$=CR$^{3'}$— or —CR$^3$=N—, wherein T, U, V and W, together with the phenyl group to which T and W are attached, form a 5 or 6 membered ring;

R$^1$ and R$^2$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl, —(CH$_2$)$_j$OR$^5$, —(CH$_2$)$_j$C(Z)R$^5$, —(CH$_2$)$_j$C(O)OR$^5$, —(CH$_2$)$_j$NR$^6$R$^7$, —(CH$_2$)$_j$C(O)NR$^6$R$^7$, —(CH$_2$)$_j$OC(O)NR$^6$R$^7$, —(CH$_2$)$_j$NR$^8$C(O)R$^5$, —(CH$_2$)$_j$NR$^8$C(O)OR$^5$, —(CH$_2$)$_j$NR$^8$C(O)NR$^6$R$^7$, —(CH$_2$)$_j$S(O)$_k$R$^9$, —(CH$_2$)$_j$NR$^8$S(O)$_2$R$^9$, and —(CH$_2$)$_j$S(O)$_2$NR$^6$R$^7$; wherein each j is independently an integer selected from 0, 1, 2, 3, 4, 5 and 6; and each k is independently an integer selected from 0, 1 and 2; and Z is independently selected from O, S and NR$^{10}$;

R$^3$ and R$^{3'}$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl;

R$^4$ is independently selected from hydrogen and substituted or unsubstituted alkyl;

R$^5$, R$^6$, R$^7$, R$^8$, and R$^9$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl, or R$^5$, R$^8$, and R$^9$ are as described and R$^6$ and R$^7$, together with the nitrogen to which they are attached, form substituted or unsubstituted 3- to 7-membered heterocycloalkyl, or substituted or unsubstituted 5-membered heteroaryl;

R$^{10}$ is independently selected from hydrogen and substituted or unsubstituted alkyl; and wherein each of R$^1$, R$^2$, R$^3$, R$^4$, R$^5$, R$^6$, R$^7$, R$^8$, R$^9$, and R$^{10}$ is optionally independently substituted with 1 to 3 groups, each group independently selected from hydrogen, halogen, cyano, amino, aminomonoalkyl, aminodialkyl, nitro, hydroxyl, alkyl, perfluoroalkyl, alkoxy, alkenyl, alkynyl, cycloalkyl, heteroalkyl, heterocycloalkyl, aryl, heteroaryl, alkylaryl, and heteroalkylaryl.

DETAILED DESCRIPTION OF THE INVENTION

Definitions

Abbreviations used herein have their conventional meaning within the chemical and biological arts. Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or cyclic hydrocarbon radical, or combinations thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, N-propyl, isopropyl, N-butyl, sec-butyl, tert-butyl, isobutyl, cyclobutyl, pentyl, cyclopentyl, hexyl, cyclohexyl, (cyclohexyl)methyl, cyclopropylmethyl, homologs and isomers of, for example, N-pentyl, N-hexyl, N-heptyl, N-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —CH$_2$CH$_2$CH$_2$CH$_2$—, —CH$_2$CH=CHCH$_2$—, —CH$_2$C=CCH$_2$—, —CH$_2$CH$_2$CH(CH$_2$CH$_2$CH$_3$)CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

As used herein, the terms "alkyl" and "alkylene" are interchangeable depending on the placement of the "alkyl" or "alkylene" group within the molecule.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$ and —CN. Up to two or three heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'-represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. As used herein, the terms "heteroalkyl" and "heteroalkylene" are interchangeable depending on the placement of the "heteroalkyl" or "heteroalkylene" group within the molecule.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, when the heteroatom is nitrogen, it can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively. As used herein, the terms "cycloalkyl" and "cycloalkylene" are interchangeable depending on the placement of the "cycloalkyl" or "cycloalkylene" group within the molecule. As used herein, the terms "heterocycloalkyl" and "heterocycloalkylene" are interchangeable depending on the placement of the "heterocycloalkyl" or "heterocycloalkylene" group within the molecule.

The terms "halo" or "halogen," by themselves or as part of another substituent, mean, unless otherwise stated, a fluorine, chlorine, bromine, or iodine atom. Additionally, terms such as "haloalkyl" and "perfluoroalkyl" are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. As used herein, the terms "haloalkyl" and "haloalkylene" are interchangeable depending on the placement of the "haloalkyl" or "haloalkylene" group within the molecule.

The term "aryl" means, unless otherwise stated, a polyunsaturated, aromatic, hydrocarbon substituent which can be a single ring or multiple rings, which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. For example, pyridine N-oxide moieties are included within the description of "heteroaryl." A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively. As used herein, the terms "aryl" and "arylene" are interchangeable depending on the placement of the "aryl" and "arylene" group within the molecule. As used herein, the terms "heteroaryl" and "heteroarylene" are interchangeable depending on the placement of the "heteroaryl" and "heteroarylene" group within the molecule.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover aryls substituted with one or more halogens.

Where a heteroalkyl, heterocycloalkyl, or heteroaryl includes a specific number of members (e.g., "3 to 7 membered"), the term "member" referrers to a carbon or heteroatom.

The term "oxo" as used herein means an oxygen that is double bonded to a carbon atom.

Each of the above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R'— C(O)NR"R"', —OC(O)NR'R", —NR"C(O)R", —NR'—C(O)NR"R"', —NR'C(O)OR', —NR"—C(NR"'R"")=NR"", —S(O)R', —S(O)$_2$R', —S(O)$_2$NR'R", —NR'SO$_2$R", —CN and —NO$_2$ in a number ranging from zero to (2 m'+1), where m$^1$ is the total number of carbon atoms in such radical. R', R", R"' and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R$^1$, R", R"' and R"" groups when more than one of these groups is present. When R$^1$ and R" are attached to the same nitrogen atom, they can be combined with the nitrogen atom to form a A-, 5-, 6-, or 7-membered ring. For example, —NR$^1$R" is meant to include, but not be limited to, 1-pyrrolidinyl and A-morpholinyl. From the above discussion of substituents, one of skill in the art will understand that the term "alkyl" is meant to include groups including carbon atoms bound to groups other than hydrogen groups, such as haloalkyl and perfluoroalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R'', —SR', -halogen, —SiR'R''R''', —OC(O)R', —C(O)R', —CO$_2$R', —C(O)NR'R'', —OC(O)NR'R'', —NR'C(O)R'', —NR'—C(O)NR''R''', —NR'C(O)OR'', —NRC(NR'R''R''')=NR'''', —NRC(NR'R'')=NR''', —S(O)R', —S(O)$_2$R', —S(O)$_2$NR'R'', —NR'SO$_2$R'', —CN and —NO$_2$, in a number ranging from zero to the total number of open valences on aromatic ring system; and where R', R'', R''' and R'''' are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R'', R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CR'R''—, —O—, —NR''—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CR'R'')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R', R'', and R''' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R'', wherein R' and R'' are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from at least the following moieties: (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The neutral forms of the compounds are regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by the disclosure.

Certain compounds of the disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the disclosure.

The compounds of the disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the disclosure, whether radioactive or not, are encompassed within the scope of the disclosure.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, mono-hydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science, 66:1-19 (1977)). Certain specific compounds of the disclosure contain both basic and acidic functionalities that allow the compounds to be converted into either base or acid addition salts.

In addition to salt forms, the disclosure provides compounds, which are in a prodrug form. Prodrugs of the compounds described herein are those compounds that readily undergo chemical changes under physiological conditions to provide the compounds of the disclosure. Additionally, prodrugs can be converted to the compounds of the disclosure by chemical or biochemical methods in an ex vivo environment. For example, prodrugs can be slowly converted to the compounds of the disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The symbol $>\!\!\sim\!\!w\!-$ denotes the point of attachment of a moiety to the remainder of the molecule.

The disclosure provides compounds and compositions, and methods of using these compounds and compositions, as positive allosteric modulators of the metabotropic gluatmate receptor subtype 2 (mGluR2) receptor. The disclosed compounds and compositions are useful for treating CNS disorders associated with the mGluR2 receptor including schizophrenia, anxiety, addiction, e.g. cocaine addiction, nicotine addiction, and the like.

Positive Allosteric Modulators of mGluII receptors

In one aspect the disclosure provides a compound of Formula IA:

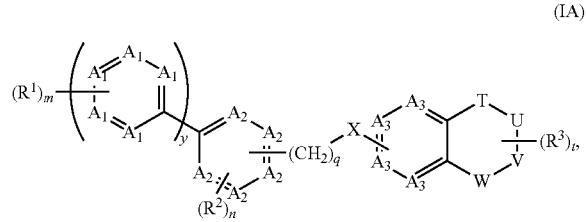

or a pharmaceutically acceptable salt or solvent thereof, wherein:

each $A_1$ is independently —$CR^1$= or —N=;
each $A_2$ is independently —$CR^2$=, —(C=)— or —N=;
each $A_3$ is independently —$CR^3$=, —(C=)— or —N=;
X is independently O, S, or $NR^4$;
m, n, and t are each independently an integer from 0, 1, 2, 3, to 4;
y is independently an integer selected from 0 and 1;
q is independently an integer selected from 0, 1, 2, 3, 4, 5 to 6;
T, U, V and W are each independently absent, or are each independently CO, $CH_2$, $CHR^3$, O, S, SO, $SO_2$, NH, $NR^3$, or $NR^5$, or T and U, U and V, or V and W form —$CR_3$=$CR_3$— or —$CR_3$=N—, wherein T, U, V and W, together with the phenyl group to which T and W are attached, form a 5 or 6 membered ring;
$R^1$ and $R^2$ are each independently hydrogen, halogen, cyano, nitro, hydroxyl, substituted or unsubstituted alkyl, substituted or unsubstituted alkene, substituted or unsubstituted alkyne, substituted or unsubstituted haloalkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl, —(CH$_2$)$_j$C(=Z)R$^6$, —(CH$_2$)$_j$OR$^6$, —(CH$_2$)$_j$C(O)R$^6$, —(CH$_2$)$_j$C(O)OR$^6$, —(CH$_2$)$_j$NR$^7$R$^8$, —(CH$_2$)$_j$C(O)NR$^7$R$^8$, —(CH$_2$)$_j$OC(O)NR$^7$R$^8$, —(CH$_2$)$_j$NR$^9$C(O)R$^6$, —(CH$_2$)$_j$NR$^9$C(O)OR$^6$, —(CH$_2$)$_j$NR$^9$C(O)NR$^7$R$^8$, —(CH$_2$)$_j$S(O)$_k$R$^{10}$, —(CH$_2$)$_j$NR$^9$S(O)$_2$R$^{10}$, or —(CH$_2$)$_j$S(O)$_2$NR$^7$R$^8$; wherein each j is independently an integer from 0, 1, 2, 3, 4, 5 to 6; and k is independently an integer from 0, 1 to 2; and Z is O, S or NR$^{11}$;

R$^3$ is independently hydrogen, halogen, cyano, nitro, hydroxyl, substituted or unsubstituted alkyl, substituted or unsubstituted alkene, substituted or unsubstituted alkyne, substituted or unsubstituted haloalkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl;

R$^4$ is independently hydrogen or substituted or unsubstituted alkyl;

R$^5$ is independently hydrogen, hydroxyl, substituted or unsubstituted alkyl, substituted or unsubstituted alkene, substituted or unsubstituted alkyne, substituted or unsubstituted haloalkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl;

R$^6$ is independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$, R$^8$, R$^9$ and R$^{10}$ are each independently hydrogen, substituted or unsubstituted alkyl, substituted or unsubstituted alkyl-NR$^{12}$R$^{13}$, substituted or unsubstituted alkyl-CONR$^{12}$R$^{13}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or R$^7$ and R$^8$, together with the nitrogen to which they are attached, form substituted or unsubstituted 3- to 7-membered heterocycloalkyl, or substituted or unsubstituted 5-membered heteroaryl;

R$^{11}$ is independently hydrogen, substituted or unsubstituted alkyl, substituted or unsubstituted haloalkyl, substituted or unsubstituted heteroalkyl, substituted or unsubstituted aryl, substituted or unsubstituted heteroaryl, substituted or unsubstituted heterocycloalkyl, or substituted or unsubstituted cycloalkyl;

R$^{12}$ and R$^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or R$^{12}$ and R$^{13}$ are joined together with the nitrogen to which they are attached, to form substituted or unsubstituted 3- to 7-membered heterocycloalkyl, or substituted or unsubstituted 5-membered heteroaryl; wherein any of the groups listed for R$^1$, R$^2$, R$^3$, R$^4$, R$^5$, R$^6$, R$^7$, R$^8$, R$^9$, R$^{10}$, R$^{11}$, R$^{12}$ and R$^{13}$ are each optionally independently substituted with 1 to 3 groups, each group independently selected from halogen, hydroxyl, amino, aminomonoalkyl, aminodialkyl, cyano, nitro, haloalkyl, alkyl, heteroalkyl, oxo, —O—alkyl, and —S-alkyl.

In another aspect the disclosure provides compounds of Formula IA, wherein T, U, V and W, together with the phenyl group to which T and W are attached, form a 5 membered ring including:

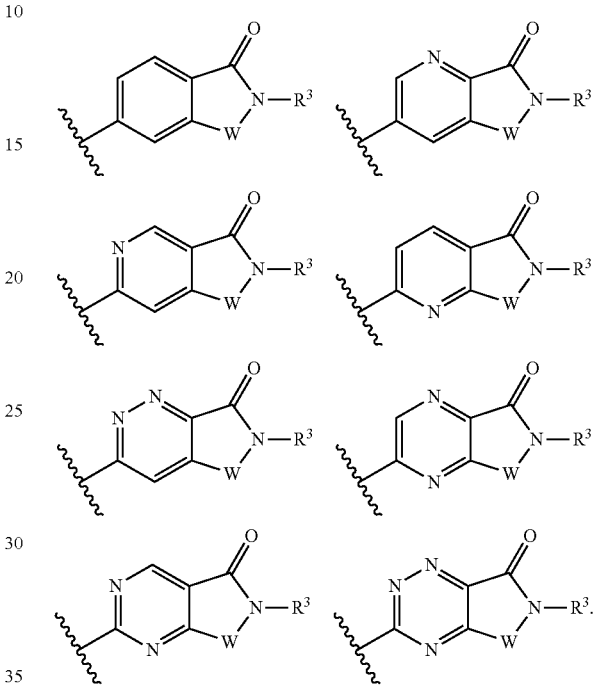

In another aspect the disclosure provides compounds of Formula IA, wherein T, U, V and W, together with the phenyl group to which T and W are attached, form a 6 membered ring including:

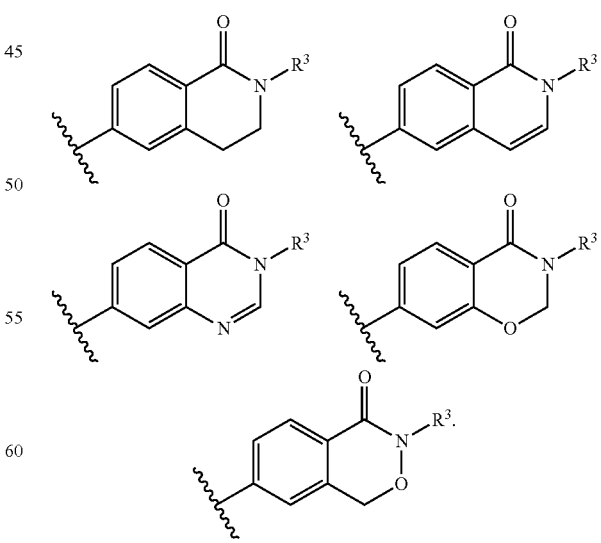

In another aspect the disclosure provides a compound of Formula I:

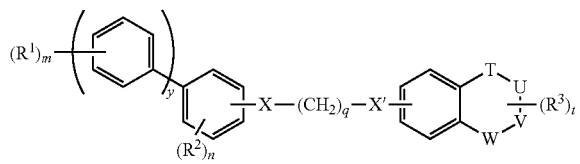
(I)

or a pharmaceutically acceptable salt or solvate thereof, wherein:

X and X' are each independently absent or are each independently selected from O, S, and NR$^4$;

y is independently an integer selected from 0 and 1;

q is independently an integer selected from 0, 1, 2, 3, 4, 5 and 6;

m, n, and t are each independently an integer selected from 0, 1, 2, 3, and 4;

T, U, V and W are each independently absent, or are each independently selected from C=O, CHR$^3$, O, S, SO, SO$_2$, and NR$^3$, or T and U, U and V, or V and W each independently form —CR$^3$=CR$^{3'}$— or —CR$^3$=N—, wherein T, U, V and W, together with the phenyl group to which T and W are attached, form a 5 or 6 membered ring;

R$^1$ and R$^2$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl, —(CH$_2$)$_j$OR$^5$, —(CH$_2$)$_j$C(Z)R$^5$, —(CH$_2$)$_j$C(O)OR$^5$, —(CH$_2$)$_j$NR$^6$R$^7$, —(CH$_2$)$_j$C(O)NR$^6$R$^7$, —(CH$_2$)$_j$OC(O)NR$^6$R$^7$, —(CH$_2$)$_j$NR$^8$C(O)R$^5$, —(CH$_2$)$_j$NR$^8$C(O)OR$^5$, —(CH$_2$)$_j$NR$^8$C(O)NR$^6$R$^7$, —(CH$_2$)$_j$S(O)$_k$R$^9$, —(CH$_2$)$_j$NR$^8$S(O)$_2$R$^9$, and —(CH$_2$)$_j$S(O)$_2$NR$^6$R$^7$; wherein each j is independently an integer selected from 0, 1, 2, 3, 4, 5 and 6; and each k is independently an integer selected from 0, 1 and 2; and Z is independently selected from O, S and NR$^{10}$;

R$^3$ and R$^{3'}$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl;

R$^4$ is independently selected from hydrogen and substituted or unsubstituted alkyl;

R$^5$, R$^6$, R$^7$, R$^8$, and R$^9$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkylaryl, substituted or unsubstituted heteroalkylaryl, or R$^5$, R$^8$, and R$^9$ are as described above and R$^6$ and R$^7$, together with the nitrogen to which they are attached, form substituted or unsubstituted 3- to 7-membered heterocycloalkyl, or substituted or unsubstituted 5-membered heteroaryl;

R$^{10}$ is independently selected from hydrogen and substituted or unsubstituted alkyl; and wherein each of R$^1$, R$^2$, R$^3$, R$^4$, R$^5$, R$^6$, R$^7$, R$^8$, R$^9$, and R$^{10}$ is optionally independently substituted with 1 to 3 groups, each group independently selected from hydrogen, halogen, cyano, amino, aminomonoalkyl, aminodialkyl, nitro, hydroxyl, alkyl, perfluoroalkyl, alkoxy, alkenyl, alkynyl, cycloalkyl, heteroalkyl, heterocycloalkyl, aryl, heteroaryl, alkylaryl, and heteroalkylaryl.

In another aspect the disclosure provides a compound of Formula I, wherein:

X is independently absent and X' is independently O;

y is independently 1;

q is independently 1;

T, U, V and W are each independently selected from CO, CHR$^3$, O, S, SO, SO$_2$, and NR$^3$, wherein T, U, V and W, together with the phenyl group to which T and W are attached, form a 5 membered ring;

R$^1$ and R$^2$ are each independently selected from hydrogen, halogen, cyano, nitro, hydroxyl, substituted or unsubstituted alkyl, perfluoroalkyl, —(CH$_2$)$_j$C(=O)R$^5$, —(CH$_2$)$_j$OR$^5$, —(CH$_2$)$_j$C(O)R$^5$, —(CH$_2$)$_j$C(O)OR$^5$, and (CH$_2$)$_j$(O)NR$^6$R$^7$, wherein each j is independently an integer selected from 0, 1, 2, and 3;

R$^3$ and R$^{3'}$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted aryl, and substituted or unsubstituted alkylaryl; and R$^5$, R$^6$, and R$^7$ are each independently selected from hydrogen and substituted or unsubstituted alkyl.

In another aspect the disclosure provides a compound of Formula I, wherein T, U, V and W, together with the phenyl group to which T and W are attached, form a 5 membered ring including:

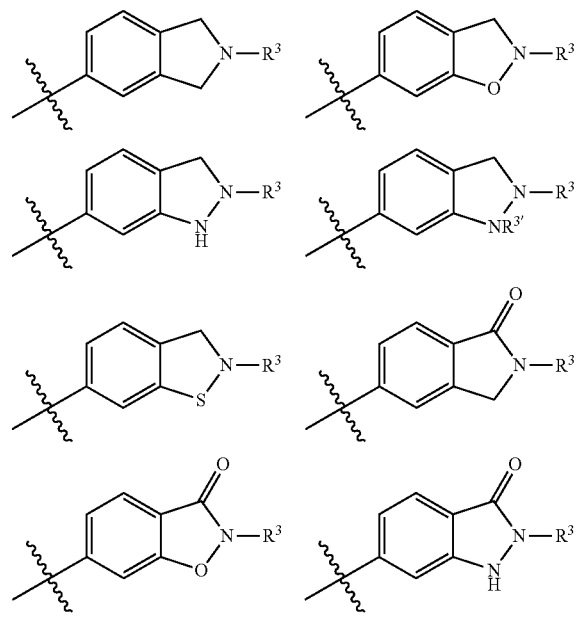

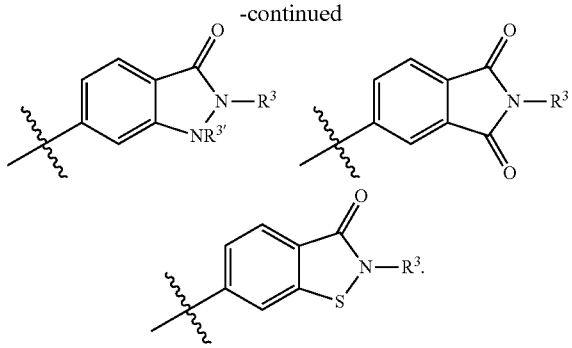

In another aspect the disclosure provides a compound of Formula I, wherein:

X is independently absent and X' is independently O;

y is independently 1;

q is independently 1;

T, U, V and W are each independently selected from CO, $CHR^3$, O, S, SO, $SO_2$, and $NR^3$, wherein T, U, V and W, together with the phenyl group to which T and W are attached, form a 6 membered ring;

$R^1$ and $R^2$ are each independently selected from hydrogen, halogen, cyano, nitro, hydroxyl, substituted or unsubstituted alkyl, perfluoroalkyl, —$(CH_2)_jC(=O)R^5$, —$(CH_2)_jOR^5$, —$(CH_2)_jC(O)R^5$, —$(CH_2)_jC(O)OR^5$, and $(CH_2)_jC(O)NR^6R^7$, wherein each j is independently an integer selected from 0, 1, 2, and 3;

$R^3$ and $R^{3'}$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted aryl, and substituted or unsubstituted alkylaryl; and $R^5$, $R^6$, and $R^7$ are each independently selected from hydrogen and substituted or unsubstituted alkyl.

In another aspect the disclosure provides a compound of Formula I, wherein T, U, V and W, together with the phenyl group to which T and W are attached, form a 6 membered ring including:

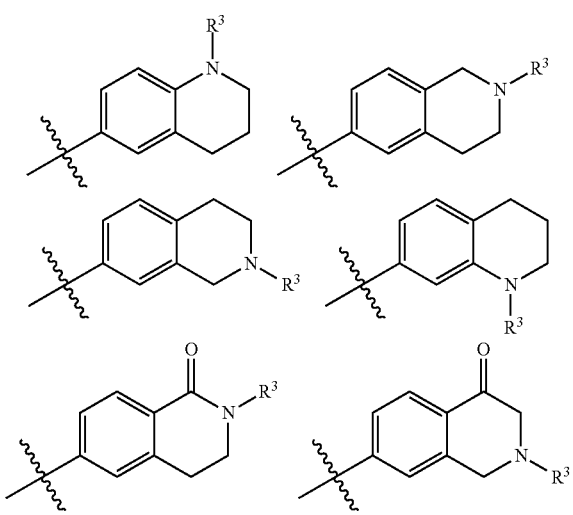

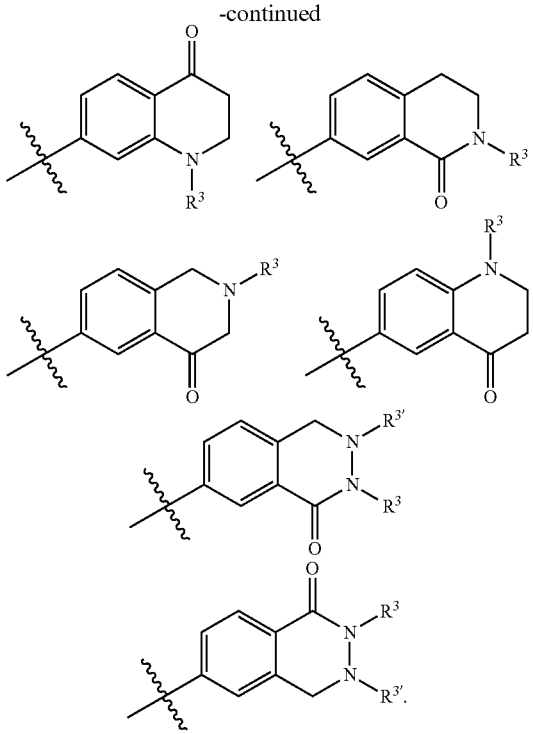

In another aspect the disclosure provides a compound of Formula I, wherein the compound of Formula I has Formula II:

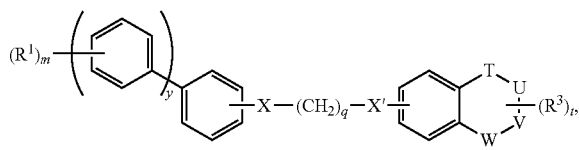

(II)

wherein:

X and X' are each independently absent or are each independently selected from O, S, and $NR^4$;

y is independently an integer selected from 0 and 1;

q is independently an integer selected from 0, 1, 2, 3, 4, 5 and 6;

m and t are each independently an integer selected from 0, 1, 2, 3, and 4;

T, U, V and W are each independently selected from CO, $CHR^3$, O, S, SO, $SO_2$, and $NR^3$, wherein T, U, V and W, together with the phenyl group to which T and W are attached, form a 5 or a 6 membered ring;

$R^1$ and $R^2$ are each independently selected from hydrogen, halogen, cyano, nitro, hydroxyl, substituted or unsubstituted alkyl, perfluoroalkyl, —$(CH_2)_jC(=O)R^5$, —$(CH_2)_jOR^5$, —$(CH_2)_jC(O)R^5$, —$(CH_2)_jC(O)OR^5$, and $(CH_2)_jC(O)NR^6R^7$, wherein each j is independently an integer selected from 0, 1, 2, and 3;

$R^3$ and $R^{3'}$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted aryl, and substituted or unsubstituted alkylaryl; and $R^5$, $R^6$, and $R^7$ are each independently selected from hydrogen and substituted or unsubstituted alkyl.

In another aspect the disclosure provides a compound of Formula II, wherein:
X is independently absent and X' is independently O;
y is independently 1;
q is independently 1;
T, U, V and W are each independently absent, or are each independently selected from C=O, $CHR^3$, O, S, SO, $SO_2$, and $NR^3$, wherein T, U, V and W, together with the phenyl group to which T and W are attached, form a 5 membered ring;
$R^1$ is independently selected from hydrogen, halogen, cyano, nitro, hydroxyl, substituted or unsubstituted alkyl, perfluoroalkyl, —C(=O)$R^5$, —$OR^5$, —C(O)$R^5$, —C(O)$OR^5$, and —C(O)$NR^6R^7$, wherein each j is independently an integer selected from 0, 1, 2, and 3;
$R^3$ and $R^{3'}$ are each independently selected from hydrogen, halogen, substituted or unsubstituted alkyl, perfluoroalkyl, substituted or unsubstituted cycloalkyl, substituted or unsubstituted aryl, and substituted or unsubstituted alkylaryl.

In another aspect the disclosure provides a compound of Formula II, wherein:
X is independently absent and X' is independently O;
y is independently 1;
q is independently 1;
T, U, V and W are each independently absent, or are each independently selected from C=O, $CHR^3$, O, S, SO, $SO_2$, and $NR^3$, wherein T, U, V and W, together with the phenyl group to which T and W are attached, form a 6 membered ring;
$R^1$ is independently selected from hydrogen, halogen, cyano, nitro, hydroxyl, substituted or unsubstituted alkyl, perfluoroalkyl, —C(=O)$R^5$, —$OR^5$, —C(O)$R^5$, —C(O)$OR^5$, and —C(O)$NR^6R^7$, wherein each j is independently an integer selected from 0, 1, 2, and 3;
$R^3$ and $R^{3'}$ are each independently selected from hydrogen, halogen, substituted or unsubstituted alkyl, perfluoroalkyl, substituted or unsubstituted cycloalkyl, substituted or unsubstituted aryl, and substituted or unsubstituted alkylaryl.

In another aspect the disclosure provides a compound of Formula I, wherein the compound of Formula I has Formula III:

(III)

$(R^1)_m$—[phenyl]$_y$—X—$(CH_2)_q$—X'—[phenyl ring with C(=O)N($R^3$)-V-W-($R^3$)$_t$]

wherein:
X and X' are each independently absent or are each independently selected from O, S, and $NR^4$;
y is independently an integer selected from 0 and 1;
q is independently an integer selected from 0, 1, 2, 3, 4, 5 and 6;
m and t are each independently an integer selected from 0, 1, 2, 3, and 4;
V and W are each independently absent, or are each independently selected from C=O, $CHR^3$, O, S, SO, $SO_2$, and $NR^3$, wherein $CONR^3$ and W, together with the phenyl group to which $CONR^3$ and W are attached, form a 5 or 6 membered ring;

$R^1$ and $R^2$ are each independently selected from hydrogen, halogen, cyano, nitro, hydroxyl, substituted or unsubstituted alkyl, perfluoroalkyl, —$(CH_2)_jC(=O)R^5$, —$(CH_2)_jOR^5$, —$(CH_2)_jC(O)R^5$, —$(CH_2)_jC(O)OR^5$, and —$(CH_2)_jC(O)NR^6R^7$, wherein each j is independently an integer selected from 0, 1, 2, and 3;
$R^3$ and $R^{3'}$ are each independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted aryl, and substituted or unsubstituted alkylaryl; and
$R^5$, $R^6$, and $R^7$ are each independently selected from hydrogen and substituted or unsubstituted alkyl.

In another aspect the disclosure provides a compound of Formula III, wherein:
X is independently absent and X' is independently O;
y is independently 1;
q is independently 1;
V and W are each independently absent, or are each independently selected from C=O, $CHR^3$, O, S, SO, $SO_2$, and $NR^3$, wherein $CONR^3$ and W, together with the phenyl group to which $CONR^3$ and W are attached, form a 5 membered ring;
$R^1$ is independently selected from hydrogen, halogen, cyano, nitro, hydroxyl, substituted or unsubstituted alkyl, perfluoroalkyl, —C(=O)$R^5$, —$OR^5$, —C(O)$R^5$, —C(O)$OR^5$, and —C(O)$NR^6R^7$, wherein each j is independently an integer selected from 0, 1, 2, and 3;
$R^3$ and $R^{3'}$ are each independently selected from hydrogen, halogen, substituted or unsubstituted alkyl, perfluoroalkyl, substituted or unsubstituted cycloalkyl, substituted or unsubstituted aryl, and substituted or unsubstituted alkylaryl.

In another aspect the disclosure provides a compound of Formula III, wherein:
X is independently absent and X' is independently O;
y is independently 1;
q is independently 1;
V and W are each independently absent, or are each independently selected from C=O, $CHR^3$, O, S, SO, $SO_2$, and $NR^3$, wherein $CONR^3$ and W, together with the phenyl group to which $CONR^3$ and W are attached, form a 6 membered ring;
$R^1$ is independently selected from hydrogen, halogen, cyano, nitro, hydroxyl, substituted or unsubstituted alkyl, perfluoroalkyl, —C(=O)$R^5$, —$OR^5$, —C(O)$R^5$, —C(O)$OR^5$, and —C(O)$NR^6R^7$, wherein each j is independently an integer selected from 0, 1, 2, and 3;
$R^3$ and $R^{3'}$ are each independently selected from hydrogen, halogen, substituted or unsubstituted alkyl, perfluoroalkyl, substituted or unsubstituted cycloalkyl, substituted or unsubstituted aryl, and substituted or unsubstituted alkylaryl.

In another aspect the disclosure provides a compound of Formula I, wherein the compound of Formula I has Formula IV:

(IV)

$(R^1)_m$—[phenyl]$_y$—X—$(CH_2)_q$—X'—[phenyl ring with C(=O)N($R^3$)-W]

wherein:
X and X' are each independently absent or are each independently selected from O, S, and $NR^4$;
y is independently an integer selected from 0 and 1;

q is independently an integer selected from 0, 1, 2, 3, 4, 5 and 6;

m and t are each independently an integer selected from 0, 1, 2, 3, and 4;

W is independently selected from C=O, CHR³, O, S, SO, SO₂, and NR³;

R¹ is independently selected from hydrogen, halogen, cyano, nitro, hydroxyl, substituted or unsubstituted alkyl, perfluoroalkyl, —(CH₂)$_j$C(=O)R⁵, —(CH₂)$_j$OR⁵, —(CH₂)$_j$C(O)R⁵, —(CH₂)$_j$C(O)OR⁵, and (CH₂)$_j$C(O)NR⁶R⁷, wherein each j is independently an integer selected from 0, 1, 2, and 3;

R³ is independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted aryl, and substituted or unsubstituted alkylaryl; and R⁵, R⁶, and R⁷ are each independently selected from hydrogen and substituted or unsubstituted alkyl.

In another aspect the disclosure provides a compound of Formula IV, wherein:

X is independently absent and X' is independently O;

y is independently 1;

q is independently 1;

R¹ is independently selected from hydrogen, halogen, cyano, nitro, hydroxyl, substituted or unsubstituted alkyl, perfluoroalkyl, —C(=O)R⁵, —OR⁵, —C(O)R⁵, —C(O)OR⁵, and —C(O)NR⁶R⁷, wherein each j is independently an integer selected from 0, 1, 2, and 3;

R³ is independently selected from hydrogen, halogen, substituted or unsubstituted alkyl, perfluoroalkyl, substituted or unsubstituted cycloalkyl, substituted or unsubstituted aryl, and substituted or unsubstituted alkylaryl.

In another aspect the disclosure provides a compound of Formula I, wherein the compound of Formula I has Formula V:

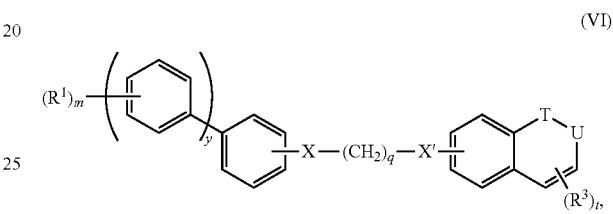

wherein:

m and t are each independently an integer selected from 0, 1, 2, 3, and 4;

W is independently selected from C=O, CHR³, O, S, SO, SO₂, and NR³;

R¹ is independently selected from hydrogen, halogen, cyano, nitro, hydroxyl, substituted or unsubstituted alkyl, perfluoroalkyl, —(CH₂)$_j$C(=O)R⁵, —(CH₂)$_j$OR⁵, —(CH₂)$_j$C(O)R⁵, —(CH₂)$_j$C(O)OR⁵, and (CH₂)$_j$C(O)NR⁶R⁷, wherein each j is independently an integer selected from 0, 1, 2, and 3;

R³ is independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted aryl, and substituted or unsubstituted alkylaryl; and R⁵, R⁶, and R⁷ are each independently selected from hydrogen and substituted or unsubstituted alkyl.

In another aspect the disclosure provides a compound of Formula V, wherein:

R¹ is independently selected from hydrogen, halogen, cyano, nitro, hydroxyl, substituted or unsubstituted alkyl, perfluoroalkyl, —C(=O)R⁵, —OR⁵, —C(O)R⁵, —C(O)OR⁵, and —C(O)NR⁶R⁷, wherein each j is independently an integer selected from 0, 1, 2, and 3;

R³ is independently selected from hydrogen, halogen, substituted or unsubstituted alkyl, perfluoroalkyl, substituted or unsubstituted cycloalkyl, substituted or unsubstituted aryl, and substituted or unsubstituted alkylaryl.

In another aspect the disclosure provides a compound of Formula I, wherein the compound of Formula I has Formula VI:

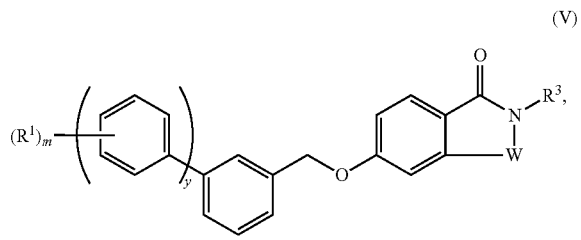

wherein:

X and X' are each independently absent or are each independently selected from O, S, and NR⁴;

y is independently an integer selected from 0 and 1;

q is independently an integer selected from 0, 1, 2, 3, 4, 5 and 6;

m and t are each independently an integer selected from 0, 1, 2, 3, and 4;

T and U are each independently selected from C=O, CHR³, O, S, SO, SO₂, and NR³, or T and U each independently form —CR³=CR³'— or —CR³=N—;

R¹ is independently selected from hydrogen, halogen, cyano, nitro, hydroxyl, substituted or unsubstituted alkyl, perfluoroalkyl, —(CH₂)$_j$C(=O)R⁵, —(CH₂)$_j$OR⁵, —(CH₂)$_j$C(O)R⁵, —(CH₂)$_j$C(O)OR⁵, and (CH₂)$_j$C(O)NR⁶R⁷, wherein each j is independently an integer selected from 0, 1, 2, and 3;

R³ is independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted aryl, and substituted or unsubstituted alkylaryl; and R⁵, R⁶, and R⁷ are each independently selected from hydrogen and substituted or unsubstituted alkyl.

In another aspect the disclosure provides a compound of Formula VI, wherein:

X is independently absent and X' is independently 0;

y is independently 1;

q is independently 1;

T and U each independently form —CR³=CR³'— or —CR=N—;

R¹ is independently selected from hydrogen, halogen, cyano, nitro, hydroxyl, substituted or unsubstituted alkyl, perfluoroalkyl, —C(=O)R⁵, —OR⁵, —C(O)R⁵, —C(O)OR⁵, and —C(O)NR⁶R⁷, wherein each j is independently an integer selected from 0, 1, 2, and 3;

R³ is independently selected from hydrogen, halogen, substituted or unsubstituted alkyl, perfluoroalkyl, substituted or unsubstituted cycloalkyl, substituted or unsubstituted aryl, and substituted or unsubstituted alkylaryl.

In another aspect the disclosure provides a compound of Formula I, wherein the compound of Formula I has Formula VII:

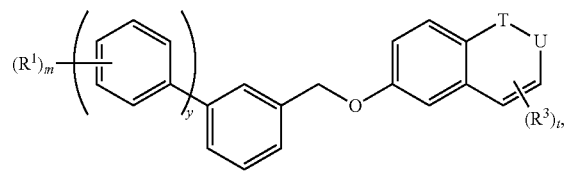

(VII)

wherein:

m and t are each independently an integer selected from 0, 1, 2, 3, and 4;

T and U are each independently selected from C=O, $CHR^3$, O, S, SO, $SO_2$, and $NR^3$, or T and U each independently form —$CR^3$=$CR^{3'}$— or —$CR^3$=N—;

$R^1$ is independently selected from hydrogen, halogen, cyano, nitro, hydroxyl, substituted or unsubstituted alkyl, perfluoroalkyl, —$(CH_2)_jC(=O)R^5$, —$(CH_2)_jOR^5$, —$(CH_2)_jC(O)R^5$, —$(CH_2)_jC(O)OR^5$, and $(CH_2)_jC(O)NR^6R^7$, wherein each j is independently an integer selected from 0, 1, 2, and 3;

$R^3$ is independently selected from hydrogen, halogen, cyano, amino, nitro, hydroxyl, substituted or unsubstituted alkyl, perfluoroalkyl, substituted or unsubstituted alkenyl, substituted or unsubstituted alkynyl, substituted or unsubstituted cycloalkyl, substituted or unsubstituted aryl, and substituted or unsubstituted alkylaryl; and $R^5$, $R^6$, and $R^7$ are each independently selected from hydrogen and substituted or unsubstituted alkyl.

In another aspect the disclosure provides a compound of Formula VII, wherein:

T and U each independently form —$CR^3$=$CR^{3'}$— or —$CR^3$=N—;

$R^1$ is independently selected from hydrogen, halogen, cyano, nitro, hydroxyl, substituted or unsubstituted alkyl, perfluoroalkyl, —C(=O)$R^5$, —$OR^5$, —C(O)$R^5$, —C(O)$OR^5$, and —C(O)$NR^6R^7$, wherein each j is independently an integer selected from 0, 1, 2, and 3; and $R^3$ is independently selected from hydrogen, halogen, substituted or unsubstituted alkyl, perfluoroalkyl, substituted or unsubstituted cycloalkyl, substituted or unsubstituted aryl, and substituted or unsubstituted alkylaryl.

In another aspect the disclosure provides a compound of Formula I, wherein the compound of Formula I is:

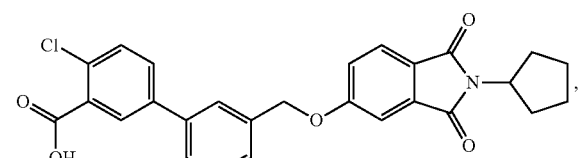

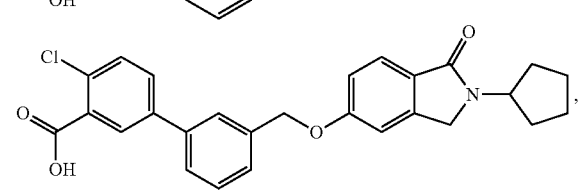

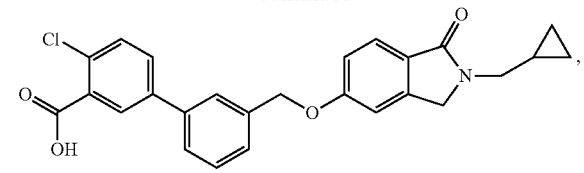

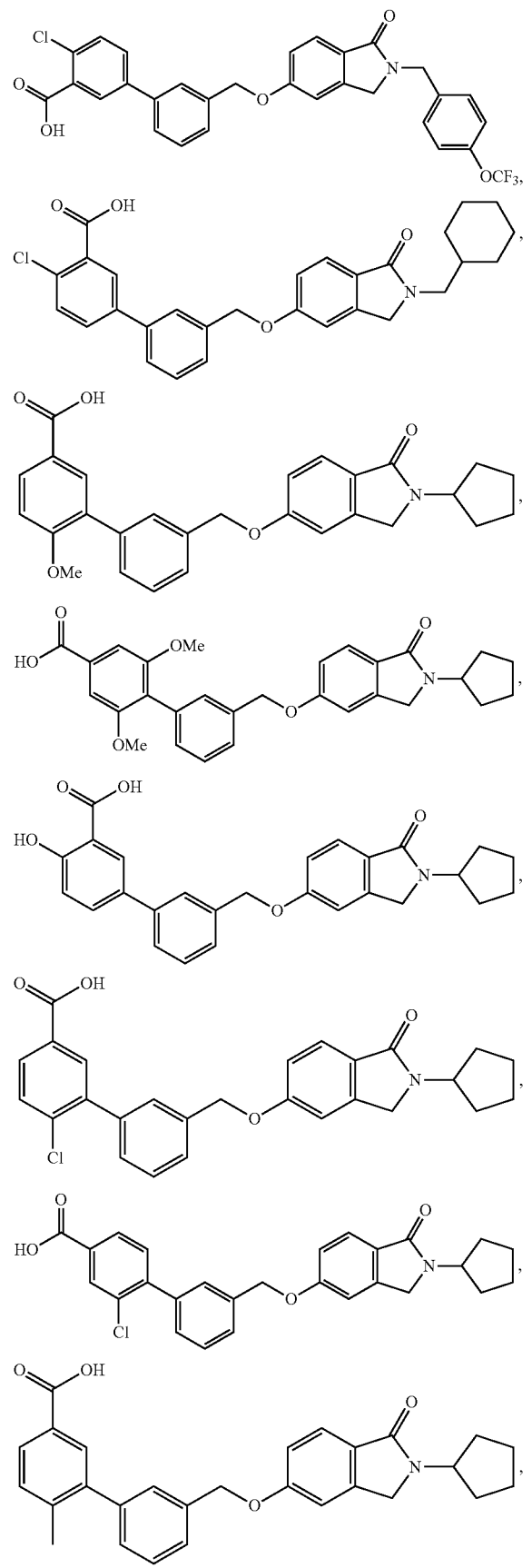
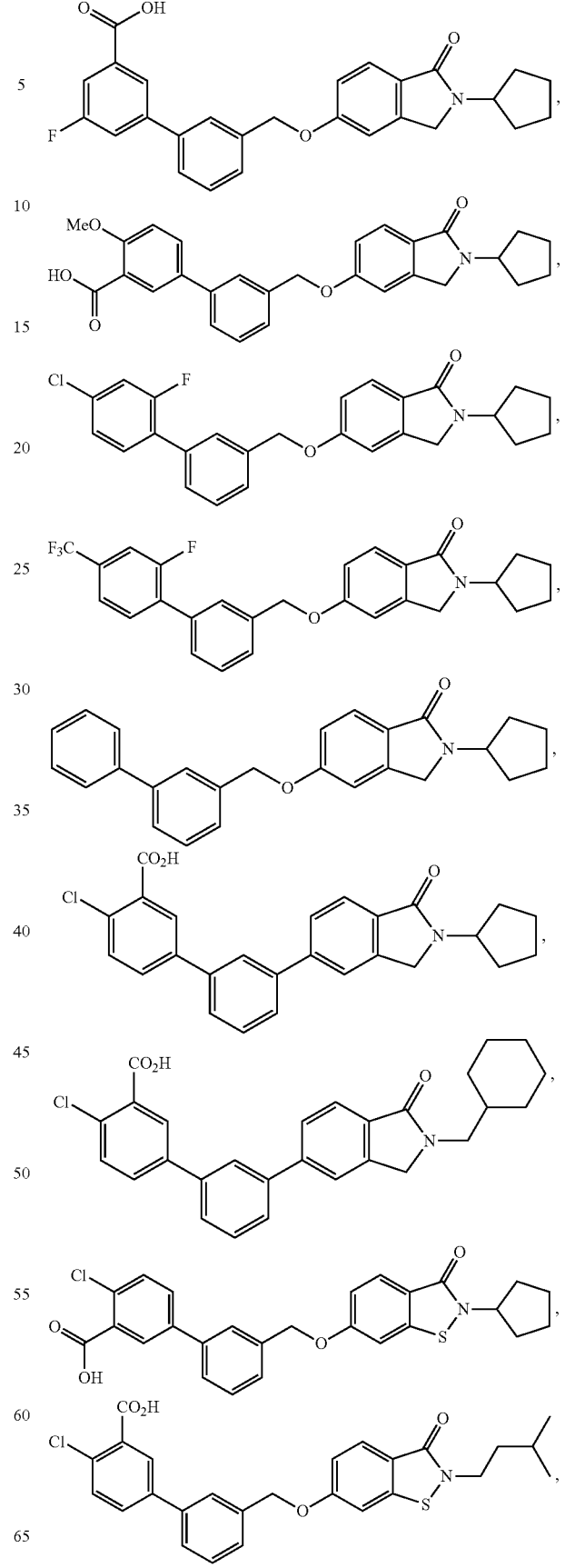

-continued
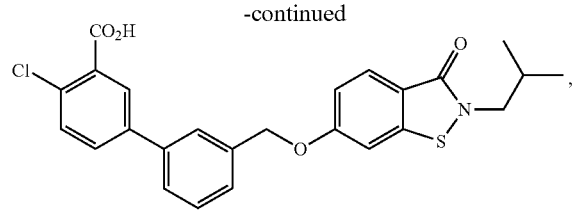
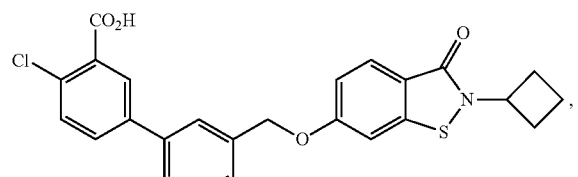
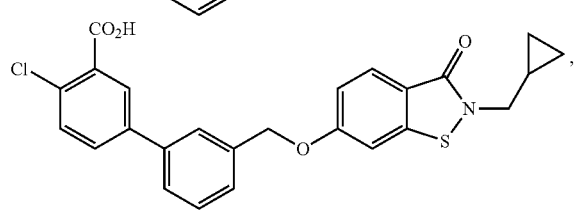
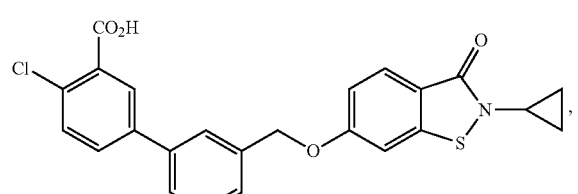
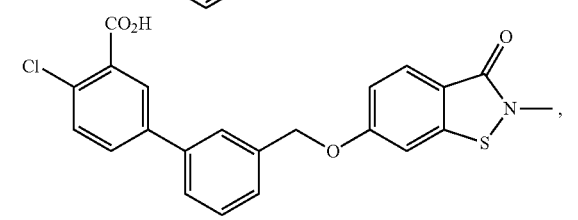
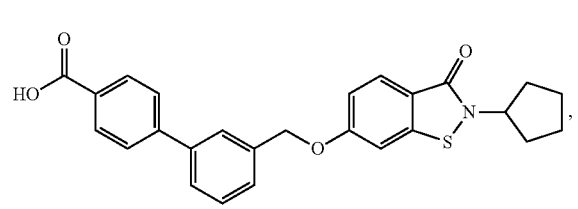
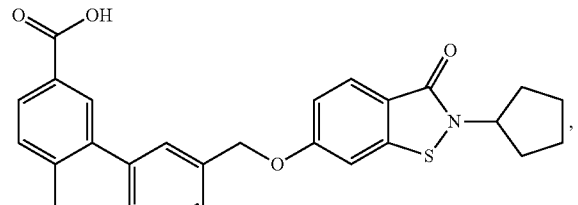
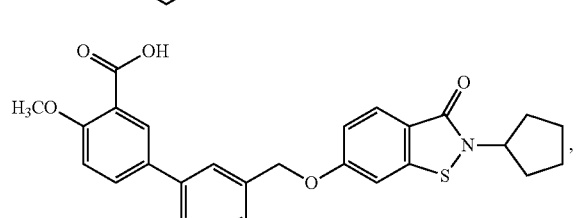
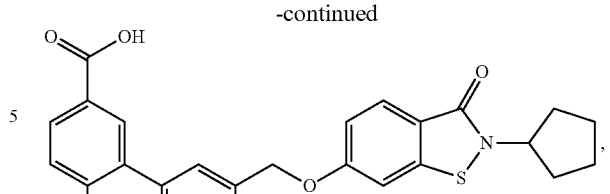
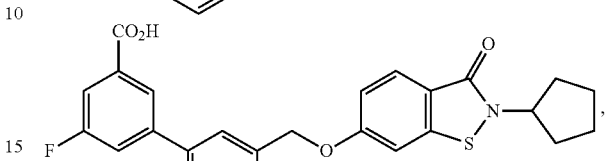
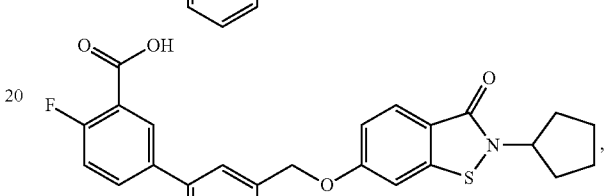
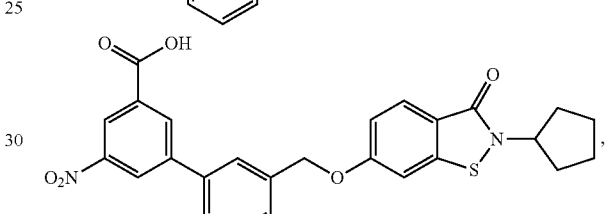
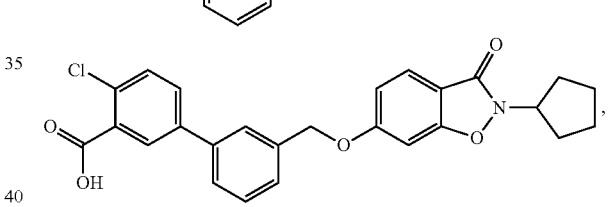
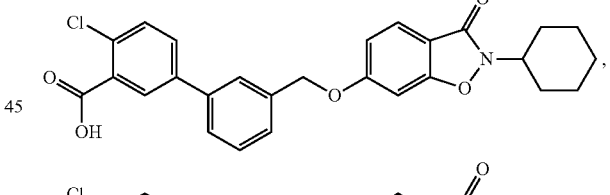
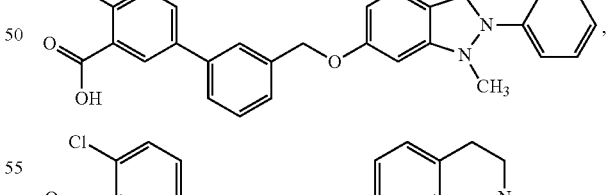
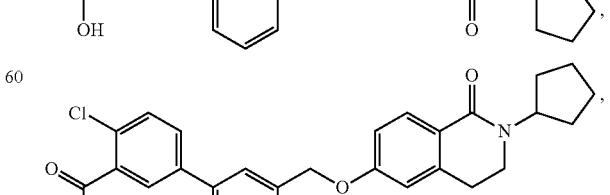

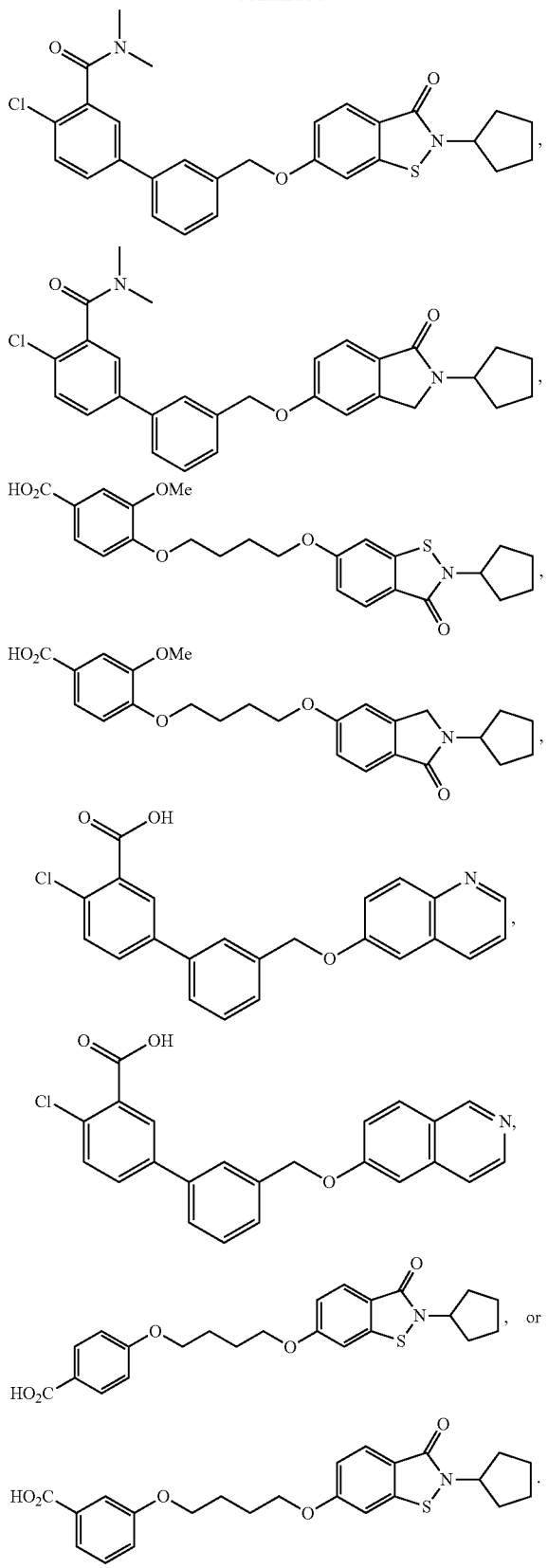

In another aspect the disclosure provides methods for treating a CNS disorder including schizophrenia, anxiety and addiction, by administering to a subject in need thereof, an effective amount of a compound having Formula I, thereby treating the disorder.

In another aspect the disclosure provides methods for treating a CNS disorder, wherein the disorder is an addictive disorder.

In another aspect the disclosure provides methods for treating a CNS disorder, wherein the disorder is an addictive disorder, and wherein the addictive disorder is nicotine addiction, alcohol addiction, opiate addiction, amphetamine addiction, methamphetamine addiction, or cocaine addiction.

In another aspect the disclosure provides methods for treating a CNS disorder, wherein the disorder is an addictive disorder, and wherein the addictive disorder is nicotine addiction.

In another aspect the disclosure provides methods for treating a CNS disorder, wherein the disorder is an addictive disorder, and wherein the addictive disorder is cocaine addiction.

In another aspect the disclosure provides methods for treating a CNS disorder, wherein the disorder is an addictive disorder, and wherein the addictive disorder is schizophrenia.

In another aspect the disclosure provides methods for treating a warm-blooded animal having an addictive disorder or schizophrenia, by administering to the animal an effective amount of a compound having Formula I, thereby treating the disorder or schizophrenia.

In another aspect the disclosure provides a pharmaceutical composition including a compound having Formula I, and a pharmaceutical acceptable carrier.

In another aspect the disclosure provides methods for treating substance abuse, by administering to a subject in need thereof, an effective amount of a compound having Formula I, wherein the effective amount is sufficient to diminish, inhibit or eliminate desire for and/or consumption of the substance in the subject.

In another aspect the disclosure provides methods for treating substance abuse, wherein the substance is nicotine, alcohol, opiates, amphetamines, methamphetamines, or cocaine.

In another aspect the disclosure provides a method for treating an addictive disorder, by a) administering to a subject in need thereof, an effective amount of a compound having Formula I, during a first time period, wherein the first time period is a time period wherein the subject expects to be in an environment wherein, or exposed to stimuli in the presence of which, the subject habitually uses an addictive substance; and b) administering an effective amount of a compound having Formula I during a second time period, wherein the second time period is a time period wherein the subject is suffering from withdrawal.

As used herein, an "effective amount" of an antagonist is an amount that modulates the normal activity of mGluII receptors in a subject. A "normal" activity of mGlu receptor represents a level of activity in a cell or subject not having an mGluR-related disorder and can be determined using methods known in the art, some of which are disclosed herein. For example, the disclosed compounds can be administered at a concentration of about 0.1-50 mg/kg, in certain aspects between 0.1 and 5 mg/kg. In some aspects of the disclosure, an effective amount is at least 0.5 mg/kg, for example, 0.5 mg/kg to about 10 mg/kg, or 0.5 mg/kg to about 5 mg/kg. In certain aspects of the disclosure, the disclosed compounds can be administered at a concentration of about 0.5 mg/kg or 1 mg/kg.

The disclosed compounds may also be administered in an amount of between about 0.01 and 25 mg/kg body weight. In certain aspects, the compounds can be administered at a concentration equal to or greater than 1 mg/kg, for example between about 3 and about 20 mg/kg. In other aspects, the disclosed compounds can be is administered at a concentration of between about 5 and about 15 mg/kg. In other aspects, the disclosed compounds can be administered at between about 7 and about 12 mg/kg, for example at 9 mg/kg. It will be understood that the disclosure provides a basis for further studies in humans to more precisely determine effective amounts in humans. Doses used for rodent studies provide a basis for the ranges of doses indicated herein for humans and other mammals.

Metabotropic Glutamate Disorders

The excitatory neurotransmitter L-glutamate has been shown to activate ligand-gated cationic channels termed N-methyl-D-aspartate (NMDA), alpha-amino-3-hydroxy-5-methyl-isoxazole-4-propionate (AMPA) and kainate (KA) receptors (ionotropic glutamate receptors; iGluRs) and to regulate ion channels and enzymes producing second messengers via specific receptors coupled to G-proteins. In contrast to ion channel-linked glutamate receptors (ionotropic), which facilitate fast synaptic transmission, metabotropic glutamate receptors (mGluRs) represent a heterogeneous family of receptor proteins that modulate synaptic function through coupling to multiple second messenger systems (Pin and Duvoisin, 1995). Metabo-tropic glutamate receptors are currently classified into three groups based on sequence homology, second messenger coupling and similar agonist pharmacology. Group I mGluRs include mGluRt and mGluRs, which are coupled to phosphoinositide (PI) hydrolysis when expressed in non-neuronal cells. Group II mGluRs, which include mGluR2 and mGluR3, are negatively coupled to cyclic adenosine 3',5'-monophosphate (CAMP) formation. Group III mGluRs are the most heterogeneous subgroup of mGluRs, and include mGluR4, mGluR6, mGluR7 and mGluR8. Group III mGluRs are also negatively coupled to CAMP formation when expressed in non-neuronal cells. The characterization of mGluRs in the central nervous system (CNS) represents a new area of therapeutic opportunity.

Metabotropic glutamate receptors (mGluRs) represent a heterogeneous family of receptor proteins that modulate synaptic function through coupling to multiple second messenger systems (Pin and Duvoisin, 1995). Metabo-tropic glutamate receptors are currently classified into three groups based on sequence homology, second messenger coupling and similar agonist pharmacology. Group I mGluRs include mGluR1 and mGluR5, which are coupled to phosphoinositide (PI) hydrolysis when expressed in non-neuronal cells. Group II mGluRs, which include mGluR2 and mGluR3, are negatively coupled to cyclic adenosine 3',5'-monophosphate (CAMP) formation. Group III mGluRs are the most heterogeneous subgroup of mGluRs, and include mGluR4, mGluR6, mGluR7 and mGluR8. Group III mGluRs are also negatively coupled to CAMP formation when expressed in non-neuronal cells.

Disorders that can be effectively treated by modulating the activity of mGluII receptors, referred to herein as metabotropic glutamate disorders, include CNS disorders such as schizophrenia, and addictive disorders such as cocaine addiction. Metabotropic glutamate disorders include disorders that involve one or both of a Group I metabotropic glutamate receptor (mGluR) and one or both of a Group II mGluR. Addictive metabotropic glutamate disorders also include, for example, nicotine addiction, alcohol addiction, opiate addiction, amphetamine addiction, cocaine addiction, methamphetamine addiction, and the like.

The excitatory neurotransmitter L-glutamate has been shown to activate ligand-gated cationic channels termed N-methyl-D-aspartate (NMDA), alpha-amino-3-hydroxy-5-methyl-isoxazole-4-propionate (AMPA) and kainite (KA) receptors (ionotropic glutamate receptors; iGluRs) (Johnson and Ascher, 1987; Honore et al., 1988; Lodge and Collingridge, 1991) and to regulate ion channels and enzymes producing second messengers via specific receptors coupled to G-proteins (Baskys, 1994). In contrast to ion channel-linked glutamate receptors (ionotropic) which facilitate fast synaptic transmission, metabotropic glutamate receptors (mGluRs) represent a heterogeneous family of receptor proteins that modulate synaptic function through coupling to multiple second messenger systems (Pin and Duvoisin, 1995). Metabotropic glutamate receptors are currently classified into three groups based on sequence homology, second messenger coupling and similar agonist pharmacology. Group I mGluRs include mGluRt and mGluRs, which are coupled to phosphoinositide (PI) hydrolysis when expressed in non-neuronal cells. Group II mGluRs, which include mGluR2 and mGluR3, are negatively coupled to cyclic adenosine 3',5'-monophosphate (CAMP) formation. Group III mGluRs are the most heterogeneous subgroup of mGluRs, and include mGlu&, mGlu&, mGluR7 and mGluRs. Group III mGluRs are also negatively coupled to CAMP formation when expressed in non-neuronal cells (Nakanishi, 1992; Schoepp, 1994; Pin and Duvoisin, 1995). The characterization of mGluRs in the central nervous system (CNS) represents a new area of therapeutic opportunity.

Thus, in one embodiment, the disclosed compounds of Formula I are selective for Group II metabotropic glutamate receptors. As such, the disclosed compounds may produce anxiolytic activity in the potentiated startle and elevated plus maze models of anxiety (Helton et al., 1997; Monn et al., 1997). As a result of this, the disclosed compounds of Formula I may be useful in the treatment of anxiety-related disorders.

Chronic administration of nicotine results in tolerance and dependence in both humans (Schachter, 1979; Shiffnian and Phil, 1979; Henningfield et al., 1995) and rodents (Clarke, 1987; Helton et al., 1993). Cessation of chronic nicotine exposure in humans results in a number of withdrawal symptoms which include anxiety and irritability (Hughes and Hatsukami, 1992; Henningfield et al., 1995). In rodents, however, signs of overt physical or behavioral withdrawal from chronic nicotine are limited. As such, there have been few robust, well accepted models for evaluating nicotine withdrawal in rodents (Emmett-Oglesby et al., 1990). Chronic nicotine exposure in rats results in a robust increase in startle responding during the first 5 days following withdrawal, and re-administration of nicotine (0.4 mg/kg i.p.) greatly attenuates the enhanced startle response subsequent to nicotine withdrawal (Helton et al., 1993). This enhanced sensorimotor responsiveness may reflect one or more of the withdrawal symptoms reported in man, and may provide a sensitive model for examining pharmacological intervention Metabotropic glutamate receptors can modulate both excitatory and inhibitory neuronal transmission by pre and postsynaptic mechanisms. The role of glutamate in nicotine withdrawal is supported by an increasing number of studies reporting changes in glutamatergic function following both acute and chronic nicotine administration and/or withdrawal. For example, there have been reported interactions between the nicotinic cholinergic system and the glutamatergic system (Aizenman et al., 1991; Vidal, 1994; Zhang et uZ., 1994). Acute nicotine administration has been shown to enhance the release of glutamate through activation of nicotinic receptors located on presynaptic terminals and to facilitate evoked glutamate synaptic transmission (McGehee et al., 1995; Gray et al., 1996). However, the pharmacological characterization and understanding of the function of mGluRs in nicotine withdrawal have been limited due to a lack of potent, systemically active and selective pharmacological probes. As such, the disclosed compounds of Formula I may be useful in treating patients suffering from withdrawal from chronic nicotine exposure and/or smoking cessation. Thus, the disclosure also provides methods for treating nicotine addiction by administering one or more compounds disclosed herein. The method includes administering to a subject in need thereof, an effective amount of at least one antagonist which modulates the Group II mGluR receptor, thereby treating the nicotine addiction and/or withdrawal symptoms.

It will be understood that the data provided in the Examples section for certain drugs of abuse, such as cocaine addiction, is applicable to other drugs of abuse as well. It has been extensively hypothesized that dependence on all major drugs of abuse is mediated by the same neurobiological and behavioral mechanisms (Markou et al. 1998; Markou A & Kenny P J 2002 Neuroadaptations to chronic exposure to drugs of abuse: Relevance to depressive symptomatology seen across psychiatric diagnostic categories, Neurotoxicity Research, 4(4), 297-313.; Koob & Le Moal, Neuropsychopharmacology, 24(2):97-129 2001; Barr, A. M., Markou, A. and Phillips, A. G. (2002) A "crash" course on psychostimulant withdrawal as a model of depression, Trends in Pharmacological Sciences, 23(1), 475-482, incorporated in its entirety by reference; Cryan, J. F., Markou, A. and Lucki, I. (2002) Assessing antidepressant activity in rodents: Recent developments and future needs, Trends in Pharmacological Sciences, 23(5), 238-245). Thus, one would expect that a compound effective in treating one drug addiction is likely to be effective in treating another addiction also. For example, increase in serotonergic neurotransmission by co-administration of the selective serotonin reuptake inhibitor fluoxetine+the serotonin-1A receptor antagonist p-MPPI reversed the depression-like aspects of both amphetamine and nicotine withdrawal (Harrison, Liem & Markou, Neuropsycho-pharmacology 2001; incorporated in its entirety by reference). Further, withdrawal from all major drugs of abuse (nicotine, cocaine, amphetamine, alcohol, opiates, phencyclidine) results in elevations in brain reward thresholds reflecting a depression-like state (references in reviews Markou et al. 1998; Markou & Kenny 2002; Barr et al. 2002; Cryan et al. 2002; and original research reference for phencyclidine: Spielewoy, C. & Markou, A. 2003, Withdrawal from chronic treatment with phencyclidine induces long-lasting depression in brain reward function, Neuropsychopharmacology, 28, 1106-1116 and cocaine: Ahmed et al. 2002). Thus, treating such depression-like aspects of drug dependence and withdrawal may assist people in abstaining from drug use.

In another aspect, the metabotropic glutamate disorder is depression. Blockade of mGluR2/3 receptors has antidepressant properties as reflected in reversal of the negative affective (depression-like) aspects of nicotine withdrawal. Thus, blockade of mGluR2 and mGluR3 reverses depression-like symptoms observed during drug withdrawal, and possibly depression observed during drug dependence (Ahmed, S. H., et al. Nature Neuroscience, 5: 625-626 (2002), incorporated in its entirety by reference). Therefore, administration of an effective amount of an antagonist of mGluR2 and mGluR3 is likely to be efficacious for treating non-drug-induced depressions, based on the known neurobiological similarities mediating drug- and non-drug-induced depressions (Markou et al. 1998, incorporated in its entirety by reference; Barr et al., 2002, incorporated in its entirety by reference; Cryan et al., 2002; incorporated in its entirety by reference; Harrison et al., Neuropsychopharmacology, 25:55-71 (2001), incorporated in its entirety by reference; Markou A and Kenny P J 2002, Neuroadaptations to chronic exposure to drugs of abuse: Relevance to depressive symptomatology seen across psychiatric diagnostic categories, Neurotoxicity Research, 4(4), 297-313; incorporated in its entirety by reference).

Additional observations further support the conclusion that antagonists of mGluR2 and/or mGluR3 can be used to effectively treat non-drug-induced depressions, as well. First, it has been shown that co-administration of the selective serotonin reuptake inhibitor fluoxetine and the serotonin-1A receptor antagonist p-MPPI, a clinically proven antidepressant drug treatment, reverses the depression-like aspects of both nicotine and amphetamine withdrawal (Harrison et al., (2001); incorporated in its entirety by reference). Second, co-administration of the selective serotonin reuptake inhibitor paroxetine and the serotonin-1A receptor antagonist p-MPPI, another clinically proven antidepressant drug treatment, also reversed amphetamine withdrawal. Third, bupropion, another clinically proven antidepressant treatment, reverses the depression-like aspects of nicotine withdrawal (Cryan, J. F., et al., Psychopharmacology, 168, 347-358 (2003). Thus, clinically proven antidepressant treatments reverse the depression-like aspects of drug withdrawal. Therefore, it can be inferred that a treatment (e.g., mGluR2/3 antagonist) that normalized thresholds in the model, would be a clinically effective treatment. Further, the reversal of both amphetamine and nicotine withdrawal by the same antidepressant treatment indicates that there are commonalities in various types of depression, independent of what the depression-induction mechanism is and/or the primary site of action of the drug of abuse, i.e., nicotinic receptor for nicotine, monoaminergic transporters for amphetamine.

The disclosure also provides methods for treating depressive symptoms and anxiety symptoms of depression. The method includes administering to a subject in need thereof, an effective amount of at least one antagonist which modulates the mGluR2 or mGluR3 receptor, thereby treating the depressive symptoms and anxiety symptoms. In another aspect, the disclosure provides at least one antagonist of mGluR2 or mGluR3 receptor that can be administered during a depressed time period, wherein the subject experiences symptoms of depression, whereas an mGluR5 antagonist is administered during time periods when the subject experiences symptoms of anxiety. Depression is characterized by both depressive symptoms and anxiety symptoms. Thus, the disclosure, which provides an mGluR2/3/5 combination treatment as an effective antidepressant, with the mGluR2/3 antagonism ameliorating depressive symptoms and the mGluR5 antagonist ameliorating anxiety symptoms. Accordingly, this embodiment takes advantage of the anti-depressive properties of mGluR2/3 antagonists and the anxiolytic properties of mGluR5 antagonists (See e.g., Cosford, N. D., et al., J. Med. Chem. 6; 46(2):204-6 (2003); Brodkin J., et al., Eur. J. Neurosci., 16(11):2241-4 (2002); and Brodkin J., et al., Pharmacol. Biochem. Behav. 73(2):359-66 (2002)). Since anxiety is known to be a major symptom of the overall syndrome of depression, this aspect of the disclosure is effective at treating the anxiety symptoms of depression.

Depressive symptoms and anxiety symptoms are well known in the art. Methods of the disclosure treat one or more symptoms of depression and one or more symptoms of anxiety. Symptoms of depression, include, for example, but are not limited to, the following: a persistent sad, anxious or "empty" mood; sleeping too little or sleeping too much;

reduced appetite and weight loss, or increased appetite and weight gain; loss of interest or pleasure in activities once enjoyed; restlessness or irritability; persistent physical symptoms that don't respond to treatment, e.g., headaches, chronic pain, or constipation and other digestive disorders; difficulty concentrating, remembering, or making decisions; fatigue or loss of energy; feeling guilty, hopeless or worthless; and thoughts of death or suicide.

Symptoms of anxiety include, but are not limited to, the following: excessive worry, occurring more days than not, over a period of months, for example over a period of at least six months; unreasonable worry about a number of events or activities, such as work or school and/or health; the inability to control worry; restlessness, feeling keyed-up or on edge; tiredness; problems concentrating; irritability; muscle tension; and trouble falling asleep or staying asleep, or restless and unsatisfying sleep.

The disclosure also provides methods for treating a metabotropic glutamate disorder, the subject is a mammalian subject, for example a human subject afflicted with a metabotropic glutamate receptor disorder, for example nicotine addiction, cocaine addiction, or depression. The examples herein illustrate the methods of the disclosure in rodents. However, it will be understood that the methods are expected to be efficacious in human subjects as well, due to the similarity between rodents and humans in the physiology of addictive disorders and depression (Markou et al. 998; Markou and Kenny 2002, incorporated in its entirety by reference), and the structure of mGlu receptors (Schoepp et al. Neuropharm. 999, 38, 1431-1476).; Schoepp D D (2001), J Pharmacol Exp Ther 299:12-20).

As used herein, the phrase "Simultaneous administration" of two or more antagonists includes administration of the agonists to a subject within a short enough time period such that a sufficient concentration of each of the antagonists is present in the subject at the same time to modulate their respective mGlu receptor targets. Therefore, it will be recognized that the maximum time difference between administrations of antagonists that represent simultaneous administration depends on the half-life of the antagonists administered, the amount of antagonist administered, and the method and location by which the antagonists are administered, for example.

The disclosure also provides antagonists that can be administered for periods of weeks, months, years, and possibly indefinitely for subjects exhibiting failure to abstain from drug use or for chronic depressive disorders that may be unrelated to drug use or induced by drug use, but not remitting spontaneously without the methods suggested herein.

The disclosure also provides methods for inhibiting drug-taking behavior, treating depression, and/or treating the depression-like state associated with drug use and dependence (Ahmed et al., 2002, incorporated herein in its entirety by reference), or with addictive drug withdrawal, that includes administering to a subject in need thereof, an effective amount of at least one antagonist which modulates mGluR2 and/or mGluR3, thereby treating consumption of the addictive substance, depression, or the depression-like state of the addictive drug dependence or drug withdrawal states.

In certain aspects, the effective amount of at least one antagonist is administered to decrease nicotine consumption. For example, in one aspect an effective amount of an antagonist of mGluR2 and mGluR3, can be administered to decrease nicotine consumption. In certain aspects of the disclosure, an inhibitor of mGluR2 and/or mGluR3 is administered while a subject is experiencing withdrawal. In another aspect of the disclosure, an inhibitor of mGluR2 and/or mGluR3 is administered during a time period when a subject is actively using an addictive substance. In another aspect of the disclosure, an inhibitor of mGluR2 and/or mGluR3 is administered during a time period when a subject is actively experiencing depression associated with drug use or not associated with drug use.

The disclosure also provides a method for antagonizing at least two of mGluR2, mGluR3, and mGluR5, that includes simultaneously administering to a subject in need thereof, an amount of at least two antagonists that modulate at least two of mGluR2, mGluR3, and mGluR5. The amount of each antagonist is sufficient to modulate its target mGluR. This amount may be less than an effective amount of the antagonist when administered alone. However, the amount administered in these embodiments is sufficient so that the combination of antagonists is effective for treating a metabotropic disorder. In certain aspects, each antagonist is provided at an effective amount for treating a metabotropic glutamate disorder. In certain aspects, the subject is afflicted with depression, a nicotine addiction, or a cocaine addiction. In certain aspects, an antagonist that modulates mGluR2 and mGluR3 is administered along with an antagonist that modulates mGluR5.

The disclosure also provides a method for treating an addictive disorder, also referred to herein as substance abuse, that includes administering to a subject in need thereof, an effective amount of at least one antagonist that modulates at least one of mGluR2, 3, and 5 during a first time period, followed by administering at least one antagonist that modulates at least one of mGluR2 and/or 3 during a second time period. The first time period, for example, is a time period wherein the subject expects to be in an environment wherein, or exposed to stimuli in the presence of which, the subject habitually uses an addictive substance, or wherein the subject is actively using the addictive substance. The second time period, for example, is a time period wherein the subject is suffering from withdrawal and/or depression.

The route of delivery of the antagonists or agonists employed by disclosed methods may be determined by the particular disorder. Antagonists or agonists may be delivered orally, intravenously, intraperitoneally, intramuscularly, subcutaneously, intranasally, and intradermally, as well as, by transdermal delivery (e.g., with a lipid-soluble carrier in a skin patch placed on skin), or even by gastrointestinal delivery (e.g., with a capsule or tablet). Furthermore, antagonists or agonists used in the methods of the disclosure, in certain aspects are delivered directly to the brain or certain regions of the brain to activate or inhibit receptors at specific brain sites producing the desirable effect without inhibiting or activating receptors at other brain sites, thus avoiding undesirable side-effects or actions that may counteract the beneficial therapeutic action mediated by the former site(s). The dosage will be sufficient to provide an effective amount of an antagonist either singly or in combination, as discussed above. Some variation in dosage will necessarily occur depending upon the condition of the patient being treated, and the physician will, in any event, determine the appropriate dose for the individual patient. The dose will depend, among other things, on the body weight, physiology, and chosen administration regimen.

The antagonists employed in disclosed methods can be administered alone or in combination with pharmaceutically acceptable carriers, in either single or multiple doses. Suitable pharmaceutical carriers include inert solid diluents or fillers, sterile aqueous solutions, and various nontoxic organic solvents. The pharmaceutical compositions formed by combining one or more antagonist with the pharmaceutically acceptable carrier are then readily administered in a variety of dosage forms such as tablets, lozenges, syrups, injectable solutions, and the like. These pharmaceutical carriers can, if desired, contain additional ingredients such as flavorings, binders, excipients, and the like. Thus, for purposes of oral administration, tablets containing various excipients such as sodium citrate, calcium carbonate, and calcium phosphate are employed along with various disintegrants such as starch, and potato or tapioca starch, alginic acid, and certain complex silicates, together with binding agents such as polyvinylpyrolidone, sucrose, gelatin, and acacia. Additionally, lubricating agents, such as magnesium stearate, sodium lauryl sulfate, and talc are often useful for tableting purposes. Solid compositions of a similar type may also be employed as fillers in salt and hard-filled gelatin capsules. Appropriate materials for this purpose include lactose or milk sugar and high molecular weight polyethylene glycols.

When aqueous suspensions of elixirs are desired for oral administration, the antagonists may be combined with various sweetening or flavoring agents, colored matter or dyes, and if desired, emulsifying or suspending agents, together with diluents such as water, ethanol, propylene glycol, glycerin, and combinations thereof. For parenteral administration, solutions of preparation in sesame or peanut oil or in aqueous polypropylene glycol are employed, as well as sterile aqueous saline solutions of the corresponding water soluble pharmaceutically acceptable metal salts previously described. Such an aqueous solution should be suitably buffered if necessary and the liquid diluent first rendered isotonic with sufficient saline or glucose. These particular aqueous solutions are especially suitable for intravenous, intramuscular, subcutaneous, and intraperitoneal injection. The sterile aqueous media employed are all readily obtainable by standard techniques well known to those skilled in the art.

The disclosure also provides methods for screening for an agent that improves the ability of a known inhibitor to at least partially normalize intracranial self-stimulation (ICSS) threshold and/or improves the ability of a known inhibitor to inhibit consumption of an addictive substance for a non-human, mammalian subject. The method includes: a) affecting the ICSS threshold of the subject; b) administering to the subject, a sufficient amount of the known inhibitor to inhibit consumption of an addictive substance and/or at least partially normalize the ICSS threshold when administered alone or in combination with another inhibitor, wherein the known inhibitor is an antagonist of mGluR2 and/or mGluR3 and/or mGluR5; c) administering to the subject, an effective amount of a test agent, wherein the test agent is a known or suspected antagonist of mGluR2 and/or mGluR3 and/or mGluR5; and d) determining whether the test agent improves the ability of the known inhibitor, to at least partially normalize the ICSS threshold, and optionally to inhibit one or both of consumption of the addictive substance, thereby identifying an agent that improves the ability of the known inhibitor to normalize ICSS threshold and/or improves the ability of a known inhibitor to inhibit consumption of an addictive substance, or, alternatively, determining whether the test agent improves the ability of the known inhibitor, to at least decrease consumption of an addictive substance, and optionally to partially normalize the ICSS threshold or both thereby identifying an agent that improves at least the ability of the known inhibitor to inhibit consumption of an addictive substance and/or normalize ICSS threshold.

Intracranial self-stimulation (ICSS) thresholds are at least partially normalized when an increase or decrease on ICSS threshold caused by a metabotropic glutamate disorder is at least partially inhibited (i.e. adjusted back to the ICSS threshold of a subject that is not afflicted with the metabotropic glutamate disorder). For example, withdrawal from chronic nicotine administration (Kenny et al., 2003) or chronic self-administration of cocaine (Ahmed et al. 2002, incorporated in its entirety by reference) are known to elevate an ICSS threshold (see e.g., Kenny et al. 2003). Therefore, partial normalization of an ICSS threshold during cocaine administration or during nicotine withdrawal will lower the ICSS threshold from the elevated threshold, reflecting a depressed state, normally found during chronic cocaine administration or nicotine withdrawal, closer to that found in a normal subject. Accordingly, methods of this embodiment of the disclosure can utilize chronic administration of an addictive substance (e.g., cocaine) or termination of administration of an addictive substance (e.g., nicotine) to affect (i.e., denormalize) the ICSS threshold before or during administration of the known inhibitor and the test agent. Acute administration of an addictive substance typically decreases the ICSS threshold, while chronic administration of an addictive substance and/or termination of administration of an addictive substance typically increases the ICSS threshold.

In addition to the methods above, the ICSS threshold can be affected by other known methods. For example, the chronic mild stress procedure can be used to induce threshold elevations reversible by antidepressant treatments (Moreau J. L., Bos M., Jenck F., Martin J. R., Mortas P. and Wichmann J. (1996), Eur Neuropsychopharmacology, 6, 169-175; Moreau J. L., Bourson A., Jenck F., Martin J. R. and Mortas P. (1994), J Psychiatry Neurosci 19, 51-56; Moreau J. L., Jenck F., Martin J. R., Mortas P. and Haefely W. E. (1992), Eur Neuropsychopharmacology, 2, 43-49).

Methods for self-administration of an addictive agent and for analyzing ICSS are disclosed in U.S. Patent Application Publication No. 2006/0148835, the disclosure of which is hereby incorporated by reference in its entirety for all purposes. These methods can be used to identify an agent that is effective at improving the effectiveness of an inhibitor, but also can be used to determine which of the characteristics/symptoms/aspects associated with substance abuse or withdrawal are effected by the test agent.

The term "test agent" is used herein to mean any agent that is being examined for the ability to improve the ability of the known inhibitor to inhibit consumption of an addictive substance or normalize ICSS thresholds. The method generally is used as a screening assay to identify molecules that can act as a therapeutic agent for treating depressive disorders or addictive disorders such as cocaine addiction or nicotine addiction. As indicated above, the test agent can be an agent known to inhibit mGluR2, mGluR3, and/or mGluR5. Furthermore, the screening methods of the disclosure can be combined with other methods that analyze test agents for the ability to antagonize mGluR2, mGluR3, and/or mGluR5. For example, a cell based high throughput assay can be used to screen for test agents that are antagonists for mGluR2, mGluR3, and/or mGluR5, using methods known in the art. Test agents identified as antagonists of mGluR2, mGluR3, and/or mGluR5 can then be analyzed in the screening method provided in this embodiment of the disclosure, to determine whether the test agents improve the ability of the known inhibitor to inhibit consumption of an addictive substance or affect ICSS reward thresholds. A test agent can be any type of molecule, including, for example, a peptide, a peptidomimetic, a polynucleotide, or a small organic molecule, that one wishes to examine for the ability to act as a therapeutic agent, which is an agent that provides a therapeutic advantage to a subject receiving it.

The disclosure also provides kits that are useful for carrying out the methods of the disclosure. The components of the kits depend on the specific method that is intended to be performed by the kit. For example, the kit can be useful for carrying out a method to treat a metabotropic glutamate disorder. In this aspect, the kit can include at least one container that contains an antagonist that modulates metabotropic glutamate receptor 2 (mGluR2), mGluR3, and/or mGluR5. In one aspect, the kit includes a first container with an inhibitor of mGluR5 and a second container with an inhibitor of mGluR2 and/or mGluR3. In one aspect, the kit includes a container of MPEP and a container of LY341495. The antagonists included in the test kit are provided in an amount and form that is sufficient to allow an effective amount to be administered to the subject. The kit for example, can also include instructions regarding effective use of the antagonists in the treatment of substance abuse and depression. The kit in certain aspects includes information that is generally useful for a depressed individual or an individual suffering from an addiction.

In another aspect, the kits can be useful for screening for an agent that improves the ability of a known inhibitor to inhibit consumption of an addictive substance or at least partially normalize intracranial self-stimulation threshold. In this aspect, the kit for example, includes a container having a known inhibitor. Furthermore, the kit may include a container of an addictive substance to be administered to a non-human mammalian subject.

The disclosure also provides a method for treating an addictive disorder that includes administering to a subject in need thereof, an effective amount of a selective serotonin reuptake inhibitor, such as paroxetine, a serotonin-1A receptor antagonist, and/or bupropion, and administrating to the subject an effective amount of an antagonist of mGluR2, mGluR3, and/or mGluR5. In certain aspects of this embodiment, where an mGluR5 antagonist is administered, the mGluR5 administration is stopped during periods wherein the subject suffers from withdrawal. In certain aspects, administration of the selective serotonin reuptake inhibitor, a 5-HT1A receptor antagonist, and/or bupropion is commenced during periods wherein the subject suffers from withdrawal.

Cocaine Addiction

Cocaine addiction remains a major public health problem in the United States. There are several sources of motivation that contribute to the continuance of cocaine abuse, including: the positive reinforcing effects of cocaine; and the alleviation of the negative affective aspects of cocaine withdrawal. Conditioned stimuli previously associated with cocaine administration may also elicit conditioned "cravings" leading to the reinstatement of cocaine-seeking behavior even after a prolonged period of abstinence. Recent studies indicate that the neuronal mechanisms underlying various aspects of drug abuse may differ necessitating the use of different treatments for specific aspects of drug dependence. To date, a safe and effective pharmacological treatment for cocaine dependence has yet to be identified. Thus, there remains a need for the design of new chemical entities that may become future novel medications for cocaine addiction.

It as been found that repeated cocaine exposure may alter the function of Group II metabotropic glutamate receptors (mGluII receptors), pointing to a possible role of these mGluR subtypes in the development of cocaine dependence. In the disclosure, using a combination of rational design and library synthesis approaches, there is provided the design and synthesis of positive and negative allosteric modulators of mGluII receptors that are systemically active in vivo. The disclosed compounds are characterized in in vitro assays measuring potency and efficacy against mGluII receptors. The most potent and efficacious compounds are profiled in vitro against other mGluR subtypes, related proteins (e.g., $GABA_B$) and other central nervous systems (CNS) targets to determine selectivity. The disclosed compounds were also assessed for their pharmacokinetic (PK) properties including brain penetration. Finally, the disclosed compounds were evaluated in rat models assessing the different aspects of cocaine dependence: (1) the reinforcing effects of intravenously self-administering cocaine; (2) cue-induced reinstatement of cocaine-seeking behavior, and (3) the reward and motivational deficits associated with cocaine abstinence. Complementary experiments compare the effects of the disclosed compounds that have positive effects on cocaine-related behaviors with the effects of the same compounds on food motivated behaviors. Such comparisons are an important aspect of drug screening for potential anti-addiction medications. The mGluII receptor positive modulators may decrease the reinforcing effects of self-administered cocaine in rats that had extended access to cocaine, a putative model of cocaine dependence while having no effect in rats with limited access to cocaine. Positive mGluII receptor modulators may attenuate discriminatory cue-induced reinstatement of cocaine self-administration. In contrast, mGluII receptor negative modulators may reverse the reward deficits associated with early cocaine abstinence. Thus, the disclosure provides compounds and methods for treating cocaine addiction that target various aspects of cocaine dependence.

Glutamate is the principal excitatory transmitter in the central nervous system acting through ionotropic glutamate receptors. Glutamate also plays a major role in activating modulatory pathways through G-protein-coupled metabotropic glutamate receptors (mGluRs). To date eight mGuR subtypes have been identified and classified based on sequence homology, pharmacology and signal transduction. These include Group I (mGluR1 and 5), Group II (mGluR2 and 3) and Group III (mGluR4, 6, 7, and 8) receptors. The Group I receptors couple to Gaq and phospholipase C, whereas Group II and Group III mGluRs couple to Gai. A large body of in vitro and in vivo evidence suggests that specific mGluR subtypes are involved in a broad range of neuromodulatory roles in different brain circuits. Thus, specific subtypes may provide viable targets for novel treatment strategies for a range of neurological and psychiatric disorders, including anxiety, pain, Parkinson's disease, schizophrenia, cognitive disorders, depression or drug dependence including cocaine dependence.

Group II mGluRs (mGlu2 and mGlu3) are found both pre- and postsynaptically and couple to $G_i$ and $G_o$-proteins to negatively regulate the activity of adenylyl cyclase. These receptors are abundantly expressed in forebrain regions such as the cortex, hippocampus, striatum and amygdala. To date, there have been relatively few binding studies reported for mGluRs due to the lack of selective radioligands with high affinities. However, high levels of binding of Group II mGluRs have been reported in brain regions implicated in different aspects of drug abuse and dependence, including the cerebral cortex, hippocampus, striatum, amygdala, frontal cortex and nucleus accumbens. It is also well established that Group II mGluRs function as glutamate autoreceptors to modulate presynaptic glutamate release.

Due to the high level of conservation of the orthosteric (i.e. glutamate) binding site of mGluRs, it has proven difficult to develop subtype specific ligands for these receptors. As such, the most widely used orthosteric antagonists for Group II mGluRs (i.e. compounds that compete with glutamate at the glutamate binding site on the receptor), such as LY341495, show some level of activity at all mGluR subtypes. Similarly LY354740 and MGS0028 are examples of competitive mGluR2/3 agonists; that is, these are compounds which are equally potent and efficacious at both mGluR2 and mGluR3. These compounds have not advanced the field as much as could be hoped due to their inability to distinguish between the Group II mGluR subtypes. However, major advances have been made in developing highly selective antagonists of mGluR1 and mGluR5 by targeting allosteric sites on the receptor to non-competitively block receptor function. Indeed, novel potent and selective negative allosteric modulators of mGluR5 that have achieved clinical development status have been developed. The ability to achieve higher selectivity with these compounds is likely due to the fact that they bind within the seven transmembrane (TM) spanning domain of the mGluR, which is less conserved than the glutamate binding pocket. Moreover, allosteric antagonists may provide additional advantages in that their activity is not altered by the presence of competing orthosteric agonists. Research has demonstrated that the synthesis of potent and selective positive allosteric modulators of mGluR2 is achievable. These compounds have the potential to elucidate the role of mGluR2 in various physiological processes, including drug dependence.

Cocaine addiction is a chronic relapsing disorder and remains a major public health problem in the United States. The number of cases of cocaine abuse has steadily risen in the past decade. To date, a safe and effective pharmacological treatment for cocaine dependence has yet to be identified, which highlights the need to design new chemical entities that may become future novel medications for cocaine addiction. Recent evidence suggests that mGluRs play a significant role in the abuse-related effects of cocaine. For example, repeated administration of cocaine has been shown to alter the function of mGluRs, as well as their regulation by cysteine/glutamate exchange in the nucleus accumbens. These findings suggest that mGluR2 may be involved in the development of cocaine dependence and may represent a possible target for drug discovery against different aspects of cocaine abuse and dependence. There are several sources of motivation that contribute to the maintenance of cocaine abuse. These include the positive reinforcing effects of cocaine and alleviation of the negative affective aspects of cocaine withdrawal. Further, conditioned stimuli previously associated with cocaine administration may elicit conditioned "cravings" leading to the reinstatement of cocaine-seeking behavior even after a prolonged period of abstinence. Recent studies suggest that the neuronal mechanisms underlying drug self-administration are different from those mediating relapse vulnerability during abstinence, and different from those mediating the negative affects of early drug withdrawal. Therefore, it is important to explore concurrently the neurochemical mechanisms that contribute to the different aspects of cocaine dependence using animal models assessing the positive reinforcing effects of cocaine, the negative affective symptoms of early withdrawal, and cue-induced reinstatement of cocaine-seeking behavior after prolonged abstinence from drug intake. The discovery and preclinical testing of highly selective mGluII receptor modulators with good brain penetration may significantly contribute to the discovery of novel therapeutic treatments for different aspects cocaine dependence.

The intravenous drug self-administration procedure provides a reliable and robust model of human drug consumption. This procedure in animals provides a valid model of human drug abuse as studied in a controlled laboratory situation. Self-administration of drugs of abuse is thought to provide an operational measure of the rewarding effects of the drug. Increases in excitatory glutamatergic transmission are likely to contribute to the positive reinforcing properties of addictive drugs. Neurochemical studies indicate that systemic cocaine administration increase glutamate levels in the ventral tegmental area (VTA) and the nucleus accumbens, brain structures that are integral components of the extended amygdala, a brain circuit mediating the reward effects of all major drugs of abuse. Recent findings showed that the mGluR2/3 agonist LY379268 attenuated cocaine self-administration in animals with an extended history (6 hr) of daily cocaine or amphetamine self-administration. In contrast, LY379268 was ineffective in reducing cocaine self-administration in rats with short access (1 hr) to cocaine self-administration. Thus, these data suggest that neuroadaptations occur during prolonged cocaine exposure that may render a mGluR agonist, such as LY379268, effective in attenuating cocaine self-administration. Accordingly, the administration of a positive modulator of mGluII receptors may decrease cocaine self-administration in rats with extended access to cocaine by decreasing glutamate neurotransmission in limbic structures similar to the effects of mGluR2/3 agonists. In contrast, a negative modulator of mGluII receptors will most likely have no effect on cocaine self-administration, or possibly will shift the dose-response curve to the left, potentiating the reinforcing effects of cocaine.

Another challenge for the treatment of drug addiction is chronic vulnerability to relapse. One of the factors that precipitates drug craving and relapse to drug taking behavior in humans is environmental stimuli previously associated with drug-taking. These drug-associated stimuli can be divided into two categories: discrete drug cues (e.g., drug paraphernalia) that are associated with the rewarding effects of the drug, and discriminatory and contextual drug cues (e.g., specific environmental stimuli or specific environments) that predicts drug availability. In animals, discrete, discriminative and contextual conditioned cues can reinstate drug-seeking behavior, measured by variables derived from the reinstatement procedure. Recent data showed that reinstatement of cocaine-seeking was attenuated by systemic injections of N-acetylcysteine that leads to a tonic increase in nucleus accumbens glutamate levels in rats. Preliminary results in humans suggest that N-acetylcysteine attenuated cocaine craving in addicted humans. Further, exposure to environmental cues previously paired with cocaine injections increased glutamate in the nucleus accumbens. A potential use for mGluR2/3 agonists as pharmacotherapeutic agents to inhibit relapse was recently shown using different rodent models of reinstatement. Specifically, the mGluR2/3 agonist LY379268 attenuated cocaine-seeking behavior induced by discriminative cocaine-associated cues or by cocaine priming. In addition, LY379268 inhibited cue-induced reinstatement of heroin-seeking, alcohol-seeking, nicotine-seeking, and also inhibited food-seeking behavior. The decreases in cue-induced food responding suggest that the administration of mGluR2/3 agonist decreased motivation for a natural reinforcer also. Further, it has been hypothesized that susceptibility to relapse due to cue reactivity increases gradually over periods of weeks or months. Thus, the administration of a positive modulator of mGluII receptors during prolonged abstinence from cocaine self-administration will decrease, while a negative modulator of mGluII receptors will have no effect on cocaine-seeking behavior induced by discriminative stimuli associated with cocaine availability.

Avoidance and alleviation of the negative affective state of early drug withdrawal with further drug abuse is hypothesized to be an important source of motivation that contributes significantly to the development of compulsive drug use and relapse during early abstinence. It has been hypothesized that susceptibility to relapse due to affective withdrawal symptoms peaks within days of cessation reflecting early rise in withdrawal symptoms. Thus, pharmacological treatments that reverse the depression-like aspects of early cocaine withdrawal would remove an important source of motivation that contributes to relapse to drug abuse shortly after the initial cessation of drug administration. Abrupt abstinence following chronic exposure to drugs of abuse, including cocaine results in a negative affective state reflected in significant elevations in intracranial self-stimulation (ICSS) thresholds. ICSS thresholds are thought to provide an operational measure of brain reward function; thus elevations in ICSS thresholds reflect deficits in brain reward function. This threshold elevation is opposite to the lowering of ICSS thresholds observed after cocaine administration that reflects an increase in brain reward function that most likely underlies, or at least relates to, cocaine's euphorigenic effects. This increase in brain reward function associated with cocaine consumption is considered essential for the establishment and maintenance of cocaine self-administration behavior. The mechanisms that contribute to withdrawal-induced reward deficits or reward facilitation remain unclear. Group II mGluRs have been implicated in the synaptic adaptations that occur in response to chronic drug exposure and contribute to the aversive behavioral withdrawal syndrome. The mGluR2/3 agonist LY314582, was shown to elevate ICSS thresholds in control rats; and in nicotine-dependent rats at lower doses than those that elevate thresholds in control rats, suggesting that negative regulation of brain reward function by mGluR2/3 was increased by prolonged nicotine exposure. That is, activation of mGluR2/3 precipitated ICSS threshold elevations in nicotine-dependent rats similar to those threshold elevations observed during spontaneous nicotine withdrawal. The above findings led to the prediction that an antagonist of mGluR2/3 would reverse spontaneous nicotine withdrawal. Consistent with this prediction, blockade of mGluR2/3 attenuated the reward deficits exhibited by rats undergoing spontaneous nicotine withdrawal. Therefore, it was hypothesized that nicotine withdrawal is associated with decreased glutamatergic transmission in brain reward circuitries, contributing to the reward deficits observed during withdrawal. The role of glutamate transmission in the early phase of cocaine withdrawal has not been studied extensively. However, based on the above mentioned findings and the hypothesis of overlapping mechanisms of withdrawal from different drugs of abuse, one may hypothesize that decreased glutamatergic neurotransmission will also partly mediate cocaine withdrawal in cocaine-dependent subjects. Thus, based on the presynaptic localization of mGluII receptors where they suppress glutamate release, it is predicted that administration of mGluII receptor negative modulators will attenuate reward deficits of cocaine withdrawal (e.g., reverse elevations in brain reward thresholds). In contrast, administration of mGluII receptors positive modulators will result in worsening of cocaine withdrawal signs.

Schizophrenia

Schizophrenia is a devastating psychiatric illness that afflicts approximately 1% of the worldwide population. The core symptoms observed in schizophrenic patients include positive symptoms (thought disorder, delusions, hallucinations, paranoia), negative symptoms (social withdrawal, anhedonia, apathy, paucity of speech) and cognitive impairments such as deficits in perception, attention, learning, short- and long-term memory and executive function. The cognitive deficits in schizophrenia are one of the major disabilities associated with the illness and are considered a reliable predictor of long-term disability and treatment outcome. Currently available antipsychotics effectively treat the positive symptoms, but provide modest effects on the negative symptoms and cognitive impairments. Furthermore, some patients are unresponsive to current antipsychotic treatments and several of these agents are associated with adverse side effects, including disturbances in motor function, weight gain, and sexual dysfunction. Thus, there is a need for new treatment strategies for schizophrenia that provide major improvements in efficacy across multiple symptom clusters and have fewer adverse effects.

A major challenge in developing novel therapeutic approaches for treatment of schizophrenia is the absence of clear molecular or cellular neuropathological changes responsible for this disorder. Until recently, the dominant hypothesis has been that excessive dopaminergic transmission in the forebrain is a key causative factor for the pathophysiology underlying schizophrenia. This hypothesis is based primarily on the observation that clinically effective antipsychotic drugs have substantial antagonist activity at dopamine D2 receptors, and that the therapeutic efficacy of these compounds is highly correlated with their affinity for striatal D2 receptors. In addition, the psychotomimetic properties of indirect dopamine agonists and alterations in striatal dopamine release in schizophrenic patients support the involvement of dopamine in the pathophysiology of schizophrenia. Although compelling, the limitations in efficacy and adverse effects of currently available antipsychotics have led researchers to look for additional neurochemical or neurophysiological alterations that might contribute to the pathophysiology of this disorder.

Although the underlying pathophysiology of schizophrenia remains unknown, accumulating evidence points to disruptions in multiple neurotransmitter systems that modulate neural circuits important for normal affect, sensory processing, and cognition. In particular, early clinical findings demonstrated that changes in glutamatergic transmission produced by antagonists of the N-methyl-D-aspartate (NMDA) subtype of ionotropic glutamate receptors, including phencyclidine (PCP), result in a state of psychosis in humans that is similar to that observed in schizophrenic patients. These studies suggest that agents that increase NMDA receptor function have potential as therapeutics for the treatment of all major symptom clusters (positive, negative, cognitive) of the disease. More recently, studies indicate that reduced NMDA receptor function induces complex changes in transmission through cortical and subcortical circuits that involve both glutamatergic and GABAergic synapses and include downstream increases in transmission at glutamatergic synapses in the prefrontal cortex. Importantly, these circuit changes might share common features with changes in brain circuit activities that occur in schizophrenia patients. One hypothesis is that NMDA receptors involved in these symptoms might reside at glutamatergic synapses on GABAergic projection neurons in midbrain regions as well as GABAergic interneurons and glutamatergic projection neurons in key cortical and limbic regions For example, under normal conditions the activation of NMDA receptors localized on GABAergic projection neurons in subcortical regions, such as the nucleus accumbens, provides inhibitory control on excitatory glutamatergic thalamocortical neurons that project to pyramidal neurons in the prefrontal cortex (PFC). Hypofunction or blockade of these NMDA receptors on midbrain inhibitory GABAergic neurons could result in a disinhibition of glutamatergic thalamocortical inputs to pyramidal neurons in the PFC. This disinhibition would lead to a subsequent increased activity of glutamatergic thalamic neurons and increased activity mediated by the DL-a-amino-3-hydroxy-5-methylisoxasole-4-propionate (AMPA) subtype of glutamate receptors at thalamocortical synapses in the PFC. Based on this model, manipulations that enhance NMDA receptor function, such as activation of metabotropic glutamate receptor subtype 5 (mGluR5) located on GABAergic neurons, have potential as a novel approach to the treatment of schizophrenia. An alternative approach might be to reduce excitatory glutamatergic transmission at key synapses, such as thalamocortical synapses in the PFC, by activation of metabotropic glutamate receptor subtypes 2 and 3 (mGluR 2 and mGluR3) presynaptically located in these synapses. Although other viable models of circuit changes associated with schizophrenia exist, this hypothesis provides one possible framework within which to consider effects of ligands at mGlu receptors that might be relevant to schizophrenia.

Group II mGlu Receptor Agonists and mGluII Receptor PAMs for Treatment of Schizophrenia A large number of preclinical and clinical studies provide strong evidence that agonists of mGluR2 and mGluR3 (group II mGlu receptors) also have potential as a novel approach to the treatment of schizophrenia. Group II mGlu receptor agonists such as (1S,2S,5R,6S)-2-aminobicyclo[3.1.0]hexane-2,6-dicarboxylic acid (LY354740) and related compounds that are highly selective for mGluR2 and mGluR3 have robust activity in animal models that have been used to predict efficacy of potential antipsychotic agents. Consistent with the animal studies, clinical studies reveal that a highly selective agonist of group II mGlu receptors has robust efficacy in improving ratings for positive and negative symptoms in patients with schizophrenia. Unlike currently marketed antipsychotic agents, there were no major adverse events reported for the mGluR2/3 agonist in the clinical studies to date. However, further clinical studies will be required to fully establish safety of these compounds after long-term dosing in schizophrenic patients, as well as assess possible efficacy on the cognitive impairments in these patients. Taken together, these findings represent an important breakthrough and could ultimately lead to introduction of group II mGlu receptor activators as a fundamentally novel approach to the treatment of schizophrenia. As mentioned above, animal studies reveal that the psychotomimetic agents increase activity of glutamatergic synapses in the PFC, and hyperactivity of glutamate neurotransmission in the PFC and limbic structures has been postulated to play a critical role in the pathophysiology of schizophrenia. Interestingly, effects of psychotomimetic agents on glutamatergic transmission in the PFC are blocked by group II mGlu receptor agonists. Although it is not yet clear whether this action of group II mGlu receptor agonists is mechanistically related to the antipsychotic actions of these compounds, these actions fit well with current models of disruptions in subcortical and cortical circuits that might be involved in the psychotomimetic effects of NMDA receptor antagonists and the range of symptoms observed in schizophrenia patients. Despite advances in development of group II mGlu receptor agonists, it is not yet clear whether orthosteric agonists of these receptors will reach the market for broad clinical use. To date, the discovery and development of mGluR2/3 agonists have been accomplished with one major chemical scaffold, and it is unlikely that further improvements involving a significant departure from the structures of these compounds will be possible. Moreover, long-term administration of group II mGlu receptor agonists induces robust tolerance in at least one rodent model that has been used to predict antipsychotic efficacy. These orthosteric agonists also activate both mGluR2 and mGluR3 and do not provide insights into which of these group II mGlu receptor subtypes is most important for clinical efficacy. Although, recent findings demonstrate that the antipsychotic-like effects of mGlu2/3 receptor agonists, such as LY404039 [4-aminho-2-thiabicyclo(3.1.0)hexane-4,6-dicarboxylic acid] are absent in mGluR2-knockout, but not mGluR3-knockout, mice. Thus, it is possible that positive allosteric modulators of mGluR2 might be an alternative approach that could provide greater selectivity and other potential advantages to orthosteric agonists.

Multiple novel compounds have now been identified that act as allosteric potentiators of mGluR2. Most of these novel molecules are structurally related to two prototypical mGluR2 PAMs, termed LY487379 {2,3,2-trifluoro-N-[4-(2-methoxyphenoxy)phenyl]-N-(pyridine-3-ylmethyl)ethanesulfonamide} and 4-[(2-cyclopentyl-6,7-dimethyl-1-oxo-2,3-dihydro-1H-inden-5-yloxy)methyl]biphenyl-4-carboxylic acid (biphenyl-indanone A (BINA)). These compounds are highly selective for mGluR2 and do not potentiate responses to activation of mGluR3 or other mGlu receptor subtypes. In most systems, these compounds have no agonist activity at mGluR2 but induce a leftward shift of the concentration-response curve to glutamate. Mutation analysis has identified three amino acids in the 7™ domain that are critical for actions of mGluR2 PAMs. The mGluR2 PAMs have robust effects in potentiating responses to group II mGlu receptor agonists at several identified synapses glutamatergic synapses, including excitatory synaptic responses in the PFC that are thought to be relevant to actions of psychotomimetic agents. Furthermore, multiple structurally distinct mGluR2-selective PAMs have efficacy in animal models that predict antipsychotic activity that are very similar to those observed with the mGluR2/3 orthosteric agonists. Taken together with the clinical studies establishing efficacy of group II mGlu receptor agonists in the treatment of schizophrenia, these studies raise the possibility that selective mGluR2 PAMs might provide a novel approach to the treatment of these disorders that is devoid of the adverse effects associated with currently available drugs.

EXAMPLES

The following examples are intended to illustrate but not limit the disclosed embodiments.

Example 1

General Synthetic Scheme for the Preparation of Isoindolinone Derivatives

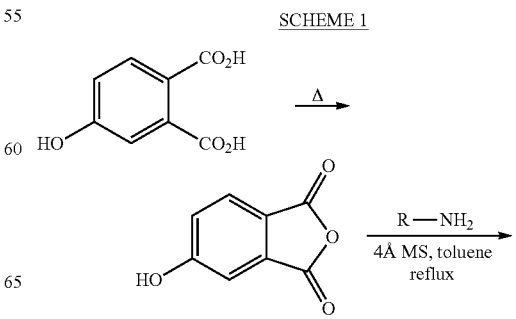

SCHEME 1

-continued

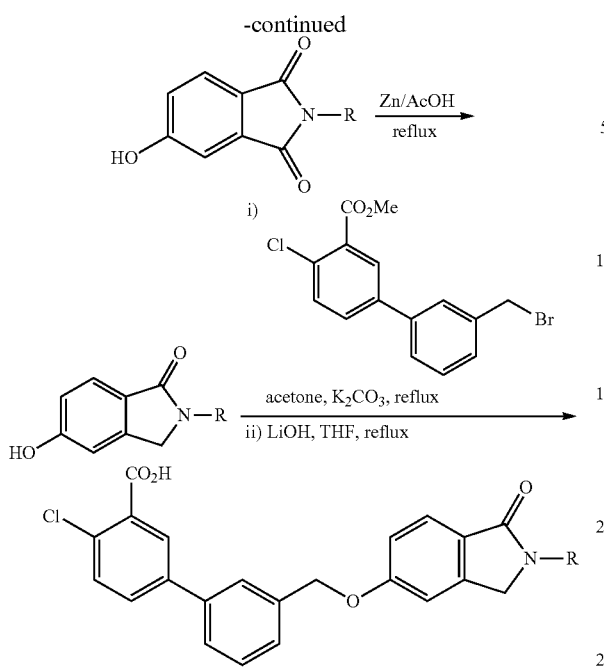

Example 2

Preparation of Methyl-3-(bromomethyl)-4-chlorobiphenyl-3-carboxylate

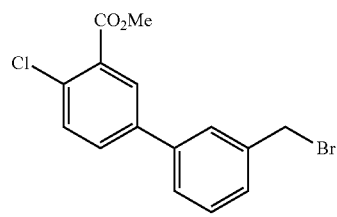 [SMILES: COC(=O)c1cc(-c2cccc(CBr)c2)ccc1Cl]

2-Chloro-5-iodobenzoic acid (2.00 g, 7.08 mmol), m-tolylboronic acid (1.15 g, 8.50 mmol), Na$_2$CO$_3$ (2.70 g, 25.5 mmol) and Pd(OAc)$_2$ (94 mg, 0.42 mmol) were dissolved in water (9 mL) and heated at 50° C. for 2 hours. The mixture was filtered and washed with water and filtrate was acidified with 2.5 M HCl, extracted into ethyl acetate and dried over anhydrous Na$_2$SO$_4$, the solvent was evaporated in vacuo to obtain crude 4-chloro-3'-methylbiphenyl-3-carboxylic acid as a grey solid in quantitative yield. $^1$H NMR (300 MHz, DMSO-d$_6$): δ 8.03 (s, 1H), 7.83 (d, J=8.1 Hz, 1H), 7.63 (d, J=7.8 Hz, 1H), 7.55-7.50 (m, 2H), 7.40 (t, J=7.8 Hz, 1H), 7.25 (d, J=6.6 Hz, 1H), 2.41 (s, 3H).

A mixture of 4-chloro-3'-methylbiphenyl-3-carboxylic acid (1.70 g, 6.90 mmol), K$_2$CO$_3$ (7.0 g, 50.6 mmol) and CH$_3$I (3 mL, 48 mmol) in acetone (30 mL) was heated under reflux for 1 h. After filtration and evaporation of excess CH$_3$I, the residue was washed with water and extracted with ethyl acetate, dried over anhydrous Na$_2$SO$_4$, and evaporated solvent in vacuo to provide crude methyl 4-chloro-3'-methylbiphenyl-3-carboxylate (1.77 g, 98%) as a brown oil. $^1$H NMR (300 MHz, DMSO-d$_6$): δ 8.04 (s, 1H), 7.85 (d, J=7.8 Hz, 1H), 7.64 (d, J=8.1 Hz, 1H), 7.52-7.47 (m, 2H), 7.38 (t, J=7.8 Hz, 1H), 7.23 (d, J=7.5 Hz, 1H), 3.90 (s, 3H), 2.39 (s, 3H).

Methyl 4-chloro-3'-methylbiphenyl-3-carboxylate (1.77 g, 6.5 mmol) and NBS (1.27 g, 7.19 mmol) were dissolved in CCl$_4$ (20 mL), a catalytic amount of AIBN was added and the mixture was heated at reflux overnight. The reaction mixture was filtered, the solvent was removed in vacuo and the residue was purified using automated medium pressure silica gel chromatography (ISCO) eluting with 20% ethyl acetate/hexane to obtain methyl 3'-(bromo-methyl)-4-chlorobiphenyl-3-carboxylate (2.10 g, 91%) as a pale brown solid. $^1$H NMR (300 MHz, CDCl$_3$): δ 8.07 (s, 1H), 7.68-7.45 (m, 6H), 4.58 (s, 2H), 4.00 (s, 3H).

Example 3

Preparation of 5-Hydroxyisobenzofuran-1,3-dione

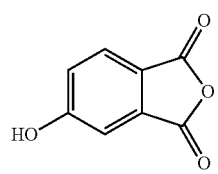 [SMILES: O=C1OC(=O)c2cc(O)ccc21]

4-Hydroxy-phthalic acid (10 g, 54.9 mmol) was heated at 200° C. over night. The resulting material was cooled and washed with ethyl acetate to obtain 4-hydroxy-phthalic anhydride as a white solid in quantitative yield.

Example 4

Preparation of 2-Cyclopentyl-5-hydroxyisoindoline-1,3-dione

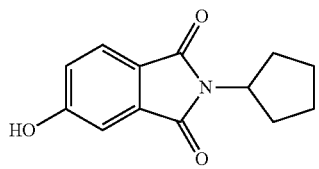 [SMILES: O=C1c2ccc(O)cc2C(=O)N1C1CCCC1]

4-Hydroxy-phthalic anhydride (5.4 g, 32.9 mmol), cyclopentyl amine (4.9 mL, 49.6 mmol) and 4 Å molecular sieves in toluene (136 mL) were stirred at reflux overnight. The reaction mixture was filtered and the solvent was evaporated in vacuo to obtain the product (6.1 g, 80%) as a yellow solid. $^1$H NMR (300 MHz, DMSO-d$_6$): δ 7.60 (d, J=7.8 Hz, 1H), 7.05-7.01 (m, 2H), 4.50-4.40 (m, 1H), 1.97-1.52 (m, 8H).

Example 5

Preparation of 2-Cyclopentyl-5-hydroxyisoindolin-1-one

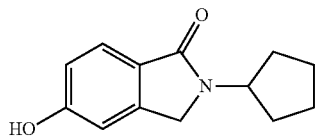 [SMILES: O=C1c2ccc(O)cc2CN1C1CCCC1]

To a solution of 2-cyclopentyl-5-hydroxyisoindoline-1,3-dione (4.1 g, 18.0 mmol), in CH$_3$CO$_2$H (129 mL), Zn dust (11.6 g, 180 mmol) was added and the mixture heated at reflux for 5 min. The volatiles were removed in vacuo and the residue was dissolved in water and extracted with ethyl acetate. The crude residue was purified using automated prep-HPLC to yield the desired compound (1.7 g, 44%) as a white solid. ¹HNMR (400 MHz, DMSO-d₆): 10.10 (bs, 1H), 7.44 (d, J=8.5 Hz, 1H), 6.89 (s, 1H), 6.83 (d, J=7.9 Hz, 1H), 4.52-4.48 (m, 1H), 4.31 (s, 2H), 1.83-1.57 (m, 8H). LCMS calcd for $C_{13}H_{15}NO_2$ [M+H]⁺ 218 found: 218.

Example 6

Preparation of 4-Chloro-3'-((2-cyclopentyl-1-oxoisoindolin-5-yloxy)-methyl)biphenyl-3-carboxylic acid

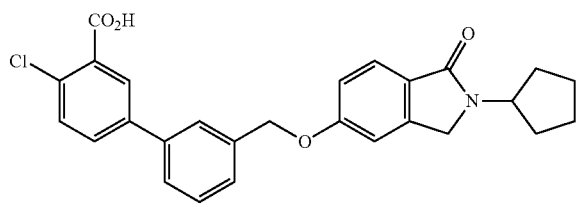 [SMILES: O=C(O)c1cc(-c2cccc(COc3ccc4c(c3)CN(C3CCCC3)C4=O)c2)ccc1Cl]

To a solution of 2-cyclopentyl-5-hydroxyisoindolin-1-one (50 mg, 0.23 mmol) in acetone (15 mL), K₂CO₃ (181 mg, 1.31 mmol) was added methyl 3'-(bromo-methyl)-4-chloro-biphenyl-3-carboxylate (92 mg, 0.27 mmol) and the mixture was heated at reflux for 1 h. The reaction mixture was filtered and the solvent was evaporated in vacuo to obtain methyl 4-chloro-3'-((2-cyclopentyl-1-oxoisoindolin-5-yloxy)methyl)biphenyl-3-carboxylate as a yellow oil.

Crude methyl 4-chloro-3'-((2-cyclopentyl-1-oxoisoindolin-5-yloxy)methyl)biphenyl-3-carboxylate (109 mg, 0.23 mmol) was dissolved in tetrahydrofuran (17 mL) and 2M LiOH (0.57 mL, 1.15 mmol) was added and the mixture was heated at reflux for 3 h. The solvent was evaporated and the residue was dissolved in water and neutralized using 2M HCl. The aqueous layer was extracted with ethyl acetate and the organic layer was dried over anhydrous Na₂SO₄. The solvent was evaporated in vacuo to obtain the crude acid as a yellow solid. The crude residue was purified using automated prep-HPLC to yield the desired compound (48 mg, 46%) as a white solid. ¹H NMR (400 MHz, CDCl₃): δ 8.18 (s, 1H), 7.78 (d, J=8.5 Hz, 1H), 7.65-7.41 (m, 6H), 7.05 (d, J=8.5 Hz, 1H), 6.99 (s, 1H), 5.16 (s, 2H), 4.74 (m, 1H), 4.30 (s, 2H), 1.97 (m, 2H), 1.76-1.59 (m, 6H). HRMS: calcd. for $C_{27}H_{24}ClNO_4$ [M+H]⁺ 462.1467; found 462.1468.

In a similar manner to the procedure described for Example 5 the following compounds were prepared.

Example 7

Preparation of 4-Chloro-3'-((2-(cyclopropylmethyl)-1-oxoisoindolin-5-yloxy)methyl)biphenyl-3-carboxylic acid

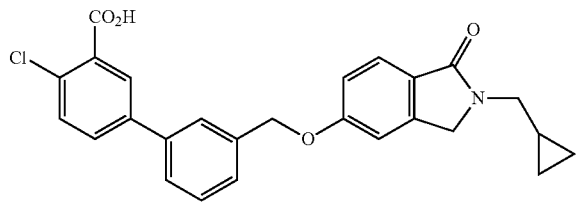 [SMILES: O=C(O)c1cc(-c2cccc(COc3ccc4c(c3)CN(CC3CC3)C4=O)c2)ccc1Cl]

White solid (49 mg, 39%). ¹H NMR (300 MHz, DMSO-d₆): δ 8.07 (s, 1H), 7.88-7.84 (m, 2H), 7.71-7.52 (m, 5H), 7.28 (s, 1H), 7.14 (d, J=8.4 Hz, 1H), 5.28 (s, 2H), 4.50 (s, 2H), 3.33 (d, J=7.5 Hz 2H), 1.06-0.98 (m, 1H), 0.51-0.48 (m, 2H), 0.31-0.28 (m, 2H). HRMS: calcd. for $C_{26}H_{22}ClNO_4$ [M+H]⁺ 448.131; found 448.1313.

Example 8

Preparation of 4-Chloro-3'-((2-isobutyl-1-oxoisoindolin-5-yloxy)methyl)-biphenyl-3-carboxylic acid

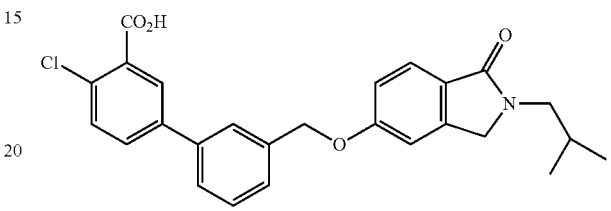

White solid (75 mg, 34%). ¹H NMR (400 MHz, CDCl₃): δ 8.17 (s, 1H), 7.78 (d, J=8.5 Hz, 1H), 7.66-7.62 (m, 2H), 7.55-7.41 (m, 4H), 7.07-7.05 (m, 1H), 7.00 (s, 1H), 5.17 (s, 2H), 4.33 (s, 2H), 3.39 (d, J=7.3 Hz, 2H), 2.07-1.96 (m, 1H), 0.92 (d, J=6.7 Hz, 6H). HRMS: calcd. for $C_{26}H_{24}ClNO_4$ [M+H]⁺ 450.1467; found 450.1472.

Example 9

Preparation of 4-Chloro-3'-((2-isopentyl-1-oxoisoindolin-5-yloxy)methyl)biphenyl-3-carboxylic acid

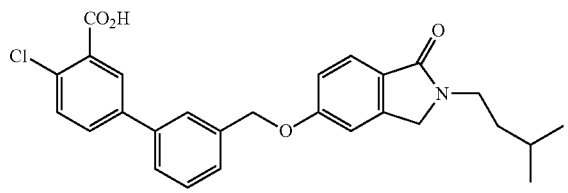 [SMILES: CC(C)CCN1Cc2cc(OCc3cccc(-c4ccc(Cl)c(C(=O)O)c4)c3)ccc2C1=O]

White solid (82 mg, 41%). ¹H NMR (400 MHz, CDCl₃): δ 8.18 (s, 1H), 7.78 (d, J=8.5 Hz, 1H), 7.66-7.62 (m, 2H), 7.55-7.42 (m, 4H), 7.06 (dd, J=8.5, 1.8 Hz, 1H), 6.99 (s, 1H), 5.17 (s, 2H), 4.31 (s, 2H), 3.62-3.58 (m, 2H), 1.63-1.49 (m, 3H), 0.93 (d, J=6.1 Hz, 6H). HRMS: calcd. for $C_{27}H_{26}ClNO_4$ [M+H]⁺ 464.1623; found 464.1626.

Example 10

Preparation of 4-Chloro-3'-((1-oxo-2-phenylisoindolin-5-yloxy)methyl)biphenyl-3-carboxylic acid

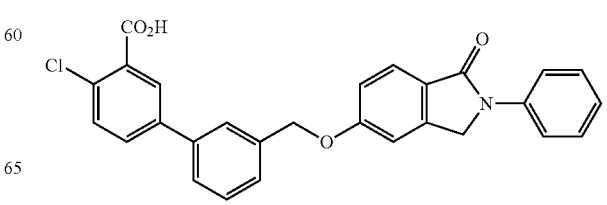

White solid (28 mg, 36%). $^1$H NMR (400 MHz, CDCl$_3$): δ 8.20 (s, 1H), 7.86-7.36 (m, 11H), 7.15-7.05 (m, 3H), 5.19 (s, 2H), 4.77 (s, 2H). HRMS: calcd. for C$_{28}$H$_{20}$ClNO$_4$ [M+H]$^+$ 470.1154; found 470.1157.

Example 11

Preparation 4-Chloro-3'-((2-cyclohexyl-1-oxoisoindolin-5-yloxy)methyl)biphenyl-3-carboxylic acid

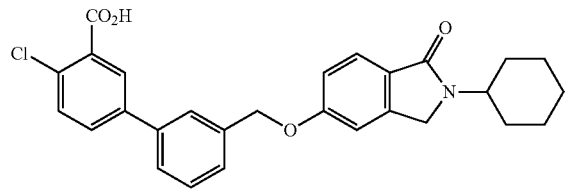 [SMILES: O=C(O)c1cc(-c2cccc(COc3ccc4c(c3)CN(C3CCCCC3)C4=O)c2)ccc1Cl]

White solid (87 mg, 36%). $^1$H NMR (300 MHz, DMSO-d$_6$): δ 8.05 (s, 1H), 7.83 (m, 2H), 7.68-7.45 (m, 5H), 7.24 (s, 1H), 7.12 (d, J=8.4 Hz, 1H), 5.27 (s, 2H), 4.36 (s, 2H), 3.99-3.92 (m, 1H), 1.79-1.14 (m, 10H). HRMS: calcd. for C$_{28}$H$_{26}$ClNO$_4$ [M+H]$^+$ 476.1623; found 476.1621.

Example 12

Preparation of 4-Chloro-3'-((2-cyclopropyl-1-oxoisoindolin-5-yloxy)methyl)biphenyl-3-carboxylic acid

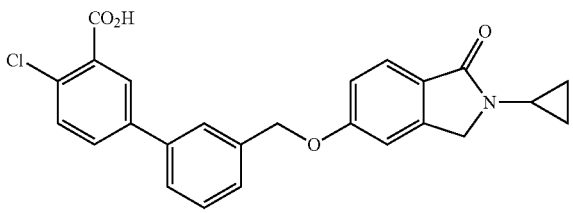

White solid (78 mg, 23%). $^1$HNMR (300 MHz, DMSO-d$_6$): δ 8.05 (s, 1H), 7.86-7.81 (m, 2H), 7.67-7.51 (m, 5H), 7.21 (s, 1H), 7.12 (d, J=7.8 Hz, 1H), 5.26 (s, 2H), 4.32 (s, 2H), 2.92-2.86 (m, 1H), 0.80-0.76 (m, 4H). HRMS: calcd. for C$_{25}$H$_{20}$ClNO$_4$ [M+H]$^+$ 434.1154; found 434.1150.

Example 13

Preparation of 4-Chloro-3'-((2-cyclobutyl-1-oxoisoindolin-5-yloxy)methyl)biphenyl-3-carboxylic acid

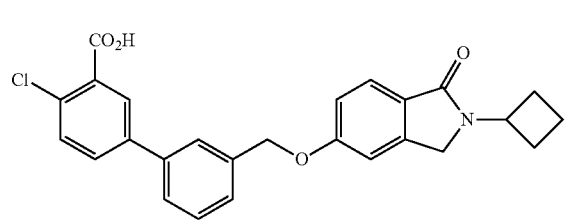 [SMILES: O=C(O)c1cc(-c2cccc(COc3ccc4c(c3)CN(C3CCC3)C4=O)c2)ccc1Cl]

White solid (183 mg, 41%). $^1$H NMR (300 MHz, DMSO-d$_6$): δ 8.05 (s, 1H), 7.85-7.83 (m, 2H), 7.68-7.51 (m, 5H), 7.25 (s, 1H), 7.12 (d, J=8.7 Hz, 1H), 5.27 (s, 2H), 4.78-4.62 (m, 1H), 4.49 (s, 2H), 2.38-2.22 (m, 2H), 2.15-2.09 (m, 2H), 1.78-1.66 (m, 2H). HRMS: calcd. for C$_{26}$H$_{22}$ClNO$_4$ [M+H]$^+$ 448.131; found 448.131.

Example 14

Preparation of 4-Chloro-3'-((2-isopropyl-1-oxoisoindolin-5-yloxy)methyl)biphenyl-3-carboxylic acid

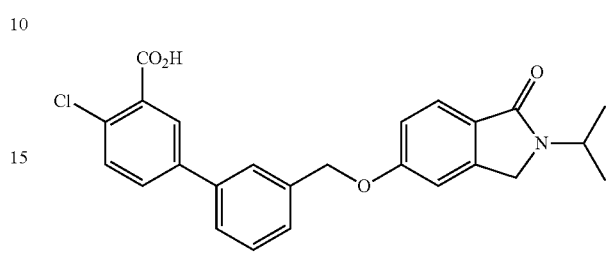

White solid (14 mg, 32%). $^1$H NMR (300 MHz, DMSO-d$_6$): δ 8.06 (s, 1H), 7.85-7.82 (m, 2H), 7.68-7.51 (m, 5H), 7.24 (s, 1H), 7.13 (d, J=8.4 Hz, 1H), 5.26 (s, 2H), 4.45-4.40 (m, 1H), 4.34 (s, 2H), 1.19 (d, J=6.9 Hz, 6H). HRMS: calcd. for C$_{25}$H$_{22}$ClNO$_4$ [M+H]$^+$ 436.131; found 436.1309.

Example 15

Preparation of 4-Chloro-3'-((1-oxo-2-propylisoindolin-5-yloxy)methyl)biphenyl-3-carboxylic acid

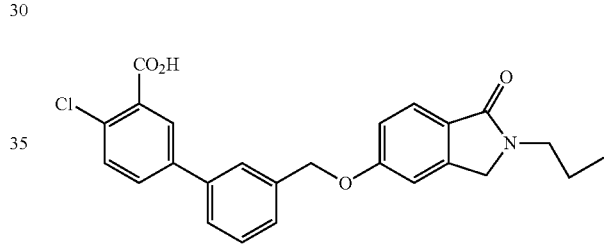

White solid (30 mg, 34%). $^1$H NMR (400 MHz, CDCl$_3$): δ 8.18 (s, 1H), 7.78 (d, J=8.5 Hz, 1H), 7.65-7.62 (m, 2H), 7.53-7.43 (m, 4H), 7.06 (dd, J=8.5 Hz, J=2.4 Hz, 1H), 6.99 (s, 1H), 5.17 (s, 2H), 4.31 (s, 2H), 3.54 (t, J=7.3 Hz, 2H), 1.70-1.61 (m, 2H), 0.93 (t, J=7.3 Hz, 3H). HRMS: calcd. for C$_{25}$H$_{22}$ClNO$_4$ [M+H]$^+$ 436.131; found 436.1315.

Example 16

Preparation of 4-Chloro-3'-((1-oxo-2-(4-trifluoromethoxy)benzyl) isoindolin-5-yloxy)methyl)biphenyl-3-carboxylic acid

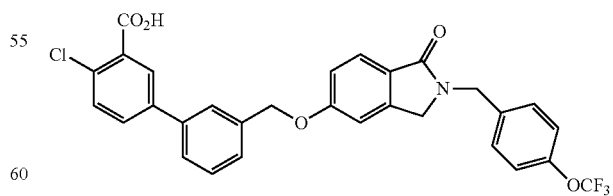

White solid (12 mg, 30%). $^1$H NMR (400 MHz, CDCl$_3$): δ 8.13 (s, 1H), 7.80 (d, J=8.5 Hz, 1H), 7.62-7.28 (m, 8H), 7.14 (d, J=7.9 Hz, 2H), 7.07-7.05 (m, 1H), 6.93 (s, 1H), 5.14 (s, 2H), 4.74 (s, 2H), 4.20 (s, 2H). HRMS: calcd. for C$_{30}$H$_{21}$ClF$_3$NO$_5$ [M+H]$^+$ 568.1133; found 568.1136.

Example 17

Preparation of 4-Chloro-3'-((2-(cyclohexylmethyl)-1-oxoisoindolin-5-yloxy)methyl)biphenyl-3-carboxylic acid

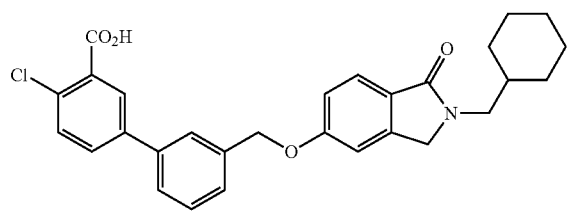 [SMILES: O=C(O)c1cc(-c2cccc(COc3ccc4c(c3)CN(CC3CCCCC3)C4=O)c2)ccc1Cl]

Pale yellow solid (29.1 mg, 32%). $^1$H NMR (400 MHz, DMSO-d$_6$): δ 7.98 (d, J=2.8 Hz, 1H), 7.79-7.77 (m, 2H), 7.64-7.46 (m, 5H), 7.20 (d, J=1.8 Hz, 1H), 7.09-7.06 (m, 1H), 5.22 (s, 2H), 4.34 (s, 2H), 3.27 (d, J=7.3 Hz, 2H), 1.63-1.52 (m, 6H), 1.16-0.82 (m, 5H). LRMS calcd. for C$_{29}$H$_{28}$ClNO$_4$ [M+H]$^+$ 490 found: 490.

Example 18

General Alternative Synthetic Scheme for the Synthesis of Isoindolinone Analogues

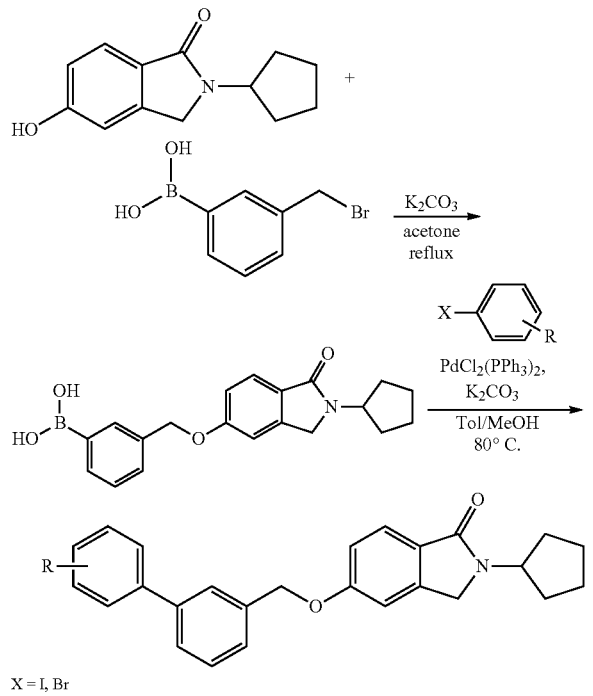

X = I, Br

Example 19

Preparation of 3-((2-Cyclopentyl-1-oxoisoindolin-5-yloxy)methyl)phenylboronic acid To a solution of 2-cyclopentyl-5-hydroxyisoindolin-1-one (500 mg, 2.3 mmol) in acetone (20 mL), K$_2$CO$_3$ (1.2 g, 8.7 mmol) and 3-(bromomethyl)phenylboronic acid (650 mg, 3.0 mmol) were added and refluxed for 3 h. The reaction mixture was filtered and solvent was evaporated in vacuo to obtain 3-((2-cyclopentyl-1-oxoisoindolin-5-yloxy)methyl)phenylboronic acid as a white solid (582.7 mg, 72%). The crude product was used for the next step without further purification. $^1$H NMR (400 MHz, DMSO-d$_6$): δ 7.86 (s, 1H), 7.75-7.69 (m, 2H), 7.55-7.32 (m, 4H), 7.19 (s, 1H), 7.09-7.07 (m, 1H), 5.15 (s, 2H), 4.55-4.49 (m, 1H), 4.37 (s, 2H), 1.84-1.56 (m, 8H). LRMS calcd. for C$_{20}$H$_{22}$BNO$_4$ [M+H]$^+$ 352 found: 352.

Example 20

Preparation of 3'-((2-Cyclopentyl-1-oxoisoindolin-5-yloxy)methyl)-6-methoxybiphenyl-3-carboxylic acid

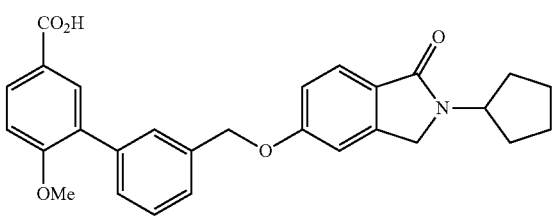 [SMILES: COc1ccc(C(=O)O)cc1-c1cccc(COc2ccc3c(c2)CN(C2CCCC2)C3=O)c1]

3-((2-Cyclopentyl-1-oxoisoindolin-5-yloxy)methyl)phenylboronic acid (30 mg, 0.08 mmol), 3-iodo-4-methoxybenzoic acid (19.7 mg, 0.07 mmol), K$_2$CO$_3$ (29 mg, 0.21 mmol) and PdCl$_2$(PPh$_3$)$_2$ (6.2 mg, 0.009 mmol) were dissolved in a mixture of toluene-MeOH (1.1 mL:0.1 mL) and heated at 80° C. for 1.5 hours. The mixture was filtered through celite washed with water and solvent was removed was evaporated in vacuo. The resulted crude material was acidified with 2 M HCl, extracted into EtOAc and dried over anhyd. Na$_2$SO$_4$, evaporated solvent in vacuo to obtain the crude acid which was purified using automated prep-HPLC to yield the desired compound 4.2 mg, 13%) as a white solid. $^1$H NMR (400 MHz, DMSO-d$_6$): δ 7.93 (d, J=8.2 Hz, 1H), 7.82 (s, 1H), 7.55-7.42 (m, 5H), 7.21-7.18 (m, 2H), 7.10 (dd, J=8.7 Hz, J=2.3 Hz, 1H), 5.23 (s, 2H), 4.54-4.46 (m, 1H), 4.37 (s, 2H), 3.84 (s, 3H), 1.85-1.80 (m, 2H), 1.71-1.56 (m, 6H). LRMS calcd. for C$_{28}$H$_{27}$NO$_5$ [M+H]$^+$ 458 found: 458.

In a similar manner the following compounds were synthesized using the appropriate starting material.

Example 21

Preparation of 3'-((2-Cyclopentyl-1-oxoisoindolin-5-yloxy)methyl)-2,6-dimethoxybiphenyl-4-carboxylic acid

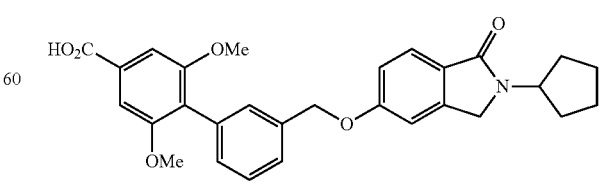

White solid (8 mg, 16%). $^1$H NMR (400 MHz, DMSO-d$_6$): δ 7.55 (d, J=8.2 Hz, 1H), 7.40-7.09 (m, 8H), 5.19 (s, 2H), 4.56-4.48 (m, 1H), 4.39 (s, 2H), 3.69 (s, 6H), 2.02-1.54 (m, 8H). LRMS calcd. for $C_{29}H_{29}NO_6$ [M+H]$^+$ 488 found: 488.

Example 22

Preparation of 3'-((2-Cyclopentyl-1-oxoisoindolin-5-yloxy)methyl)-4-hydroxybiphenyl-3-carboxylic acid

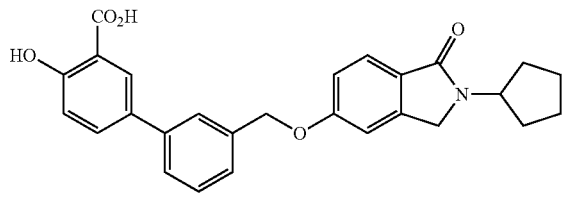 [SMILES: O=C(O)c1cc(-c2cccc(COc3ccc4c(c3)CN(C3CCCC3)C4=O)c2)ccc1O]

White solid (18 mg, 20%). $^1$H NMR (400 MHz, CDCl$_3$): δ 10.96 (s, 1H), 8.08 (s, 1H), 7.78-7.34 (m, 6H), 7.08-7.01 (m, 3H), 5.18 (s, 2H), 4.80-4.71 (m, 1H), 4.31 (s, 2H), 1.99-1.56 (m, 8H). LRMS calcd. for $C_{27}H_{25}NO_5$ [M+H]$^+$ 444 found: 444.

Example 23

Preparation of 6-Chloro-3'-((2-cyclopentyl-1-oxoisoindolin-5-yloxy)methyl)biphenyl-3-carboxylic acid

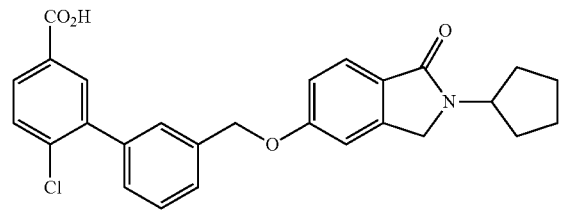 [SMILES: O=C(O)c1ccc(Cl)c(-c2cccc(COc3ccc4c(c3)CN(C3CCCC3)C4=O)c2)c1]

White solid (8.2 mg, 14%). $^1$H NMR (400 MHz, CDCl$_3$): δ 8.05 (s, 1H), 7.99-7.97 (m, 1H), 7.75 (d, J=8.2 Hz, 1H), 7.55-7.41 (m, 5H), 7.06-7.04 (m, 1H), 6.99 (s, 1H), 5.17 (s, 2H), 4.77-4.69 (m, 1H), 4.28 (s, 2H), 1.99-1.55 (m, 8H). LRMS calcd. for $C_{27}H_{24}ClNO_4$ [M+H]$^+$ 462 found: 462.

Example 24

Preparation of 2-Chloro-3'-((2-cyclopentyl-1-oxoisoindolin-5-yloxy)methyl)biphenyl-4-carboxylic acid

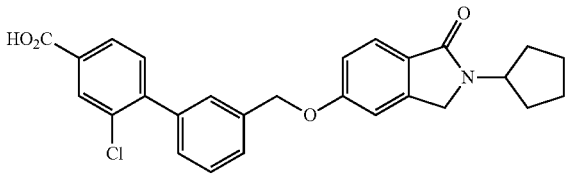 [SMILES: O=C(O)c1ccc(-c2cccc(COc3ccc4c(c3)CN(C3CCCC3)C4=O)c2)c(Cl)c1]

White solid (13.8 mg, 15%). $^1$H NMR (400 MHz, DMSO-d$_6$): δ 8.00 (s, 1H), 7.94-7.91 (m, 1H), 7.55-7.51 (m, 5H), 7.45-7.43 (m, 1H), 7.21-7.09 (m, 2H), 5.25 (s, 2H), 4.55-4.47 (m, 1H), 4.37 (s, 2H), 1.86-1.56 (m, 8H). LRMS calcd. for $C_{27}H_{24}ClNO_4$ [M+H]$^+$ 462 found: 462.

Example 25

Preparation of 3'-((2-Cyclopentyl-1-oxoisoindolin-5-yloxy)methyl)-6-methylbiphenyl-3-carboxylic acid

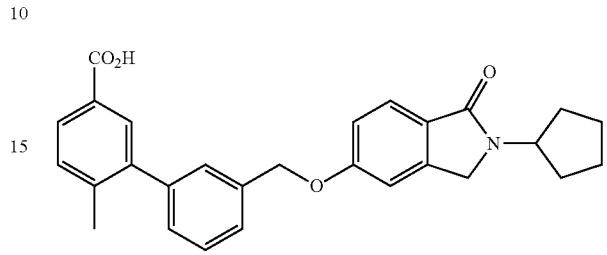

White solid (14.8 mg, 32%). $^1$HNMR (400 MHz, CDCl$_3$): δ 7.84-7.80 (m, 2H), 7.60-7.25 (m, 6H), 7.07-7.02 (m, 2H), 5.17 (s, 2H), 4.64-4.57 (m, 1H), 4.31 (s, 2H), 2.26 (s, 3H), 1.91-1.62 (m, 8H). LRMS calcd. for $C_{28}H_{27}NO_4$ [M+H]$^+$ 442 found: 442.

Example 26

Preparation of 3'-((2-Cyclopentyl-1-oxoisoindolin-5-yloxy)methyl)-5-fluorobiphenyl-3-carboxylic acid

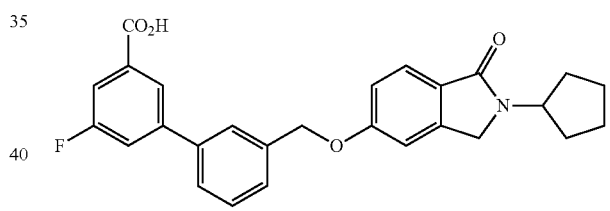

White solid (8.8 mg, 27%). $^1$H NMR (400 MHz, DMSO-d$_6$): δ 8.05 (s, 1H), 7.85-7.51 (m, 7H), 7.24-7.11 (m, 2H), 5.28 (s, 2H), 4.56-4.48 (m, 1H), 4.39 (s, 2H), 1.87-1.57 (m, 8H). LRMS calcd. for $C_{27}H_{24}FNO_4$ [M+H]$^+$ 446 found: 446.

Example 27

Preparation of 3'-((2-Cyclopentyl-1-oxoisoindolin-5-yloxy)methyl)-4-methoxybiphenyl-3-carboxylic acid

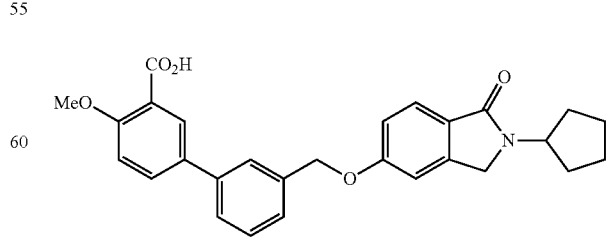

White solid (12.3 mg, 21%). $^1$H NMR (400 MHz, CDCl$_3$): δ 8.45 (s, 1H), 7.81-7.39 (m, 7H), 7.15-7.01 (m, 2H), 5.17 (s, 2H), 4.76-4.70 (m, 1H), 4.29 (s, 2H), 4.12 (s, 3H), 1.99-1.57 (m, 8H). LRMS calcd. for $C_{28}H_{27}NO_5$ [M+H]$^+$ 458 found: 458.

Example 28

Preparation of 5-((4'-Chloro-2'-fluorobiphenyl-3-yl)methoxy)-2-cyclopentylisoindolin-1-one

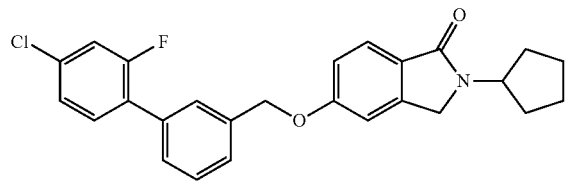 [SMILES: O=C1c2ccc(OCc3cccc(-c4ccc(Cl)cc4F)c3)cc2CN1C1CCCC1]

Yellow oil (50 mg, 32%). $^1$H NMR (400 MHz, DMSO-$d_6$): δ 7.62-7.51 (m, 7H), 7.41-7.38 (m, 1H), 7.22-7.09 (m, 2H), 5.25 (s, 2H), 4.55-4.47 (m, 1H), 4.38 (s, 2H), 1.84-1.57 (m, 8H). LRMS calcd. for $C_{26}H_{23}ClFNO_2$ [M+H]$^+$ 436 found: 436.

Example 29

Preparation of 2-Cyclopentyl-5-((2'-fluoro-4'-(trifluoromethyl)biphenyl-3-yl)methoxy)isoindolin-1-one

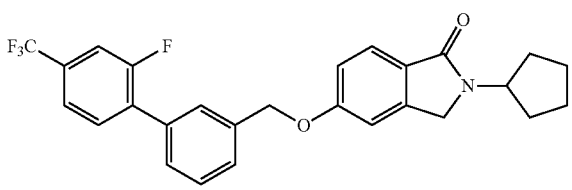 [SMILES: O=C1c2ccc(OCc3cccc(-c4ccc(C(F)(F)F)cc4F)c3)cc2CN1C1CCCC1]

Pale yellow solid (25 mg, 23%). $^1$H NMR (400 MHz, DMSO-$d_6$): δ 7.80-7.53 (m, 8H), 7.22-7.09 (m, 2H), 5.25 (s, 2H), 4.54-4.47 (m, 1H), 4.37 (s, 2H), 1.85-1.56 (m, 8H). LRMS calcd. for $C_{27}H_{23}F_4NO_2$ [M+H]$^+$ 470 found: 470.

Example 30

Preparation of 5-(Biphenyl-3-ylmethoxy)-2-cyclopentylisoindolin-1-one

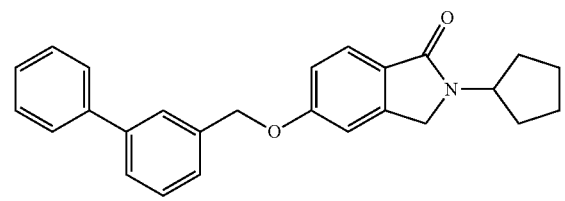 [SMILES: O=C1c2ccc(OCc3cccc(-c4ccccc4)c3)cc2CN1C1CCCC1]

Pale yellow solid (18 mg, 26%). $^1$H NMR (400 MHz, DMSO-$d_6$): δ 7.75 (s, 1H), 7.68-7.35 (m, 9H), 7.23 (d, J=2.3 Hz, 1H), 7.13-7.11 (m, 1H), 5.26 (s, 2H), 4.56-4.48 (m, 1H), 4.38 (s, 2H), 1.87-1.57 (m, 8H). LRMS calcd. for $C_{26}H_{25}NO_2$ [M+H]$^+$ 384 found: 384.

Example 31

General Alternative Synthetic Route for Isoindolinone Analogues

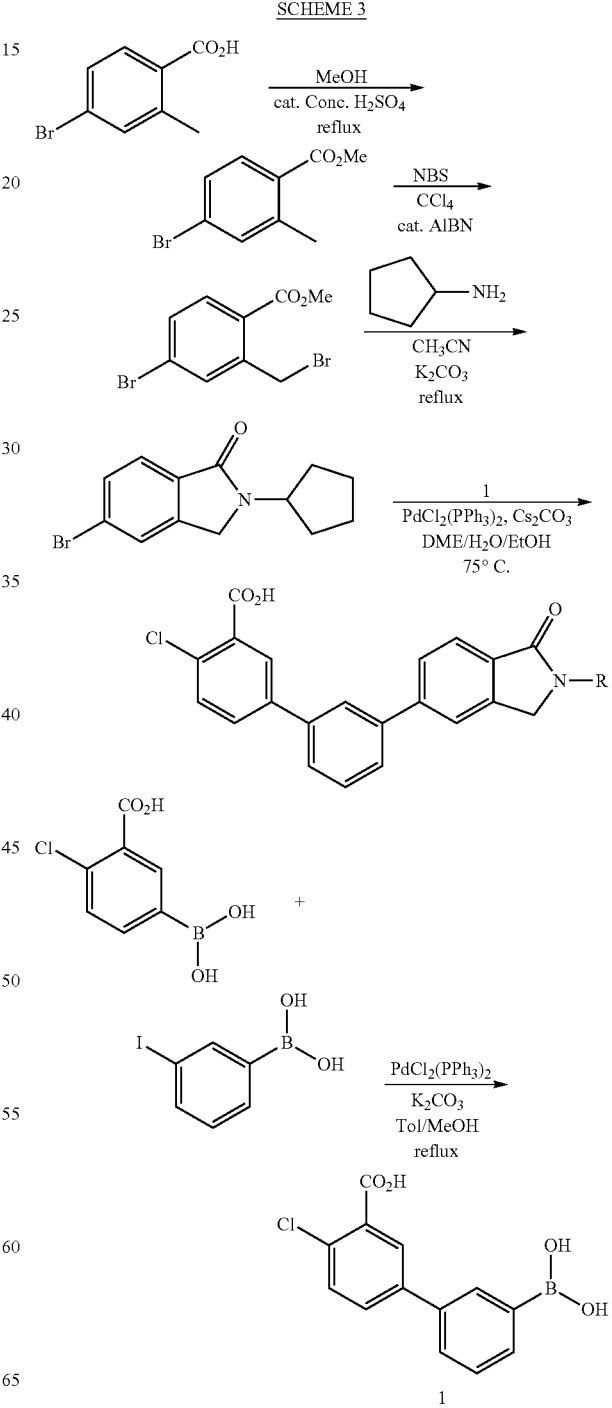

Example 32

Preparation of 5-Bromo-2-cyclopentylisoindolin-1-one $^1$H NMR (400 MHz, CDCl$_3$): δ 7.63-7.51 (m, 3H), 4.71-4.63 (m, 1H), 4.29 (s, 2H), 1.97-1.54 (m, 8H). LRMS calcd. for C$_{13}$H$_{14}$BrNO [M+H]$^+$ 280 found: 280.

Example 33

Preparation of 3'-Borono-4-chlorobiphenyl-3-carboxylic acid

5-Borono-2-chlorobenzoic acid (200 mg, 1 mmol), 3-iodophenylboronic acid (125 mg, 0.5 mmol), K$_2$CO$_3$ (207 mg, 1.5 mmol) and PdCl$_2$(PPh$_3$)$_2$ (37 mg, 0.05 mmol) were dissolved in a mixture of toluene-MeOH (17 mL:1.7 mL) and heated at 75° C. for 3 hours. The mixture was filtered through celite washed with water and the solvent was evaporated in vacuo. The formed crude residue was acidified with 2 M HCl and extracted into EtOAc and dried over anhyd. Na$_2$SO$_4$, evaporated solvent in vacuo to obtain crude 3'-borono-4-chlorobiphenyl-3-carboxylic acid as a reddish brown solid. The crude product was used for the next step without further purification.

Example 34

Preparation of 4-Chloro-3'-(2-cyclopentyl-1-oxoisoindolin-5-yl)biphenyl-3-carboxylic acid

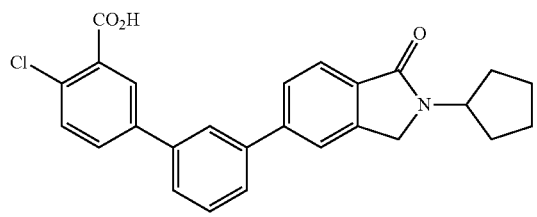 [SMILES: O=C(O)c1cc(-c2cccc(-c3ccc4c(c3)CN(C3CCCC3)C4=O)c2)ccc1Cl]

5-Bromo-2-cyclopentylisoindolin-1-one (76 mg, 0.27 mmol), 3'-borono-4-chlorobiphenyl-3-carboxylic acid (90 mg, 0.33 mmol), Cs$_2$CO$_3$ (268 mg, 0.82 mmol) and PdCl$_2$(PPh$_3$)$_2$ (22 mg, 0.03 mmol), were dissolved in a mixture of DME-H$_2$O-EtOH (9.1 mL:3 mL:2.2 mL) and heated at 75° C. for 2 hours. The mixture was filtered through celite washed with water and filtrate was acidified with 2.5 M HCl to form the crude acid as a yellow solid. The crude residue was purified using automated prep-HPLC to yield the desired compound (14.3 mg, 12%) as a pale yellow solid. $^1$H NMR (400 MHz, CDCl$_3$): δ 8.24 (d, J=2.3 Hz, 1H), 7.94 (d, J=8.0 Hz, 1H), 7.78-7.54 (m, 8H), 4.84-4.75 (m, 1H), 4.43 (s, 2H), 2.08-2.00 (m, 2H), 1.83-1.62 (m, 6H). LRMS calcd. for C$_{26}$H$_{22}$ClNO$_3$ [M+H]$^+$ 432 found: 432.

In a similar manner the following compound were synthesized.

Example 35

Preparation of 4-Chloro-3'-(2-(cyclohexylmethyl)-1-oxoisoindolin-5-yl)biphenyl-3-carboxylic acid

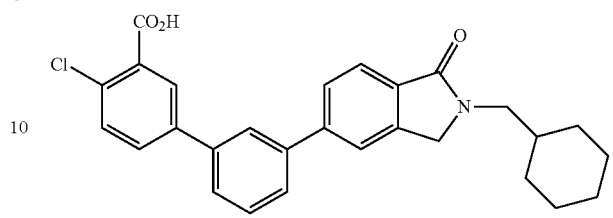

Pale yellow solid (10.6 mg, 13%). $^1$H NMR (400 MHz, DMSO-d$_6$): δ 7.96 (s, 1H), 7.86 (d, J=8.2 Hz, 1H), 7.74-7.54 (m, 8H), 4.51 (s, 2H), 3.36 (d, J=7.3 Hz, 2H), 1.74-1.59 (m, 5H), 1.23-1.15 (m, 4H), 0.98-0.89 (m, 2H). LRMS calcd. for C$_{28}$H$_{26}$ClNO$_3$ [M+H]$^+$ 460 found: 460.

Example 36

General Synthetic Scheme for the Preparation of Benzisothiazolone Derivatives

SCHEME 4

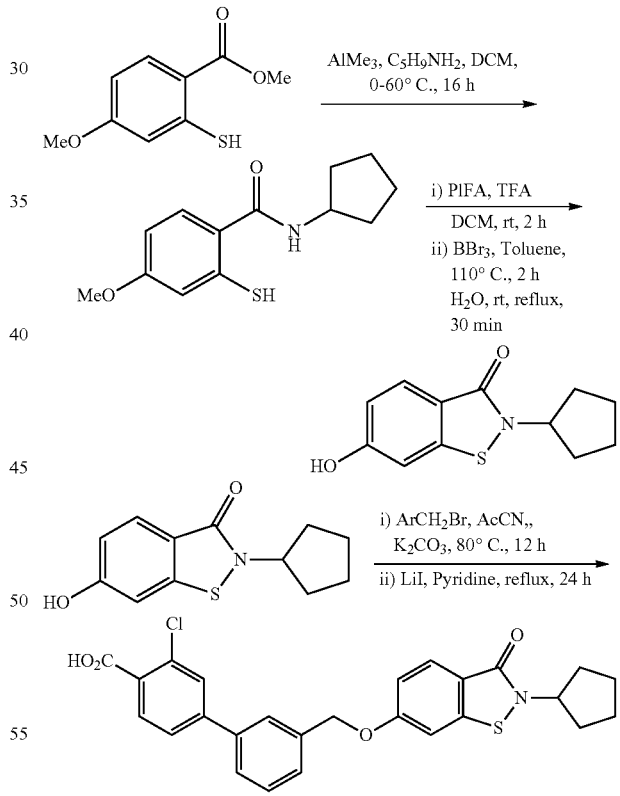

Example 37

Preparation of N-Cyclopentyl-2-mercapto-4-methoxybenzamide

AlMe$_3$ (10 mmol, 2.0 M in toluene) was added dropwise to a cooled (0° C.) suspension of cyclopentylamine (0.85 g, 10 mmol) in CH$_2$Cl$_2$ (30 mL). When the addition was complete, the reaction mixture was allowed to warm to room temperature and stirring was continued for 30 minutes until the gas evolution ceased. Then, a solution of methyl 2-mercapto-4-methoxy-benzoate (0.990 g, 5 mmol) was added. After stirring at 60° C. for 12 h, the mixture was cooled, and carefully quenched with 5% aq HCl (20 mL). The organic layer was separated and the aqueous layer was extracted with CH$_2$Cl$_2$ (3×15 mL). The combined organic extracts were washed with a saturated aqueous solution of NaHCO$_3$ (15 mL) and brine. The organic phase was dried using MgSO$_4$ and evaporated, filtered and the solvent was evaporated in vacuo. The resulting residue was purified by crystallization from Et$_2$O to afford N-cyclopentyl-2-mercapto-4-methoxybenzamide as a tan solid (1.18 g, 94%). $^1$H NMR (DMSO-d$_6$, 300 MHz): δ 8.26 (s, 1H), 7.51 (d, 1H, J=8.7 Hz), 7.01 (s, 1H), 6.72 (d, 1H, J=8. Hz), 5.62 (s, 1H), 4.16-4.14 (m, 1H), 3.78 (s, 3H), 1.99-1.80 (m, 2H), 1.79-1.68 (m, 2H), 1.66-1.53 (m, 4H). LC-MS (ESI) Calcd for C$_{13}$H$_{17}$NO$_2$S [M+H]$^+$: 252.09. Found: 251.95.

Example 38

Preparation of 2-Cyclopentyl-6-methoxybenzo[d]isothiazol-3(2H)-one

A solution of bis(trifluoroacetoxy)iodobenzene (PIFA) (0.645 g, 1.5 mmol) in CH$_2$Cl$_2$ was added to a solution of N-cyclopentyl-2-mercapto-4-methoxybenzamide (0.251 g, 1 mmol) and trifluoroacetic acid (TFA) (0.23 mL, 3 mmol) in CH$_2$Cl$_2$ at 0° C. The resulting mixture was gradually warmed to room temperature. After 1 h, the solvent was evaporated under reduced pressure and the resulting residue was purified by column chromatography using dichloromethane to afford 2-cyclopentyl-6-methoxybenzo[d]isothiazol-3(2H)-one as a white solid (84%, 0.210 g). $^1$H NMR (300 MHz, CDCl$_3$): δ 7.87 (d, 1H, J=8.5 Hz), 6.93 (s, 1H), 6.92 (d, 1H, J=8.2 Hz), 5.50-5.01 (m, 1H), 3.86 (s, 3H), 2.13-2.12 (m, 2H), 1.83-1.67 (m, 6H). LC-MS (ESI) Calcd for C$_{13}$H$_{15}$NO$_2$S [M+H]$^+$: 250.08. Found: 249.95.

Example 39

Preparation of 2-Cyclopentyl-6-hydroxybenzo[d]isothiazol-3(2H)-one

BBr$_3$ (0.54 g, 2 mmol) was added dropwise to a solution of 2-cyclopentyl-6-methoxybenzo[d]isothiazol-3(2H)-one (0.250 g, 1 mmol) in anhydrous benzene (20 mL) at 0° C. The mixture was gradually warmed to room temperature and then heated at 80° C. for 30 min. The reaction mixture was then cooled to room temperature and carefully quenched with H$_2$O (20 mL). The resulting mixture was then heated to reflux for an hour and filtered; the precipitate was washed with H$_2$O and dried under vacuum to give the crude product. The material was purified by flash chromatography (silica gel, CHCl$_3$:CH$_3$OH, 9:1) to afford (0.200 g, 85%) of 2-cyclopentyl-6-hydroxybenzo[d]isothiazol-3(2H)-one as a colorless solid. $^1$H NMR (300 MHz, DMSO-d$_6$): δ 10.36 (s, 1H), 7.60 (d, 1H, J=8.5 Hz), 7.20 (s, 1H), 6.80 (d, 1H, J=8.6 Hz), 4.84-4.81 (m, 1H), 2.12-1.98 (m, 2H), 1.75-1.60 (m, 6H). LC-MS (ESI) Calcd for C$_{12}$H$_{13}$NO$_2$S [M+H]$^+$: 236.0667. Found: 235.95.

Example 40

Preparation of 3-Chloro-3-((2-cyclopentyl-3-oxo-2,3-dihydro-benzo[d]isothiazol-6-yloxy)methyl)biphenyl-4-carboxylic acid Potassium carbonate (0.052 g, 0.38 mmol) was added to a solution of 2-cyclopentyl-6-hydroxybenzo[d]isothiazol-3 (2H)-one (0.075 g, 0.32 mmol) and methyl 3'-(bromomethyl)-3-chlorobiphenyl-4-carboxylate (0.129 g, 0.38 mmol) in CH$_3$CN (5 mL). After stirring for 12 h at 80° C., the organic phase was evaporated under reduced pressure and the crude material was partitioned between water and CH$_2$Cl$_2$. The aqueous layer was extracted with CH$_2$Cl$_2$ (3×15 mL). The organic layer was dried over Na$_2$SO$_4$ and evaporated to give methyl 3-chloro-3'-((2-cyclopentyl-3-oxo-2,3-dihydrobenzo[d]isothiazol-6-yloxy)methyl)biphenyl-4-carboxylate (0.158 g, quantitative yield). The crude product was used for the next step without further purification. LC-MS (ESI) Calcd for C$_{27}$H$_{24}$NO$_3$S [M+H]$^+$: 494.11. Found: 494.00.

LiI (0.042 g, 0.32 mmol) was added to a solution of methyl 3-chloro-3'-((2-cyclopentyl-3-oxo-2,3-dihydrobenzo[d]isothiazol-6-yloxy)methyl)biphenyl-4-carboxylate (0.158 g, 0.32 mmol) in pyridine (5 mL). The reaction mixture was refluxed for 12 h, and then cooled to room temperature. Excess solvent was removed under vacuum. The product was purified by HPLC using isopropanol:water as the solvent system to afford 3-chloro-3'-(2-cyclopentyl-3-oxo-2,3-dihydrobenzo[d]isothiazol-6-yloxy)methyl)biphenyl-4-carboxylic acid as a colorless solid (70 mg, 46% yield). $^1$H NMR (400 MHz, DMSO-d$_6$): δ 8.01 (s, 1H), 7.82 (d, 1H, J=8.5 Hz), 7.80 (d, 1H, J=8.6 Hz), 7.71-7.76 (m, 4H), 7.49-7.47 (m, 2H), 7.05 (d, 1H, J=8.5 Hz), 5.23 (s, 2H), 4.83-4.81 (m, 1H), 2.02-1.99 (m, 21-1), 1.62-1.60 (m, 6H). LC-MS (ESI) Calcd for C$_{26}$H$_{22}$ClNO$_4$S [M+H]$^+$: 480.09. Found: 479.95. HRMS (ESI) calcd for C$_{26}$H$_{22}$ClNO$_4$S [M+H]$^+$: 480.1031. Found: 480.1031.

The following compounds were prepared in a similar manner to the procedure described for 3-Chloro-3'-((2-cyclopentyl-3-oxo-2,3-dihydro-benzo[d]isothiazol-6-yloxy)methyl)biphenyl-4-carboxylic acid.

Example 41

Preparation of 4-Chloro-3'-((2-isopentyl-3-oxo-2,3-dihydrobenzo[d]isothiazol-6-yloxy)methyl)biphenyl-3-carboxylic acid

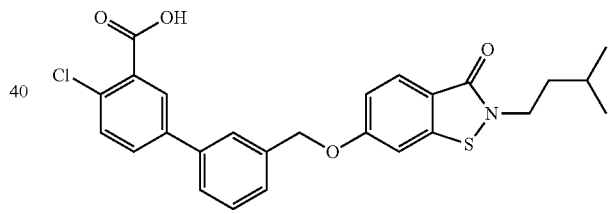

Pale yellow solid (55% over two steps, 0.083 g). $^1$H NMR (400 MHz, DMSO-d$_6$): δ 8.02 (s, 1H), 7.84-7.82 (m, 4H), 7.79 (d, 1H, J=8.5 Hz), 7.58 (d, 1H, J=8.6 Hz), 7.49-7.47 (m, 2H), 7.05 (d, 1H, J=8.5 Hz), 5.32 (s, 2H), 3.76-3.72 (m, 2H), 1.51-1.48 (m, 3H), 0.86 (d, J=6.1 Hz, 6H). LC-MS (ESI) Calcd for C$_{26}$H$_{24}$ClNO$_4$S [M+H]$^+$: 482.11. Found: 482.00.

Example 42

Preparation of 4-Chloro-3'-((2-isobutyl-3-oxo-2,3-dihydrobenzo[d]isothiazol-6-yloxy)methyl)biphenyl-3-carboxylic acid

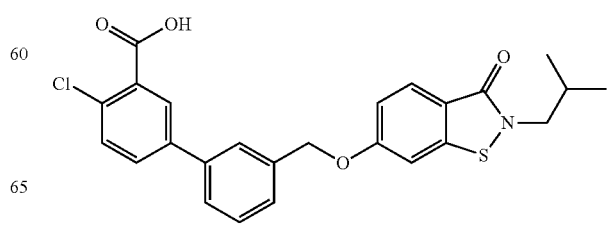

Pale yellow solid (65% over two steps, 0.097 g). $^1$H NMR (400 MHz, CDCl$_3$): δ 8.05 (s, 1H), 7.84-7.80 (m, 1H), 7.56-7.38 (m, 6H), 7.21 (d, 1H, J=8.4 Hz), 6.98 (d, 1H, J=8.5 Hz), 5.17 (s, 2H), 3.58 (d, 2H, J=7.3 Hz), 2.07-1.96 (m, 1H), 0.88 (d, J=6.7 Hz, 6H). LC-MS (ESI) Calcd for C$_{25}$H$_{22}$ClNO$_4$S [M+H]$^+$: 468.09. Found: 467.90.

Example 43

Preparation of 4-Chloro-3'-((2-cyclobutyl-3-oxo-2,3-dihydrobenzo[d]isothiazol-6-yloxy)methyl)biphenyl-3-carboxylic acid

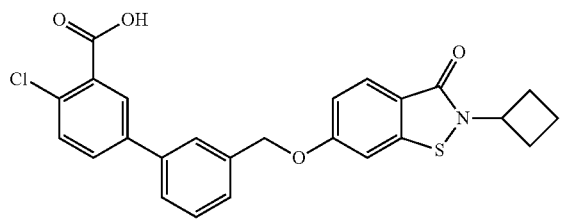 [SMILES: O=C(O)c1cc(-c2cccc(COc3ccc4c(=O)n(C5CCC5)sc4c3)c2)ccc1Cl]

Pale yellow solid (35% over two steps, 0.053 g). $^1$H NMR (400 MHz, CDCl$_3$): g 8.01 (s, 1H), 7.82 (d, 1H, J=8.5 Hz), 7.80 (d, 1H, J=8.6 Hz), 7.71-7.76 (m, 4H), 7.49-7.47 (m, 2H), 7.05 (d, 1H, J=8.5 Hz), 5.17 (s, 2H), 4.63-4.60 (m, 1H), 2.38-2.22 (m, 2H), 2.04-2.02 (m, 2H), 1.37-1.33 (m, 2H). LC-MS (ESI) Calcd for C$_{25}$H$_{20}$ClNO$_4$S [M+H]$^+$: 466.08. Found: 465.90.

Example 44

Preparation of 4-Chloro-3'-((2-(cyclopropylmethyl)-3-oxo-2,3-dihydrobenzo[d]isothiazol-6-yloxy)methyl)biphenyl-3-carboxylic acid

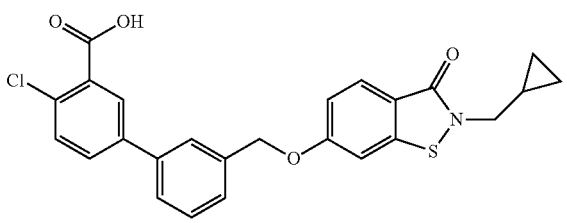 [SMILES: O=C(O)c1cc(-c2cccc(COc3ccc4c(=O)n(CC5CC5)sc4c3)c2)ccc1Cl]

Pale yellow solid (30% over two steps, 0.044 g). $^1$H NMR (400 MHz, DMSO-d$_6$): δ 8.11 (s, 1H), 7.98 (d, 1H, J=8.5 Hz), 7.80 (d, 1H, J=8.6 Hz), 7.71-7.76 (m, 4H), 7.49-7.47 (m, 2H), 7.07 (d, 1H, J=8.5 Hz), 5.23 (s, 2H), 3.33 (d, 2H, J=6.9 Hz), 1.06-0.98 (m, 1H), 0.53-0.51 (m, 2H), 0.35-0.32 (m, 2H). LC-MS (ESI) Calcd for C$_{25}$H$_{20}$ClNO$_4$S [M+H]$^+$: 466.08. Found: 465.95.

Example 45

Preparation of 4-Chloro-3'-((2-cyclopropyl-3-oxo-2,3-dihydrobenzo[d]isothiazol-6-yloxy)methyl)biphenyl-3-carboxylic acid

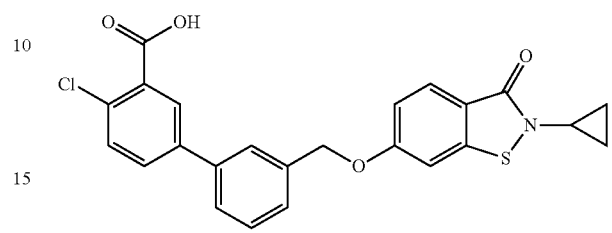

Pale yellow solid (30% over two steps, 0.043 g). $^1$H NMR (400 MHz, DMSO-d$_6$): δ 8.01 (s, 1H), 7.82-7.80 (m, 3H), 7.69 (d, 1H, J=8.6 Hz), 7.60 (d, 1H, J=8.5 Hz), 7.53-7.40 (m, 3H), 7.06 (d, 1H, J=8.6 Hz), 5.23 (s, 2H), 3.00-2.98 (m, 1H), 0.96-0.92 (m, 2H), 0.87-0.83 (m, 2H). LC-MS (ESI) Calcd for C$_{24}$H$_{18}$ClNO$_4$S [M+H]$^+$: 452.06. Found: 451.85.

Example 46

Preparation of 4-Chloro-3'-((2-methyl-3-oxo-2,3-dihydrobenzo[d]isothiazol-6-yloxy)methyl)biphenyl-3-carboxylic acid

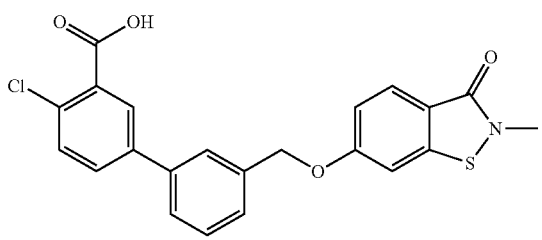 [SMILES: Cn1sc2cc(OCc3cccc(-c4ccc(Cl)c(C(=O)O)c4)c3)ccc2c1=O]

Colorless solid (52% over two steps, 0.070 g). $^1$H NMR (400 MHz, DMSO-d$_6$): δ 8.01 (s, 1H), 7.84-7.79 (m, 3H), 7.72 (d, 1H, J=8.5 Hz), 7.60 (s, 1H), 7.58 (d, 1H, J=8.6 Hz), 7.49-7.47 (m, 2H), 7.05 (d, 1H, J=8.5 Hz), 5.23 (s, 2H), 3.24 (s, 3H). LC-MS (ESI) Calcd for C$_{22}$H$_{16}$ClNO$_4$S [M+H]$^+$: 426.05. Found: 425.90

Example 47

Preparation of 3'-((2-Cyclopentyl-3-oxo-2,3-dihydrobenzo-[d]isothiazol-6-yloxy)methyl)biphenyl-4-carboxylic acid

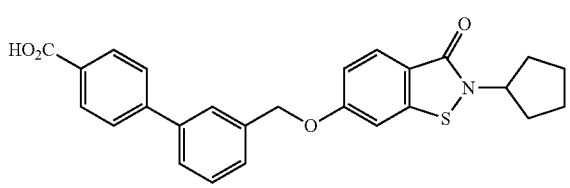 [SMILES: O=C(O)c1ccc(-c2cccc(COc3ccc4c(=O)n(C5CCCC5)sc4c3)c2)cc1]

2-Cyclopentyl-6-hydroxybenzo[d]isothiazol-3(2H)-one (0.094 g, 0.4 mmol) and methyl 3'-(bromomethyl)biphenyl-4-carboxylate (0.146 g, 0.48 mmol) were processed according to the general procedure described for Example 19 to afford 3'-((2-cyclopentyl-3-oxo-2,3-dihydrobenzo[d]isothiazol-6-yloxy)methyl)biphenyl-4-carboxylic acid as a colorless solid in 35% yield over 2 steps (0.053 g, after HPLC purification). $^1$H NMR (400 MHz, DMSO-d$_6$): δ 7.99 (d, 2H, J=8.6 Hz), 7.83-7.79 (m, 5H), 7.70-7.69 (m, 1H), 7.51-7.42 (m, 2H), 7.45 (d, 1H, J=8.5 Hz), 5.34 (s, 2H), 4.49-4.47 (m, 1H), 1.86-1.76 (m, 2H), 1.75-1.57 (m, 6H). HRMS (ESI) calcd for C$_{26}$H$_{23}$NO$_4$S [M+H]$^+$: 446.1420. Found: 446.1420.

Example 48

General Alternative Synthetic Scheme for the Preparation of Benzisothiazolone Derivatives

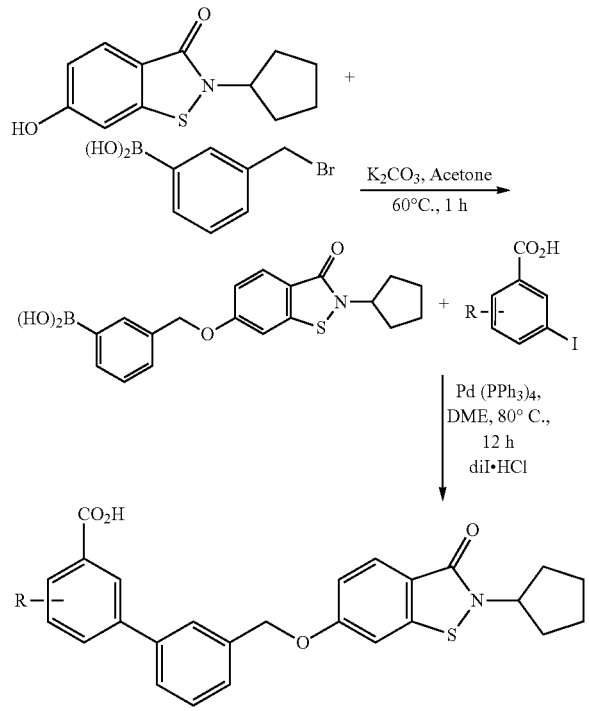

Example 49

Preparation of 342-Cyclopentyl-3-oxo-2,3-dihydrobenzo[d]isothiazol-6-yloxy)methyl)phenylboronic acid Potassium carbonate (0.166 g, 1.2 mmol) was added to a solution of 2-cyclopentyl-7-hydroxy-3,4-dihydroisoquinolin-1(2H)-one (0.235 g, 1 mmol) and 3-(bromomethyl)phenylboronic acid (0.257 g, 1.2 mmol) in acetone (10 mL). After stirring for 1 h at 60° C., the reaction mixture was cooled to room temperature and filtered and the filtrate was evaporated under reduced pressure to give crude 34(2-cyclopentyl-3-oxo-2,3-dihydrobenzo[d]isothiazol-6-yloxy)methyl)phenylboronic acid as a colorless solid (0.315 g, 85%). The crude product was used for the next step without further purification. $^1$H NMR (400 MHz, DMSO-d$_6$): δ 8.12 (s, 2H), 7.83 (s, 1H), 7.73-7.68 (m, 2H), 7.56 (s, 1H), 7.47 (d, 1H, J=7.8 Hz), 7.32 (t, 1H, J=7.8 Hz), 7.04 (d, 1H, J=8.7 Hz), 5.25 (s, 2H), 4.85-4.81 (m, 1H), 2.01-1.98 (m, 2H), 1.75-1.59 (m, 6H). LC-MS (ESI) Calcd for C$_{19}$H$_{20}$BNO$_4$S [M+H]$^+$: 370.12. Found: 369.90.

Example 50

Preparation of (3'-((2-Cyclopentyl-3-oxo-2,3-dihydrobenzo[d]isothiazol-6-yloxy)methyl)-6-methylbiphenyl-3-carboxylic acid

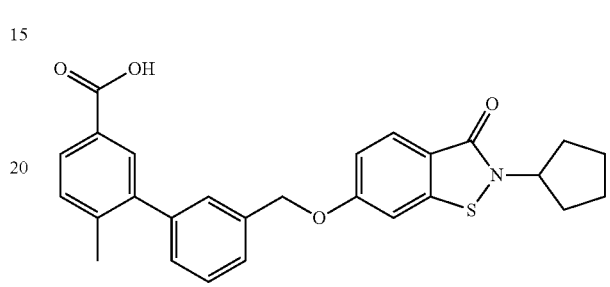

A mixture of 3-((2-cyclopentyl-3-oxo-2,3-dihydrobenzo[d]isothiazol-6-yloxy)methyl)phenylboronic acid (0.050 g, 0.14 mmol), 3-iodo-4-methylbenzoic acid (0.053 g, 0.20 mmol) and tetrakistriphenylphosphinepalladium(0) (0.016 mg, 0.014 mmol) were taken 2 mL of DME. To this 1M Na$_2$CO$_3$ (0.48 mmol) solution was added and the resulting solution was refluxed in an atmosphere of N$_2$ for 12 h. The reaction mixture cooled to room temperature and the solvent was removed under vacuum. The solvent was evaporated and the residue was dissolved in water and neutralized using 1M HCl. The aqueous layer was extracted with ethyl acetate and the organic layer was dried over anhydrous Na$_2$SO$_4$. The solvent was evaporated in vacuum to obtain the crude acid as a yellow solid. The crude residue was purified using automated prep-HPLC to yield the desired compound as a pale yellow solid (0.023 g, 36%). $^1$H NMR (400 MHz, CDCl$_3$): δ 8.01 (s, 1H), 7.90 (d, 1H, J=8.5 Hz), 7.65-7.23 (m, 7H), 7.03 (s, 1H), 5.23 (s, 2H), 4.64-4.59 (m, 1H), 2.34 (s, 3H), 2.16-2.14 (m, 2H), 1.88-1.68 (m, 6H). LC-MS (ESI) Calcd for C$_{27}$H$_{25}$NO$_4$S [M+H]$^+$: 460.15. Found: 460.00.

Example 51

Preparation of 3'-((2-Cyclopentyl-3-oxo-2,3-dihydrobenzo[d]isothiazol-6-yloxy)methyl)-4-methoxybiphenyl-3-carboxylic acid

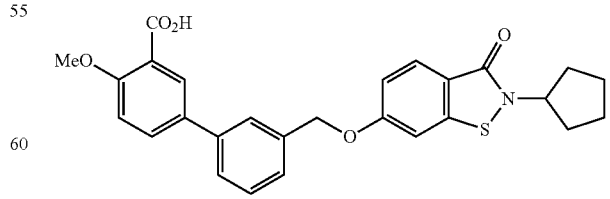

A mixture of 3-((2-cyclopentyl-3-oxo-2,3-dihydrobenzo[d]isothiazol-6-yloxy)methyl)phenylboronic acid (0.050 g, 0.14 mmol), methyl 5-iodo-2-methoxybenzoate (0.056 g, 0.20 mmol) were coupled according to the general procedure and the resulting methyl 3'-((2-cyclopentyl-3-oxo-2,3-dihydrobenzo[d]isothiazol-6-yloxy)methyl)-4-methoxybiphenyl-3-carboxylate was hydrolyzed using LiI (0.019 g, 0.14 mmol) in refluxing pyridine (2 mL) to afford the title product. The crude residue was purified using automated prep-HPLC to yield the desired compound as a pale yellow solid (0.013 g, over two steps 10%). $\delta^1$ NMR (400 MHz, CDCl$_3$): δ 8.44 (s, 1H), 7.87 (d, 1H, J=8.2 Hz), 7.89 (d, 1H, J=8.7 Hz), 7.63 (s, 1H), 7.58 (d, 1H, J=7.8 Hz), 7.49 (t, 1H, J=7.8 Hz), 7.41-7.39 (m, 1H), 7.28-7.24 (m, 2H), 7.14 (d, 1H, J=8.7 Hz), 5.26 (s, 2H), 4.63-4.59 (m, 1H), 3.89 (s, 3H), 2.16-2.04 (m, 2H), 2.04-1.58 (m, 6H). LC-MS (ESI) Calcd for C$_{27}$H$_{25}$NO$_5$S [M+H]$^+$: 475.14. Found: 475.80.

Example 52

Preparation of 3'-((2-Cyclopentyl-3-oxo-2,3-dihydrobenzo[d]isothiazol-6-yloxy)methyl)-6-methoxybiphenyl-3-carboxylic acid

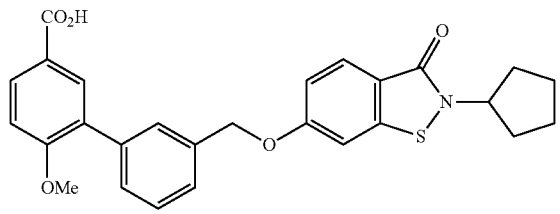 [SMILES: COc1ccc(C(=O)O)cc1-c1cccc(COc2ccc3c(=O)n(C4CCCC4)sc3c2)c1]

A mixture of 3-((2-cyclopentyl-3-oxo-2,3-dihydrobenzo[d]isothiazol-6-yloxy)methyl)phenylboronic acid (0.050 g, 0.14 mmol), 3-iodo-4-methoxybenzoic acid (0.053 g, 0.20 mmol) were coupled according to the general procedure to afford the title product. The crude residue was purified using automated prep-HPLC to yield the desired compound as pale yellow solid (0.013 g, over two steps 10%). $^1$H NMR (400 MHz, CDCl$_3$): δ 7.80-7.66 (m, 2H), 7.60-7.34 (m, 5H), 7.23-7.21 (m, 2H), 6.79 (d, 1H, J=8.5 Hz), 5.02 (s, 2H), 4.44-4.30 (m, 1H), 3.61 (s, 3H), 1.93-1.91 (m, 2H), 1.78-1.45 (m, 6H), LC-MS (ESI) Calcd for C$_{27}$H$_{25}$NO$_5$S [M+H]$^+$: 475.14. Found: 475.80.

Example 53

Preparation of 3'-((2-Cyclopentyl-3-oxo-2,3-dihydrobenzo[d]isothiazol-6-yloxy)methyl)-5-fluorobiphenyl-3-carboxylic acid

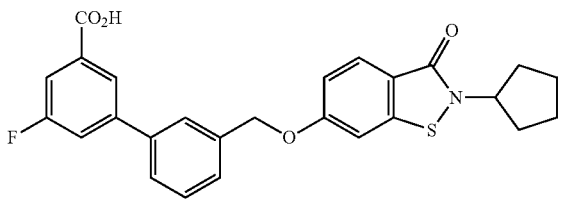 [SMILES: O=C(O)c1cc(F)cc(-c2cccc(COc3ccc4c(=O)n(C5CCCC5)sc4c3)c2)c1]

A mixture of 3-((2-cyclopentyl-3-oxo-2,3-dihydrobenzo[d]isothiazol-6-yloxy)methyl)phenylboronic acid (0.050 g, 0.14 mmol), 3-bromo-5-fluorobenzoic acid (0.044 g, 0.20 mmol) were coupled according to the general procedure to afford the title product. The crude residue was purified using automated prep-HPLC to yield the desired compound as pale yellow solid (0.010 g, over two steps 15%). $^1$H NMR (400 MHz, CDCl$_3$): δ 8.11 (s, 1H), 7.91-7.66 (m, 4H), 7.50-7.24 (m, 4H), 7.03 (s, 1H), 5.24 (s, 2H), 4.64-4.60 (m, 1H), 2.18-2.15 (m, 2H), 1.88-1.66 (m, 6H). LC-MS (ESI) Calcd for C$_{26}$H$_{22}$FNO$_4$S [M+H]$^+$: 463.12. Found: 464.00.

Example 54

General Alternative Synthetic Scheme for the Preparation of Benzisothiazolone Derivatives

SCHEME 6

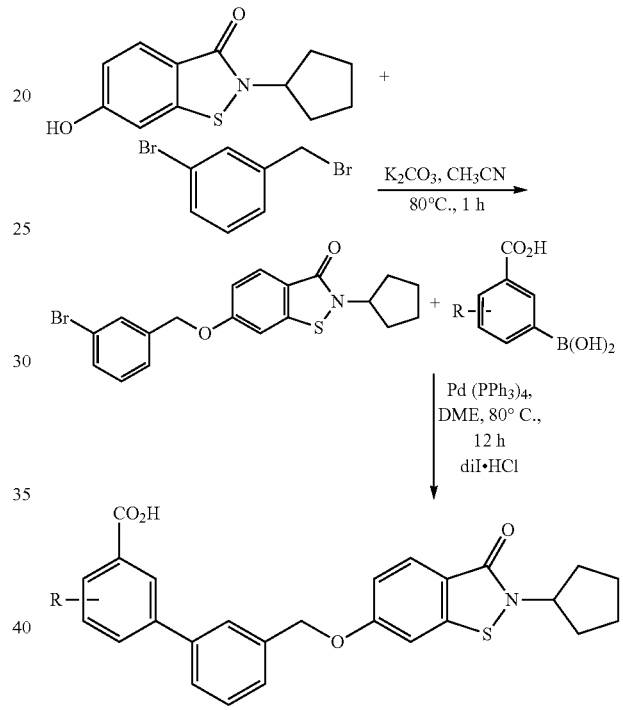

Synthesis of 6-(3-Bromobenzyloxy)-2-cyclopentylbenzo[d]isothiazol-3(2H)-one

Potassium carbonate (0.094 g, 0.66 mmol) was added to a solution of 2-cyclopentyl-7-hydroxy-3,4-dihydroisoquinolin-1(2H)-one (0.132 g, 0.56 mmol) and 1-bromo-3-(bromomethyl)benzene (0.164 g, 0.66 mmol) in CH$_3$CN (10 mL). After stirring for 1 h at 80° C., the organic phase was evaporated under reduced pressure and the crude material was partitioned between water and CH$_2$Cl$_2$. The aqueous layer was extracted with CH$_2$Cl$_2$ (3×15 mL). The organic phase was dried using Na$_2$SO$_4$ and evaporated to give 6-(3-bromobenzyloxy)-2-cyclopentylbenzo[d]isothiazol-3(2H)-one (0.223 g, 98%). The crude product was used for the next step without further purification. $^1$H NMR (400 MHz, CDCl$_3$): δ 7.90 (d, 1H, J=9.6 Hz), 7.58 (s, 1H), 7.48 (d, 1H, J=8.2 Hz), 7.33 (d, 1H, J=7.8 Hz), 7.25 (t, 1H, J=7.7 Hz)), 7.00-6.99 (overlapping singlet and doublet, 2H), 5.09 (s, 2H), 5.04-5.02 (m, 1H), 2.16-2.13 (m, 2H), 1.84-1.67 (m, 6H). LC-MS (ESI) Calcd for C$_{19}$H$_{18}$BrNO$_2$ [M+H]$^+$: 404.02, 406.02. Found: 403.90, 405.80.

Example 55

Preparation of 3'-((2-Cyclopentyl-3-oxo-2,3-dihydrobenzo[d]isothiazol-6-yloxy)methyl)-4-fluorobiphenyl-3-carboxylic acid

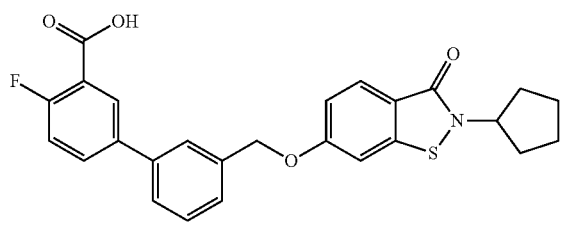 [SMILES: O=C(O)c1cc(-c2cccc(COc3ccc4c(=O)n(C5CCCC5)sc4c3)c2)ccc1F]

A mixture of 6-(3-bromobenzyloxy)-2-cyclopentylbenzo[d]isothiazol-3(2H)-one (0.113 g, 0.28 mmol) 5-borono-2-fluorobenzoic acid (0.063 g, 0.34 mmol), tetrakistriphenylphosphinepalladium(0) (0.032 mg, 0.028 mmol) and 1M Na$_2$CO$_3$ (2 mmol) were refluxed in DME and processed according to the procedure described for 3'-((2-Cyclopentyl-3-oxo-2,3-dihydrobenzo[d]isothiazol-6-yloxy)methyl)-6-ethylbiphenyl-3-carboxylic acid to afford 3'-((2-cyclopentyl-3-oxo-2,3-dihydrobenzo[d]isothiazol-6-yloxy)methyl)-4-fluorobiphenyl-3-carboxylic acid as a pale yellow solid (0.054 g, 42%). $^1$H NMR (400 MHz, CDCl$_3$): δ 8.23 (s, 1H), 7.86 (d, 1H, J=8.7 Hz), 7.61 (s, 1H), 7.57-7.41 (m, 4H), 7.28-7.23 (m, 2H), 7.04 (d, 1H, J=8.7 Hz), 5.25 (s, 2H), 4.61-4.59 (m, 1H), 2.19-2.02 (m, 2H), 1.99-1.65 (m, 6H). LC-MS (ESI) Calcd for C$_{26}$H$_{22}$FNO$_4$S [M+H]$^+$: 464.12. Found: 463.95.

Example 56

Preparation of 2-Cyclopentyl-3-oxo-2,3-dihydrobenzo[d]isothiazol-6-yloxy)methyl)-5-nitrobiphenyl-3-carboxylic acid

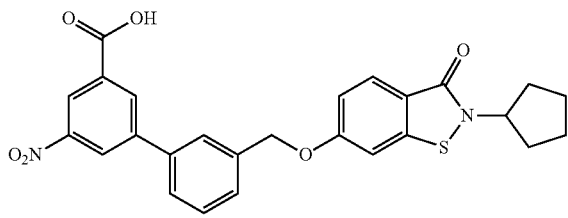 [SMILES: O=C(O)c1cc(-c2cccc(COc3ccc4c(=O)n(C5CCCC5)sc4c3)c2)cc([N+](=O)[O-])c1]

A mixture of 6-(3-bromobenzyloxy)-2-cyclopentylbenzo[d]isothiazol-3(2H)-one (0.043 g, 0.1 mmol) 5-borono-2-fluorobenzoic acid (0.025 g, 0.12 mmol), tetrakistriphenylphosphinepalladium(0) (0.012 mg, 0.028 mmol) and 1M Na$_2$CO$_3$ (2 mmol) were refluxed in DME and processed according to the procedure described for 3'-((2-cyclopentyl-3-oxo-2,3-dihydrobenzo[d]isothiazol-6-yloxy)methyl)-6-methylbiphenyl-3-carboxylic acid to afford 3'-((2-cyclopentyl-3-oxo-2,3-dihydrobenzo[d]isothiazol-6-yloxy)methyl)-5-nitrobiphenyl-3-carboxylic acid as pale yellow solid (0.023 g, 47%). $^1$H NMR (400 MHz, CDCl$_3$): δ 8.87 (s, 1H), 8.65 (s, 1H), 8.61 (s, 1H), 7.87 (d, 1H, J=8.7 Hz), 7.71-7.72 (m, 5H), 6.97 (d, 1H, J=8.5 Hz), 5.24 (s, 2H), 4.63-4.59 (m, 1H), 2.19-2.03 (m, 2H), 1.99-1.66 (m, 6H). δ LC-MS (ESI) Calcd for C$_{26}$H$_{22}$N$_2$O$_6$S [M+H]$^+$: 491.11. Found: 491.00.

Example 57

General Synthetic Scheme for the Preparation of Benzisoxazolone Derivatives

SCHEME 7

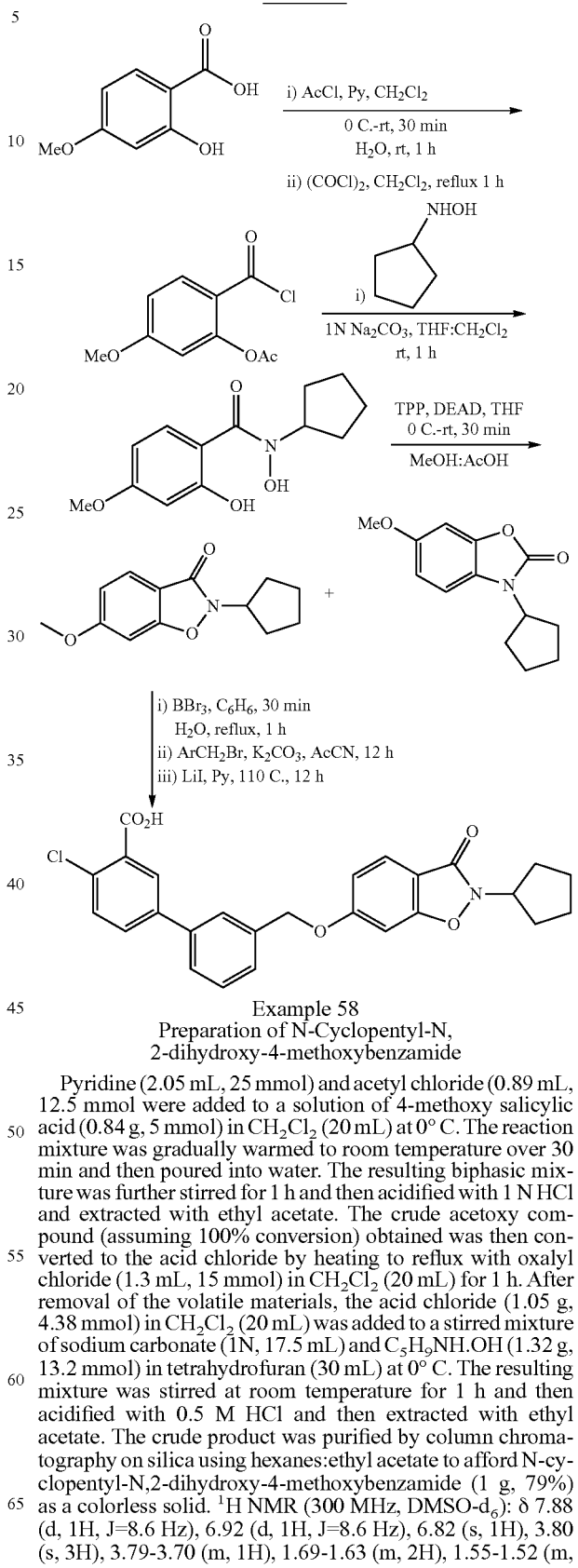

Example 58

Preparation of N-Cyclopentyl-N,2-dihydroxy-4-methoxybenzamide

Pyridine (2.05 mL, 25 mmol) and acetyl chloride (0.89 mL, 12.5 mmol were added to a solution of 4-methoxy salicylic acid (0.84 g, 5 mmol) in CH$_2$Cl$_2$ (20 mL) at 0° C. The reaction mixture was gradually warmed to room temperature over 30 min and then poured into water. The resulting biphasic mixture was further stirred for 1 h and then acidified with 1 N HCl and extracted with ethyl acetate. The crude acetoxy compound (assuming 100% conversion) obtained was then converted to the acid chloride by heating to reflux with oxalyl chloride (1.3 mL, 15 mmol) in CH$_2$Cl$_2$ (20 mL) for 1 h. After removal of the volatile materials, the acid chloride (1.05 g, 4.38 mmol) in CH$_2$Cl$_2$ (20 mL) was added to a stirred mixture of sodium carbonate (1N, 17.5 mL) and C$_5$H$_9$NH.OH (1.32 g, 13.2 mmol) in tetrahydrofuran (30 mL) at 0° C. The resulting mixture was stirred at room temperature for 1 h and then acidified with 0.5 M HCl and then extracted with ethyl acetate. The crude product was purified by column chromatography on silica using hexanes:ethyl acetate to afford N-cyclopentyl-N,2-dihydroxy-4-methoxybenzamide (1 g, 79%) as a colorless solid. $^1$H NMR (300 MHz, DMSO-d$_6$): δ 7.88 (d, 1H, J=8.6 Hz), 6.92 (d, 1H, J=8.6 Hz), 6.82 (s, 1H), 3.80 (s, 3H), 3.79-3.70 (m, 1H), 1.69-1.63 (m, 2H), 1.55-1.52 (m, 6H). LC-MS (ESI) Calcd for $C_{13}H_{17}NO_4$ [M+H]$^+$: 252.12. Found: 252.00.

Example 59

Preparation of 2-Cyclopentyl-6-methoxybenzo[d]isoxazol-3(2H)-one

Diethyl azodicarboxylate was added dropwise to a cooled solution of N-cyclopentyl-N, 2-dihydroxy-4-methoxybenzamide (0.71 g, 2.8 mmol), and triphenylphosphine (0.89 g, 3.4 mmol) in tetrahydrofuran (30 mL) The reaction mixture was warmed to room temperature and quenched with 1:1 $CH_3OH$: $CH_3CO_2H$ (0.2 mL). Removal of the solvent in vacuo followed by chromatographic separation on silica gel afforded 2-cyclopentyl-6-methoxybenzo[d]isoxazol-3(2H)-one as pale yellow solid (0.3 g, 46%). $^1$H NMR (300 MHz, DMSO-$d_6$): δ 7.67 (d, 1H, J=8.7 Hz), 6.78 (d, 1H, J=8.6 Hz), 6.32 (s, 1H), 4.35-4.33 (m, 1H), 3.84 (s, 3H), 1.89-1.68 (m, 8H). LC-MS (ESI) Calcd for $C_{13}H_{15}NO_3$ [M+H]$^+$: 234.10. Found: 233.90.

Example 60

Preparation of 4-Chloro-3'-((2-cyclopentyl-3-oxo-2,3-dihydro-benzo[d]isoxazol-6-yloxy)methyl)biphenyl-3-carboxylic acid $BBr_3$ (0.54 g, 2 mmol) was added dropwise to a solution of 2-cyclopentyl-6-methoxybenzo[d]isoxazol-3(2H)-one (0.232 g, 1 mmol) in anhydrous benzene (20 mL) at 0° C. The mixture was gradually warmed to room temperature and then heated at 80° C. for 30 min. The reaction mixture was then cooled to room temperature and carefully quenched with $H_2O$ (20 mL). The resulting mixture was then heated to reflux for 1 hour and then cooled. Extraction with ethyl acetate and removal of the solvent in vacuo afforded the crude 2-cyclopentyl-6-hydroxyybenzo[d]isoxazol-3(2H)-one (0.170 g, 78%) which was used without further purification. LC-MS (ESI) Calcd for $C_{12}H_{13}NO_3$ [M+H]$^+$: 220.09. Found: 220.00.

2-Cyclopentyl-6-hydroxyybenzo[d]isoxazol-3(2H)-one (0.109 g, 0.5 mmol), methyl 3'-(bromomethyl)-4-chlorobiphenyl-3-carboxylate (0.203 g, 0.6 mmol) and $K_2CO_3$ (0.138 g, 1 mmol) were processed according to the procedure described for Example 19 to give the corresponding ester in 76% yield (0.180 g). LC-MS (ESI) Calcd for $C_{27}H_{24}ClNO_5$ [M+H]$^+$: 478.13. Found: 478.05.

Methyl 3-chloro-3'-((2-cyclopentyl-3-oxo-2,3-dihydrobenzo[d]isoxazol-6-yloxy)methyl)biphenyl-4-carboxylate was treated with LiI in pyridine (3 mL) to give 4-chloro-3'-((2-cyclopentyl-3-oxo-2,3-dihydrobenzo[d]isoxazol-6-yloxy)methyl)biphenyl-3-carboxylic acid (0.063 g, 36% after HPLC purification) as a colorless solid. $^1$H NMR (400 MHz, CDCl$_3$): δ 8.21 (s, 1H), 7.70-7.56 (m, 7H), 6.92 (d, 1H, J=8.6 Hz), 6.74 (s, 1H), 5.18 (s, 2H), 4.98-4.95 (m, 1H), 2.06-2.02 (m, 2H), 1.92-1.88 (m, 4H), 1.64-1.63 (m, 2H). LC-MS (ESI) Calcd for $C_{26}H_{22}ClNO_5$ [M+H]$^+$: 464.13. Found: 463.95. HRMS (ESI)Calcd for $C_{26}H_{22}ClNO_5$ [M+H]$^+$: 464.1259. Found: 464.1261.

Example 61

Preparation of 4-Chloro-3'-((2-cyclohexyl-3-oxo-2,3-dihydro benzo[d]isoxazol-6-yloxy)methyl)biphenyl-3-carboxylic acid

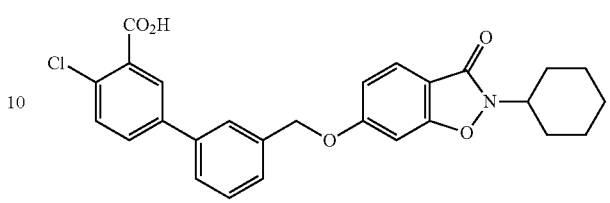

2-Cyclohexyl-6-hydroxybenzo[d]isoxazol-3(2H)-one (0.100 g, 0.43 mmol) and methyl 3'-(bromomethyl)-4-chlorobiphenyl-3-carboxylate (0.174 g, 0.51 mmol) were processed according to the general procedure for Example 23 to provide 4-chloro-3'-((2-cyclohexyl-3-oxo-2,3-dihydrobenzo [d]isoxazol-6-yloxy)methyl)biphenyl-3-carboxylic acid in 31% yield over 2 steps (0.034 g) as a colorless solid. $^1$H NMR (DMSO-$d_6$): δ 8.01 (s, 1H), 7.81 (d, 1H, J=8.6 Hz), 7.79 (d, 1H, J=8.5 Hz), 7.63-7.58 (m, 3H), 7.49-7.48 (m, 2H), 7.15 (s, 1H), 6.95 (d, 1H, J=8.6 Hz), 5.23 (s, 2H), 4.19-4.18 (m, 1H), 1.76-1.69 (m, 7H), 1.66-1.64 (m, 3H). HRMS (ESI)Calcd for $C_{267}H_{24}ClNO_5$ [M+H]$^+$: 478.1416. Found: 478.1418.

Example 62

General Synthetic Scheme for the Preparation of Tetrahydroiso-Quinoline Derivatives

SCHEME 8

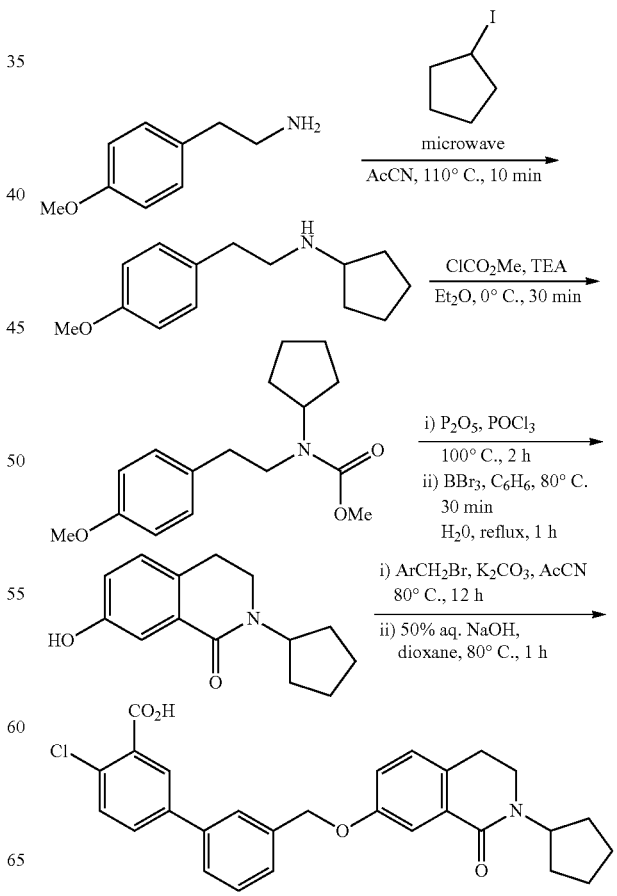

Example 63

Preparation of N-(4-Methoxyphenethyl)cyclopentanamine

4-Methoxyphenethyl amine (0.8 mL, 6 mmol), and cyclopentyl iodide (0.22 mL, 2 mmol) in $CH_3CN$ (5 mL) were irradiated for 10 min in a microwave at 110° C. After cooling to room temperature the mixture was diluted with $CH_2Cl_2$ and washed with $NaHCO_3$ solution. The organic layer was dried over anhydrous $Na_2SO_4$ and evaporated in vacuo. The crude product was purified by silica gel chromatography using hexane as eluent and the product N-(4-methoxyphenethyl)cyclopentanamine (0.854 g, 65%) was obtained as a colorless liquid which solidified upon standing. $^1H$ NMR (400 MHz, $CDCl_3$): δ 8.49 (s, 1H), 7.10 (d, 2H, J=8.6 Hz), 6.78 (d, 2H, J=8.6 Hz), 3.74 (s, 3H), 3.69-3.65 (m, 1H), 3.08-3.07 (m, 4H), 1.84-1.83 (m, 2H), 1.82-1.81 (m, 2H), 1.66-1.56 (m, 4H). LC-MS (ESI) Calcd for: $C_{14}H_{21}NO$ $[M+H]^+$: 220.16. Found: 220.00.

Example 64

Preparation of Methyl cyclopentyl(4-methoxyphenethyl)carbamate

To a solution of N-(4-methoxyphenethyl)cyclopentanamine (0.827 g, 3.77 mmol) in diethyl ether was added triethylamine (0.83 mL, 5.66 mmol) and methyl chloroformate (0.44 mL, 5.66 mmol) at 0° C. The reaction mixture was gradually warmed to room temperature and stirred for 30 min. Filtration and concentration of mixture under reduced pressure gave the crude product which was purified by silica gel column chromatography using hexanes/ethyl acetate to provide the product (0.898 g, 86%) as light yellow oil. $^1H$ NMR (400 MHz, $CDCl_3$): δ 7.10 (d, 2H, J=8.6 Hz), 6.81 (d, 2H, J=8.6 Hz), 4.32-4.12 (m, 1H), 3.76 (s, 3H), 3.69 (s, 3H), 3.24 (t, 2H, J=7.9 Hz), 2.76 (t, 2H, J=7.9 Hz), 1.79-1.76 (m, 2H), 1.67-1.66 (m, 2H), 1.54-1.47 (m, 4H). LC-MS (ESI) Calcd for $C_{16}H_{23}NO_3$ $[M+H]^+$: 278.17. Found: 278.00.

Example 65

Preparation of 2-Cyclopentyl-7-methoxy-3,4-dihydroisoquinolin-1(2H)-one

To a solution of methyl cyclopentyl(4-methoxyphenethyl) carbamate (0.830 g, 3 mmol) in $POCl_3$ (10 mL) was added $P_2O_5$ (0.852, 6 mmol). The reaction mixture was heated at reflux for 2 h. Excess $POCl_3$ was removed under reduced pressure and quenched with ice water. The mixture was neutralized with $Na_2CO_3$, extracted with ethyl acetate and dried over $Na_2SO_4$. Concentration of the solvent followed by chromatographic separation (silica gel, 30% EtOAc:Hexanes) afforded 2-cyclopentyl-7-methoxy-3,4-dihydroisoquinolin-1(2H)-one (0.698 g, 95%). $^1HNMR$ (400 MHz, $CDCl_3$): δ 7.60 (s, 1H), 7.05 (d, 1H, J=8.6 Hz), 6.93 (d, 1H, J=8.6 Hz), 5.19-5.15 (m, 1H), 3.83 (s, 3H), 3.40 (t, 2H, J=6.1 Hz), 2.85 (t, 2H, J=6.1 Hz), 1.90-1.89 (m, 2H), 1.72-1.53 (m, 6H). LC-MS (ESI) Calcd for $C_{15}H_{19}NO_2$ $[M+H]^+$: 246.14. Found: 246.00.

Example 66

Preparation of 2-Cyclopentyl-7-hydroxy-3,4-dihydroisoquinolin-1(2H)-one $BBr_3$ (1.836 g, 7.35 mmol) was added dropwise to a solution of 2-cyclopentyl-7-methoxy-3,4-dihydroisoquinolin-1 (2H)-one (0.600 g, 2.45 mmol) in benzene (50 mL) at 0° C. The mixture was gradually warmed to room temperature and then heated at 80° C. for 30 min. The reaction mixture was then cooled to room temperature and carefully quenched with $H_2O$. The resulting mixture was then heated at reflux for 1 hour and then cooled. Extraction with ethyl acetate and removal of the solvent in vacuo, followed by chromatographic separation (silica gel, $CHCl_3$: $CH_3OH$, 9:1) afforded 2-cyclopentyl-7-hydroxy-3,4-dihydroisoquinolin-1(2H)-one as a colorless solid (0.373 g, 66%). $^1H$ NMR (DMSO-$D_6$): δ 9.42 (s, 1H), 7.25 (s, 1H), 7.02 (d, 1H, J=8.6 Hz), 6.80 (d, 1H, J=8.5 Hz), 4.97-4.93 (m, 1H), 3.32 (t, 2H, J=6.1 Hz), 2.73 (t, 2H, J=6.7 Hz), 1.73-1.64 (m, 4H), 1.53-1.45 (m, 4H). LC-MS (ESI) Calcd for $C_{14}H_{17}NO_2$ $[M+H]^+$: 232.13. Found: 232.00.

Example 67

Preparation of 4-Chloro-3'-((2-cyclopentyl-1-oxo-1,2,3,4-tetrahydro-isoquinolin-7-yloxy)methyl)biphenyl-3-carboxylic acid Potassium carbonate (0.083 g, 0.6 mmol) was added to a solution of 2-cyclopentyl-7-hydroxy-3,4-dihydroisoquinolin-1(2H)-one (0.116 g, 0.5 mmol) and methyl 3'-(bromomethyl)-3-chlorobiphenyl-4-carboxylate (0.203 g, 0.6 mmol) in $CH_3CN$ (10 mL). After stirring for 12 h at 80° C., the organic phase was evaporated under reduced pressure and the crude material was partitioned between water and $CH_2Cl_2$. The aqueous layer was extracted with $CH_2Cl_2$ (3×15 mL). The organic phase was dried using $Na_2SO_4$ and evaporated to give methyl 4-chloro-4'-((2-cyclopentyl-1-oxo-1,2,3,4-tetrahydroisoquinolin-7-yloxy)methyl)biphenyl-3-carboxylate (0.200 g, 82%). The crude product was used for the next step without further purification. LC-MS (ESI) Calcd for $C_{29}H_{28}ClNO_4$ $[M+H]^+$: 490.17. Found: 490.00.

50% Aqueous NaOH (0.5 mL, 0.6 mmol) was added to a solution of the crude ester (0.150 g, 0.3 mmol) in dioxane (5 mL). The reaction mixture was heated to reflux for 1 h, and then cooled to room temperature. Excess solvent was removed under reduced pressure. The residue was diluted with water and then acidified using 1M HCl. Extraction using ethyl acetate, followed by silica gel column chromatography afforded 4-chloro-4'-((2-cyclopentyl-1-oxo-1,2,3,4-tetrahydroisoquinolin-7-yloxy)methyl)biphenyl-3-carboxylic acid as colorless solid (0.125 g, 88%). Final HPLC purification was performed using isopropyl alcohol (IPA):$H_2O$ solvent system. $^1H$ NMR (400 MHz, DMSO-$d_6$): δ 8.00 (s, 1H), 7.60-7.78 (m, 2H), 7.63-7.45 (m, 5H), 7.15 (d, 1H, J=8.6 Hz)), 7.09 (d, 1H, J=8.6 Hz), 5.17 (s, 2H), 4.97-4.93 (m, 1H), 3.34 (t, 2H, J=6.1 Hz), 2.86 (t, 2H, J=6.1 Hz), 1.65-1.50 (m, 8H). LC-MS (ESI) Calcd for $C_{28}H_{26}ClNO_4$ $[M+H]^+$: 476.16. Found: 475.95. HRMS (ESI) calcd for $C_{28}H_{26}ClNO_4$ $[M+H]^+$: 476.1623. Found: 476.1621.

Example 68

General Synthetic Scheme for the Preparation of Isomeric Tetrahydroisoquinoline Derivatives

SCHEME 9

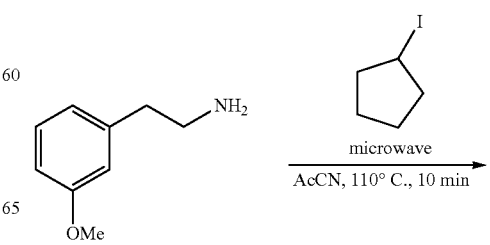

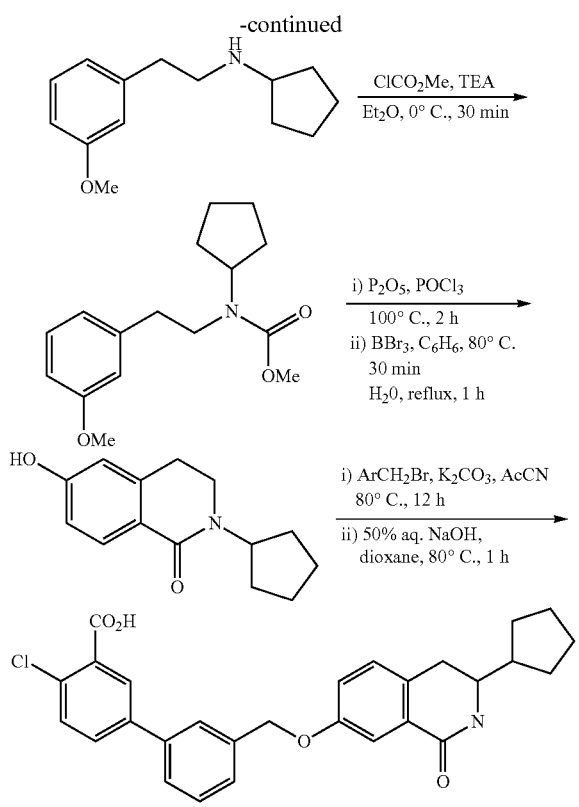

Example 69

Preparation of N-(3-Methoxyphenethyl)cyclopentanamine

3-Methoxyphenethylamine (4.5 mL, 30 mmol), and cyclopentyl iodide (1.15 mL, 10 mmol) in CH$_3$CN (15 mL) were irradiated for 10 min in a microwave at 110° C. After cooling to room temperature the mixture was diluted with CH$_2$Cl$_2$ and washed with NaHCO$_3$ solution. The organic layer was dried over anhydrous Na$_2$SO$_4$ and evaporated in vacuo. The crude product was purified by silica gel chromatography using hexane as eluent and the product N-(3-methoxyphenethyl)cyclopentanamine (1.45 g, 66%) was obtained as a colorless liquid which solidified upon standing. $^1$H NMR (400 MHz, CDCl$_3$): δ 8.48 (s, 1H), 7.20 (t, 1H, J=8.0 Hz), 6.79-6.73 (overlapping doublets and singlet, 3H), 3.74 (s, 3H), 3.44-3.39 (m, 1H), 3.38-3.11 (m, 4H), 1.84-1.83 (m, 2H), 1.82-1.81 (m, 4H), 1.66-1.56 (m, 2H). LC-MS (ESI) Calcd for: C$_{14}$H$_{21}$NO [M+H]$^+$: 220.16. Found: 220.00.

Example 70

Preparation of Methyl cyclopentyl(3-methoxyphenethyl)carbamate

To a solution of N-(3-methoxyphenethyl)cyclopentanamine (1.31 g, 6 mmol) in diethyl ether (50 mL) was added triethylamine (1.3 mL, 9 mmol) and methyl chloroformate (0.7 mL, 9 mmol) at 0° C. The reaction mixture was gradually warmed to room temperature and stirred for 30 min. Filtration and removal of solvent under reduced pressure followed by silica gel column chromatography using hexanes/ethyl acetate afforded methyl cyclopentyl(3-methoxyphenethyl)carbamate as a pale yellow liquid (1.41 g, 84%). $^1$H NMR (400 MHz, CDCl$_3$): δ 7.19 (t, 1H, J=7.6 Hz), 6.78-6.73 (overlapping doublets and singlet, 3H), 4.27-4.24 (m, 1H), 3.78 (s, 3H), 3.70 (s, 3H), 3.28 (t, 2H, J=7.9 Hz), 2.80 (t, 2H, J=7.9 Hz), 1.68-1.67 (m, 2H), 1.53-1.50 (m, 6H). LC-MS (ESI) Calcd for C$_{16}$H$_{23}$NO$_3$ [M+H]$^+$: 278.17. Found: 278.00.

Example 71

Preparation of 2-Cyclopentyl-6-methoxy-3,4-dihydroisoquinolin-1(2H)-one

To a solution of methyl cyclopentyl(3-methoxyphenethyl)carbamate (1.39 g, 5 mmol) in POCl$_3$ (20 mL) was added P$_2$O$_5$ (1.4 g, 10 mmol). The reaction mixture was heated at reflux for 2 h. Excess POCl$_3$ was removed under reduced pressure and the residue was quenched with ice water. The mixture was neutralized with Na$_2$CO$_3$ and extracted with ethyl acetate. The organic phase was dried over Na$_2$SO$_4$. Removal of the solvent in vacuo followed by chromatographic purification afforded 2-cyclopentyl-6-methoxy-3,4-dihydroisoquinolin-1(2H)-one $^1$H NMR (400 MHz, CDCl$_3$): δ 8.00 (d, 1H, J=8.6 Hz), 6.81 (d, 1H, J=8.6 Hz), 6.63 (s, 1H), 5.18-5.14 (m, 1H), 3.85 (t, 1H, J=6.7 Hz), 2.88 (t, 1H, J=6.7 Hz), 1.88-1.70 (m, 2H), 1.64-1.63 (m, 4H), 1.62-1.61 (m, 2H). LC-MS (ESI) Calcd for C$_{15}$H$_{19}$NO$_2$ [M+H]$^+$: 246.14. Found: 246.00.

Example 72

Preparation of 4-Chloro-3'-((2-cyclopentyl-1-oxo-1,2,3,4-tetrahydro-isoquinolin-6-yloxy)methyl)biphenyl-3-carboxylic acid BBr$_3$ (3.7 g, 14.7 mmol) was added dropwise to a solution of 2-cyclopentyl-7-methoxy-3,4-dihydroisoquinolin-1(2H)-one (1.2 g, 4.9 mmol) in benzene (50 mL) at 0° C. The mixture was gradually warmed to room temperature and then heated at 80° C. for 30 min. The reaction mixture was then cooled to room temperature and carefully quenched with H$_2$O. The resulting mixture was then heated at reflux for an hour and then cooled. Extraction with ethyl acetate and removal of the solvent in vacuo, followed by chromatographic purification (silica gel) using CH$_3$OH:CHCl$_3$ afforded 2-cyclopentyl-6-hydroxy-3,4-dihydroisoquinolin-1(2H)-one as a colorless solid (0.735 g, 65%). LC-MS (ESI) Calcd for C$_{14}$H$_{17}$NO$_2$ [M+H]$^+$: 232.13. Found: 232.00.

2-Cyclopentyl-6-hydroxy-3,4-dihydroisoquinolin-1(2H)-one (0.106 g, 0.5 mmol) and methyl 3'-(bromomethyl)-4-chlorobiphenyl-3-carboxylate (0.208 g, 0.6 mmol) were processed according to the general procedure described for 4-chloro-3'-((2-cyclopentyl-1-oxo-1,2,3,4-tetrahydroisoquinolin-7-yloxy)methyl)biphenyl-3-carboxylic acid, to provide 4-chloro-3'-((2-cyclopentyl-1-oxo-1,2,3,4-tetrahydroisoquinolin-6-yloxy)methyl)biphenyl-3-carboxylic acid (0.162 g, 69% over 2 steps) as a colorless solid. $^1$H NMR (400 MHz, DMSO-d$_6$): δ 8.00 (s, 1H), 7.87-7.75 (m, 3H), 7.65-7.57 (m, 2H), 7.49-7.41 (m, 2H), 6.95-6.90 (overlapping doublets and singlet, 2H), 5.20 (s, 2H), 4.97-4.93 (m, 1H), 3.34 (t, 2H, J=6.1 Hz), 2.84 (t, 2H, J=6.1 Hz), 1.69-1.46 (m, 8H). LC-MS (ESI) Calcd for C$_{28}$H$_{26}$ClNO$_4$ [M+H]$^+$: 476.16. Found: 476.00. HRMS (ESI) calcd for C$_{28}$H$_{26}$ClNO$_4$ [M+H]$^+$: 476.1623. Found: 476.1623.

Example 73

Preparation of 4-Chloro-3'-((2-cyclopentyl-3-oxo-2,3-dihydrobenzo[d]isothiazol-6-yloxy)methyl)-N,N-methylbiphenyl-3-carboxamide

SCHEME 10

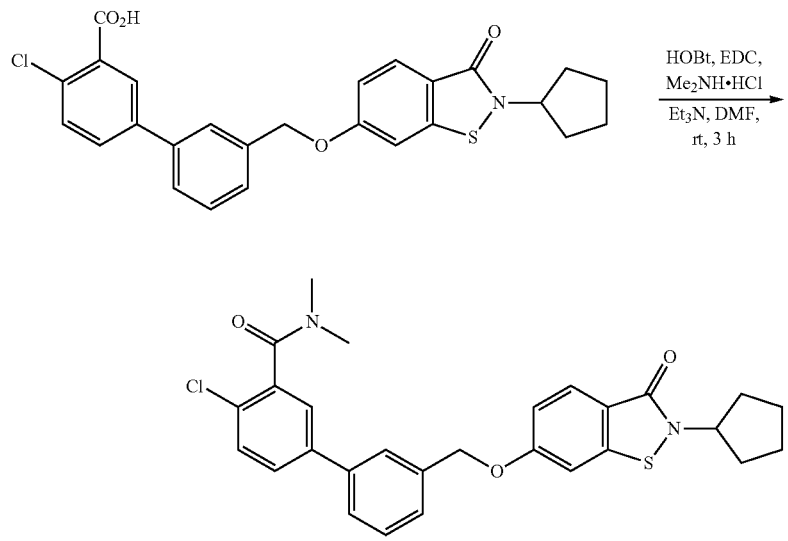

The acid (0.048 g, 0.1 mmol) was dissolved in DMF (2 mL) at room temperature. HOBt (0 016 g, 0.12 mmol) was added in one portion followed by EDC (0.023 g, 0.12 mmol). The resulting mixture was stirred at room temperature for 30 min. To this dimethylamine hydrogen chloride (0.010 g, 0.12) and triethylamine (0.02 mL, 0.12 mmol) was added and stirred for 2 h, and the organic phase was evaporated under reduced pressure and the crude material was partitioned between water and ethyl acetate. The aqueous layer was extracted with ethyl acetate (3×5 mL). The organic phase was dried using $Na_2SO_4$ and evaporated to give 4-chloro-3'-((2-cyclopentyl-3-oxo-2,3-dihydrobenzo[d]isothiazol-6-yloxy)methyl)-N,N-dimethylbiphenyl-3-carboxamide. The crude product was purified by HPLC using isopropanol:water as the solvent system to afford amide as a colorless solid (40 mg, 80% yield). $^1$H NMR (400 MHz, $CDCl_3$): δ 7.87 (d, 1H, J=8.7 Hz), 7.60 (s, 1H), 7.75-7.38 (m, 4H), 7.27-7.24 (m, 3H), 7.03 (d, 1H, J=8.5 Hz), 5.25 (s, 2H), 4.63-4.59 (m, 1H), 3.15 (s, 3H), 2.91 (s, 3H), 2.16-2.03 (m, 2H), 1.62-1.60 (m, 6H). LC-MS (ESI) Calcd for $C_{28}H_{27}ClNO_3S$ $[M+H]^+$: 507.14. Found: 507.05.

In a similar manner using appropriate starting material the following compound was synthesized.

Example 74

Preparation of 4-chloro-3'-((2-cyclopentyl-1-oxoisoindolin-5-yloxy)methyl)-N,N-dimethylbiphenyl-3-carboxamide

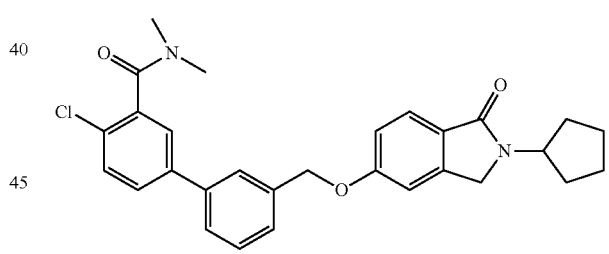

Yellow solid (15.5 mg, 32%). $^1$HNMR (400 MHz, DMSO-$d_6$): δ 7.81-7.47 (m, 8H), 7.21 (s, 1H), 7.12-7.09 (m, 1H), 5.23 (s, 2H), 4.55-4.47 (m, 1H), 4.37 (s, 2H), 3.01 (s, 3H), 2.79 (s, 3H), 1.84-1.56 (m, 8H). LRMS calcd. for $C_{29}H_{29}ClN_2O_3$ $[M+H]^+$ 489 found: 489.

Example 75

Synthetic scheme for the preparation of 4-(4-(2-cyclopentyl-3-oxo-2,3-dihydrobenzo[d]isothiazol-6-yloxy)butoxy)-3-methoxybenzoic acid

SCHEME 11

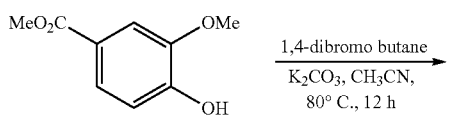

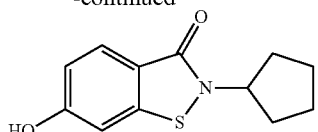

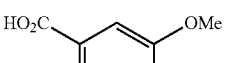

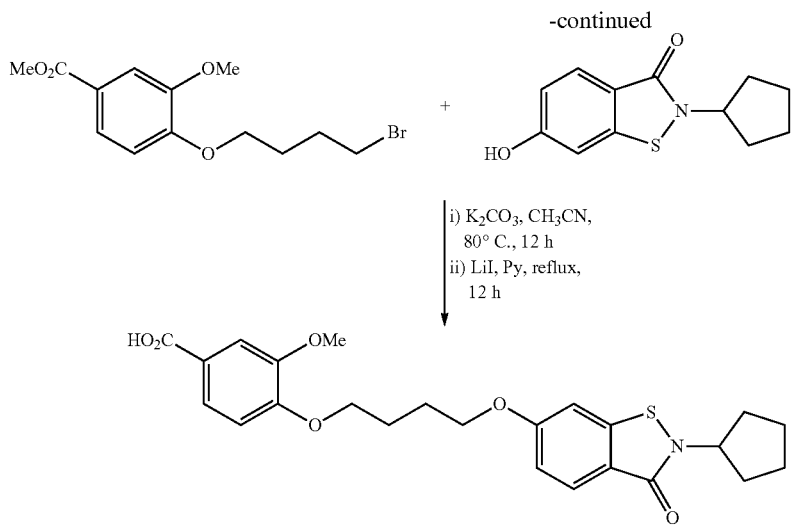

i) K$_2$CO$_3$, CH$_3$CN, 80° C., 12 h
ii) LiI, Py, reflux, 12 h

Example 76

Preparation of Methyl 4-(4-bromobutoxy)-3-methoxybenzoate

Potassium carbonate (0.758 g, 0.48 mmol) was added to a solution of 1,4-dibromo butane (1.18 g, 5.49 mmol) and methyl 4-hydroxy-3-methoxybenzoate (0.5 g, 2.74 mmol) in CH$_3$CN (10 mL). After stirring for 12 h at 80° C., the organic phase was evaporated under reduced pressure and the crude material was partitioned between water and CH$_2$Cl$_2$. The aqueous layer was extracted with CH$_2$Cl$_2$ (3×20 mL). The organic phase was dried using Na$_2$SO$_4$ and evaporated to give the crude methyl 4-(4-bromobutoxy)-3-methoxybenzoate which was purified by column chromatography using hexanes:ethyl acetate to give the pure product as a colorless solid (0.692 g, 80%). $^1$H NMR (400 MHz, CDCl$_3$): δ 7.61 (d, 1H, J=8.3 Hz), 7.51 (s, 1H), 6.83 (d, 1H, J=8.2 Hz), 4.07 (t, 2H, J=5.7 Hz), 3.87 (s, 3H), 3.85 (s, 3H), 3.47 (t, 2H, J=6.4 Hz), 2.04-2.00 (m, 4H). LC-MS (ESI) Calcd for C$_{13}$H$_{17}$BrO$_4$ [M+H]$^+$: 317.03, 319.03. Found: 316.90, 318.90.

Example 77

Preparation of 4-(4-(2-Cyclopentyl-3-oxo-2,3-dihydrobenzo[d]isothiazol-6-yloxy)butoxy)-3-methoxybenzoic acid Potassium carbonate (0.066 g, 0.48 mmol) was added to a solution of 2-cyclopentyl-7-hydroxy-3,4-dihydroisoquinolin-1(2H)-one (0.100 g, 0.42 mmol) and methyl 4-(4-bromobutoxy)-3-methoxybenzoate (0.146 g, 0.46 mmol) in CH$_3$CN (10 mL). After stirring for 12 h at 80° C., the organic phase was and processed according to the procedure described for methyl 4-(4-bromobutoxy)-3-methoxybenzoate to afford the crude methyl 4-(4-(2-cyclopentyl-3-oxo-2,3-dihydrobenzo[d]isothiazol-6-yloxy)butoxy)-3-methoxybenzoate which was used for the next step without any further purification (0.190 g, 96%). LC-MS (ESI) Calcd for C$_{25}$H$_{29}$NO$_6$S [M+H]$^+$: 472.17. Found: 472.00.

Crude ester (0.098 g, 0.2 mmol) was treated with LiI (0.028, 0.5 mmol) in pyridine (3 mL) to give 4-(4-(2-cyclopentyl-3-oxo-2,3-dihydrobenzo[d]isothiazol-6-yloxy)butoxy)-3-methoxybenzoic acid (0.055 g, 60% after HPLC purification) as a colorless solid. $^1$H NMR (400 MHz, CDCl$_3$): δ 7.90 (d, 1H, J=8.2 Hz), 7.84 (d, 1H, J=8.2 Hz), 7.73 (d, 1H, J=6.5 Hz), 7.57 (s, 1H), 7.28 (s, 1H), 6.90 (s, 1H), 6.89 (d, 1H, J=8.7 Hz), 5.06-5.04 (m, 1H), 4.16-4.11 (m, 4H), 3.88 (s, 3H), 2.16-1.65 (m, 12H). LC-MS (ESI) Calcd for C$_{24}$H$_{27}$NO$_6$S [M+H]$^+$: 458.16. Found: 458.00.

In a similar manner the following compound was synthesized.

Example 78

Preparation of 4-(4-(2-cyclopentyl-1-oxoisoindolin-5-yloxy)butoxy)-3-methoxybenzoic acid

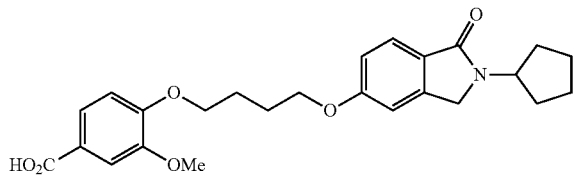 [SMILES: COc1cc(C(=O)O)ccc1OCCCCOc1ccc2c(c1)CN(C1CCCC1)C2=O]

White solid (41 mg, 41%). $^1$H NMR (400 MHz, CDCl$_3$): δ 7.72 (d, J=8.3 Hz, 2H), 7.56 (d, J=1.8 Hz, 1H), 6.98-6.88 (m, 3H), 4.76-4.68 (m, 1H), 4.27 (s, 2H), 4.16 (t, J=5.9 Hz, 2H), 4.09 (t, J=5.9 Hz, 2H), 3.88 (s, 3H), 2.07-1.96 (m, 6H), 1.76-1.61 (m, 6H). LRMS calcd. for C$_{25}$H$_{29}$NO$_6$ [M+H]$^+$ 440 found: 440.

Example 79

Preparation of 4-Chloro-3'-((quinolin-6-yloxy)methyl)biphenyl-3-carboxylic acid

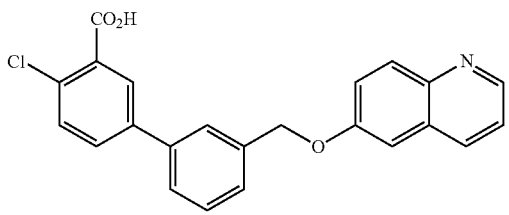 [SMILES: O=C(O)c1cc(-c2cccc(COc3ccc4ncccc4c3)c2)ccc1Cl]

White solid (48.9 mg, 42%). $^1$H NMR (400 MHz, DMSO-d$_6$): δ 8.74-8.71 (m, 1H), 8.24-8.22 (m, 1H), 8.03 (d, J=2.3 Hz, 1H), 7.94-7.91 (m, 1H), 7.85 (s, 1H), 7.83-7.81 (m, 1H), 7.68-7.66 (m, 1H), 7.61 (d, J=8.2 Hz, 1H), 7.56-7.44 (m, 5H), 5.30 (s, 2H). LRMS calcd. for C$_{23}$H$_{16}$ClNO$_3$ [M+H]$^+$ 390 found: 390.

Example 80 mGluR2 PAM, and mGluR2 Ago EC$_{50}$ (µM) Values

| Example | Structure | mGluR2 PAM EC$_{50}$(µM) | mGluR2 Ago EC$_{50}$(µM) |
|---|---|---|---|
| 5 | | >10 | inactive |
| 6 | 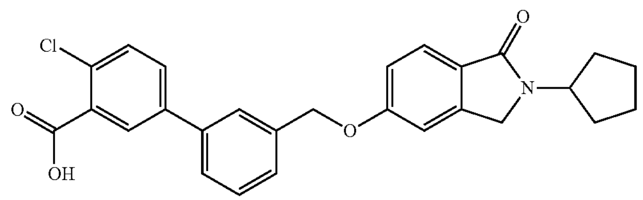 [SMILES: O=C(O)c1cc(-c2cccc(COc3ccc4c(c3)CN(C3CCCC3)C4=O)c2)ccc1Cl] | 0.05 | 0.07 |
| 7 | 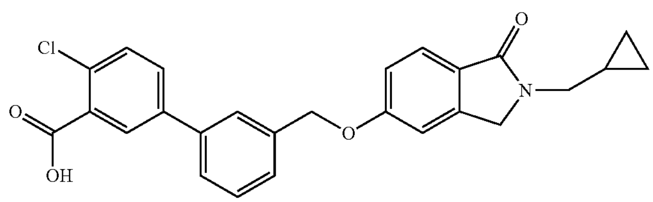 [SMILES: O=C(O)c1cc(-c2cccc(COc3ccc4c(c3)CN(CC3CC3)C4=O)c2)ccc1Cl] | 0.08 | 0.13 |
| 8 | 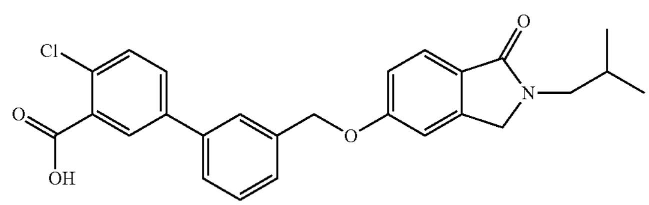 [SMILES: CC(C)CN1Cc2cc(OCc3cccc(-c4ccc(Cl)c(C(=O)O)c4)c3)ccc2C1=O] | 0.1 | 0.15 |
| 9 | 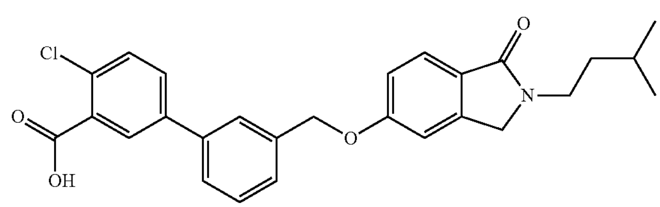 [SMILES: CC(C)CCN1Cc2cc(OCc3cccc(-c4ccc(Cl)c(C(=O)O)c4)c3)ccc2C1=O] | 0.06 | 0.07 |
| 10 | 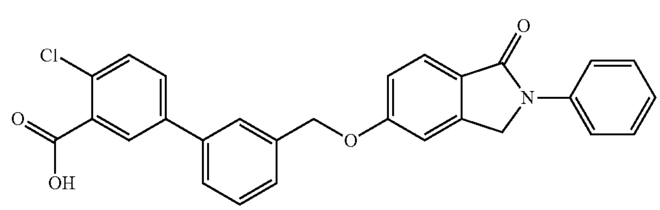 [SMILES: O=C(O)c1cc(-c2cccc(COc3ccc4c(c3)CN(c3ccccc3)C4=O)c2)ccc1Cl] | 0.26 | 0.51 |
| 11 | 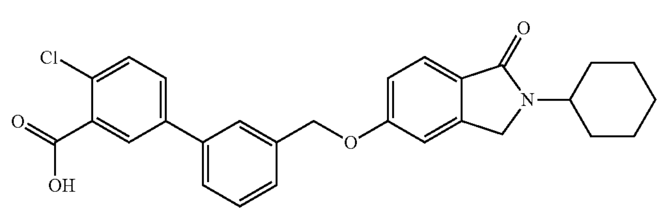 [SMILES: O=C(O)c1cc(-c2cccc(COc3ccc4c(c3)CN(C3CCCCC3)C4=O)c2)ccc1Cl] | 0.27 | 0.29 |

-continued

| Example | Structure | mGluR2 PAM EC$_{50}$(μM) | mGluR2 Ago EC$_{50}$(μM) |
|---|---|---|---|
| 12 | 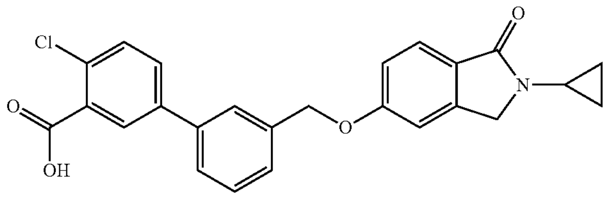 [SMILES: O=C(O)c1cc(-c2cccc(COc3ccc4c(c3)CN(C3CC3)C4=O)c2)ccc1Cl] | 0.22 | 0.28 |
| 13 | 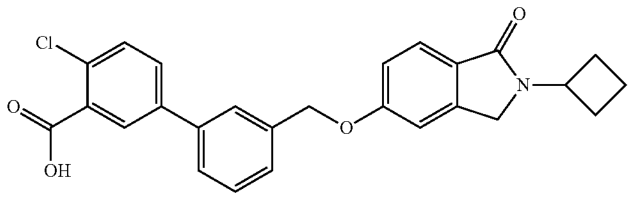 [SMILES: O=C(O)c1cc(-c2cccc(COc3ccc4c(c3)CN(C3CCC3)C4=O)c2)ccc1Cl] | 0.09 | 0.10 |
| 14 | 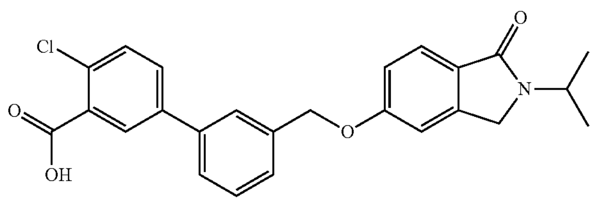 [SMILES: CC(C)N1Cc2cc(OCc3cccc(-c4ccc(Cl)c(C(=O)O)c4)c3)ccc2C1=O] | 0.07 | 0.11 |
| 15 | 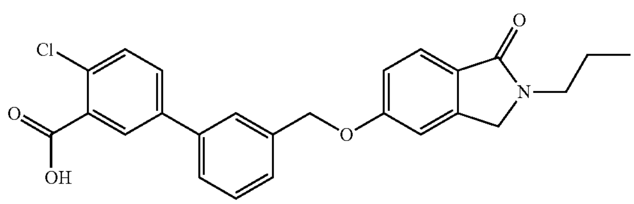 [SMILES: CCCN1Cc2cc(OCc3cccc(-c4ccc(Cl)c(C(=O)O)c4)c3)ccc2C1=O] | >5 | >5.0 |
| 16 | 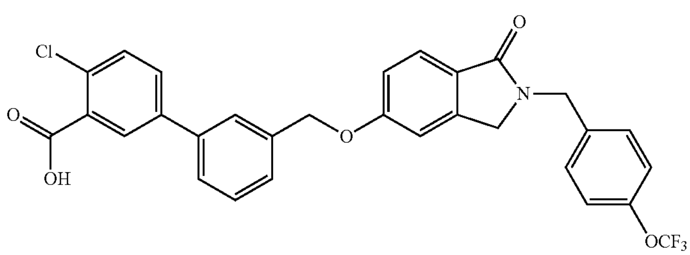 [SMILES: O=C(O)c1cc(-c2cccc(COc3ccc4c(c3)CN(Cc3ccc(OC(F)(F)F)cc3)C4=O)c2)ccc1Cl] | 0.35 | 0.3 |
| 17 | 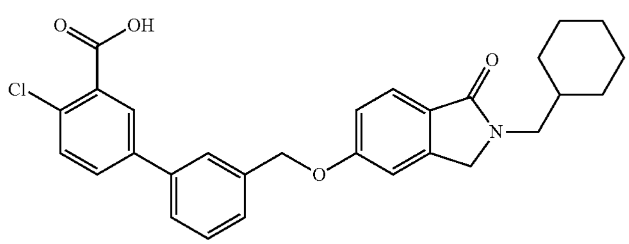 [SMILES: O=C(O)c1cc(-c2cccc(COc3ccc4c(c3)CN(CC3CCCCC3)C4=O)c2)ccc1Cl] | NT | NT |
| 20 | 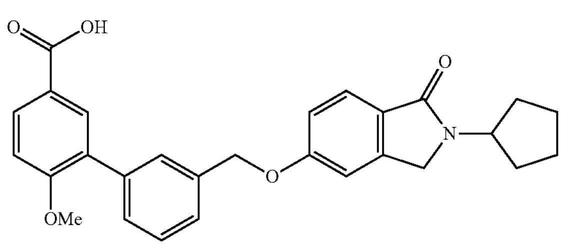 [SMILES: COc1ccc(C(=O)O)cc1-c1cccc(COc2ccc3c(c2)CN(C2CCCC2)C3=O)c1] | 0.08 | NT |

-continued

| Example | Structure | mGluR2 PAM EC$_{50}$(μM) | mGluR2 Ago EC$_{50}$ (μM) |
|---|---|---|---|
| 21 | 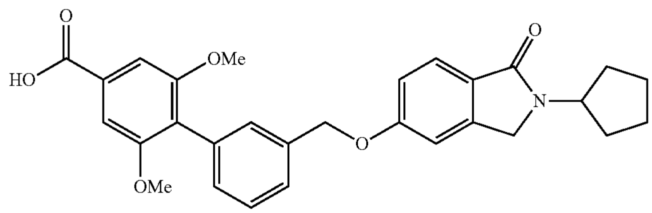 [SMILES: COc1cc(C(=O)O)cc(OC)c1-c1cccc(COc2ccc3c(c2)CN(C2CCCC2)C3=O)c1] | 0.072 | 0.183 |
| 22 | 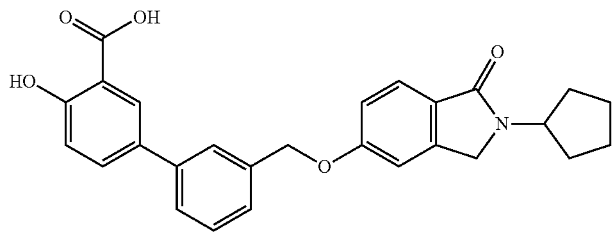 [SMILES: O=C(O)c1cc(-c2cccc(COc3ccc4c(c3)CN(C3CCCC3)C4=O)c2)ccc1O] | 0.023 | 0.052 |
| 23 | 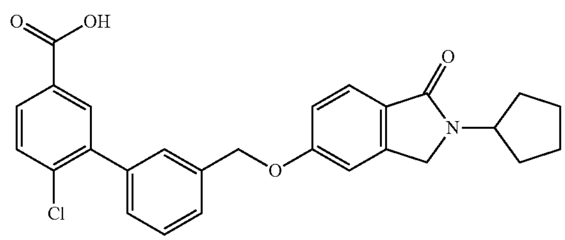 [SMILES: O=C(O)c1ccc(Cl)c(-c2cccc(COc3ccc4c(c3)CN(C3CCCC3)C4=O)c2)c1] | 0.089 | 0.145 |
| 24 | 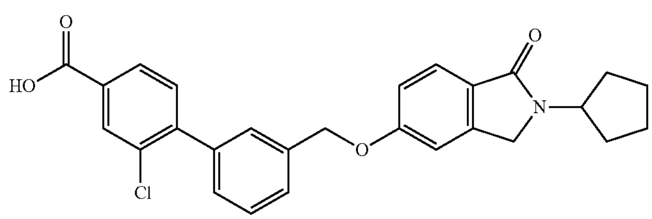 [SMILES: O=C(O)c1ccc(-c2cccc(COc3ccc4c(c3)CN(C3CCCC3)C4=O)c2)c(Cl)c1] | 0.111 | 0.19 |
| 25 | 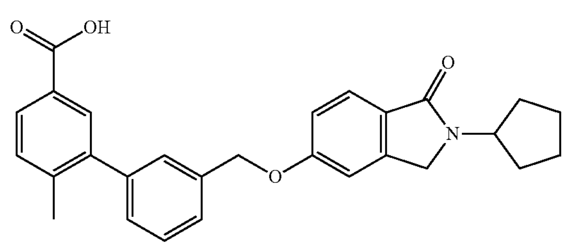 [SMILES: Cc1ccc(C(=O)O)cc1-c1cccc(COc2ccc3c(c2)CN(C2CCCC2)C3=O)c1] | 0.11 | NT |
| 26 | 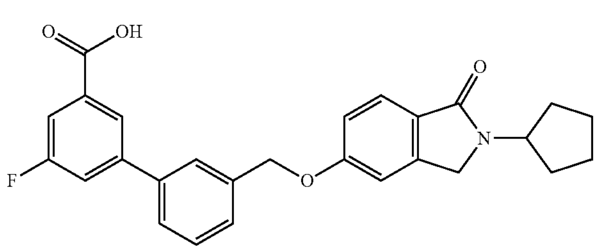 [SMILES: O=C(O)c1cc(F)cc(-c2cccc(COc3ccc4c(c3)CN(C3CCCC3)C4=O)c2)c1] | 0.13 | NT |

-continued

| Example | Structure | mGluR2 PAM EC$_{50}$(μM) | mGluR2 Ago EC$_{50}$(μM) |
|---|---|---|---|
| 27 | 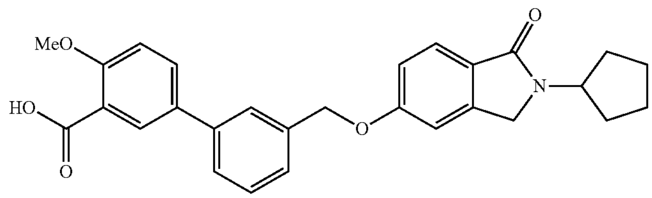 [SMILES: COc1ccc(-c2cccc(COc3ccc4c(c3)CN(C3CCCC3)C4=O)c2)cc1C(=O)O] | 0.173 | NT |
| 28 | 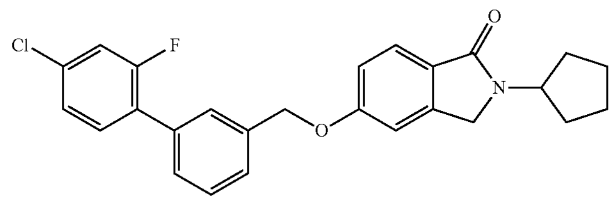 [SMILES: O=C1c2ccc(OCc3cccc(-c4ccc(Cl)cc4F)c3)cc2CN1C1CCCC1] | NT | NT |
| 29 | 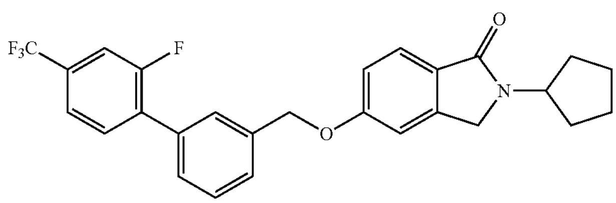 [SMILES: O=C1c2ccc(OCc3cccc(-c4ccc(C(F)(F)F)cc4F)c3)cc2CN1C1CCCC1] | NT | NT |
| 30 | 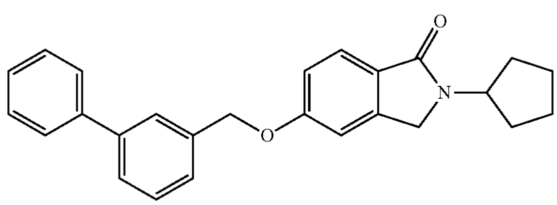 [SMILES: O=C1c2ccc(OCc3cccc(-c4ccccc4)c3)cc2CN1C1CCCC1] | 3.24 | NT |
| 34 | 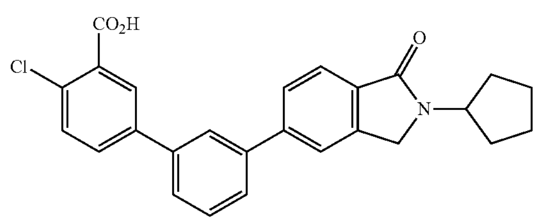 [SMILES: O=C(O)c1cc(-c2cccc(-c3ccc4c(c3)CN(C3CCCC3)C4=O)c2)ccc1Cl] | 0.02 | 0.08 |
| 35 | 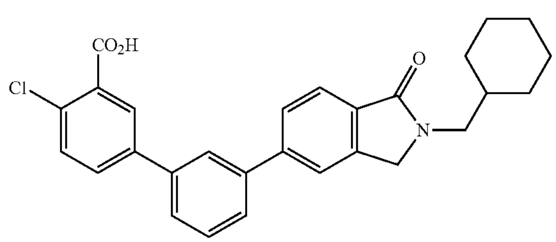 [SMILES: O=C(O)c1cc(-c2cccc(-c3ccc4c(c3)CN(CC3CCCCC3)C4=O)c2)ccc1Cl] | NT | NT |
| 40 | 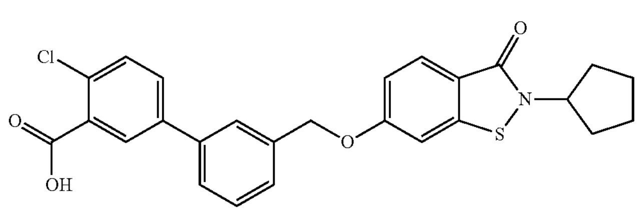 | 0.17 | 0.12 |

-continued

| Example | Structure | mGluR2 PAM EC$_{50}$(μM) | mGluR2 Ago EC$_{50}$(μM) |
|---|---|---|---|
| 41 | 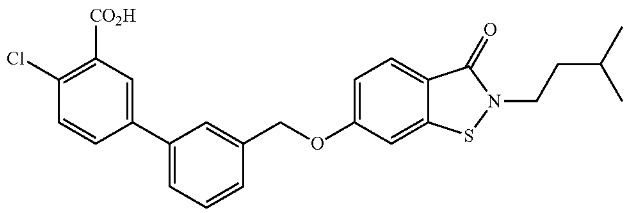 [SMILES: CC(C)CCn1sc2cc(OCc3cccc(-c4ccc(Cl)c(C(=O)O)c4)c3)ccc2c1=O] | desensitizes | 0.655 |
| 42 | 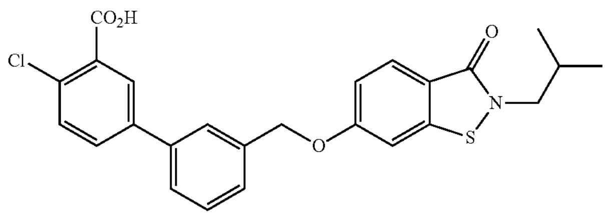 [SMILES: CC(C)Cn1sc2cc(OCc3cccc(-c4ccc(Cl)c(C(=O)O)c4)c3)ccc2c1=O] | desensitizes | 0.33 |
| 43 | 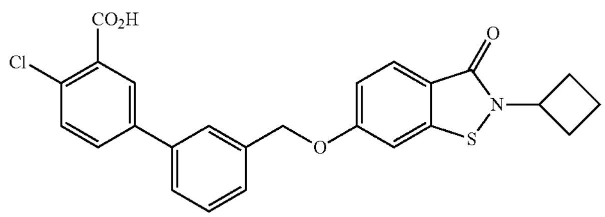 [SMILES: O=C(O)c1cc(-c2cccc(COc3ccc4c(=O)n(C5CCC5)sc4c3)c2)ccc1Cl] | 0.629 | 0.725 |
| 44 | 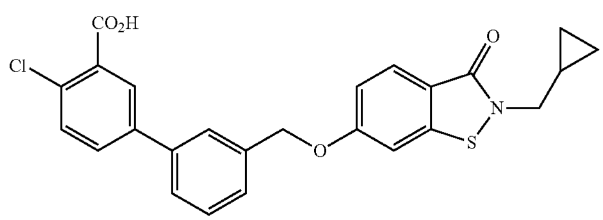 [SMILES: O=C(O)c1cc(-c2cccc(COc3ccc4c(=O)n(CC5CC5)sc4c3)c2)ccc1Cl] | weak PAM | weak agonist |
| 45 | 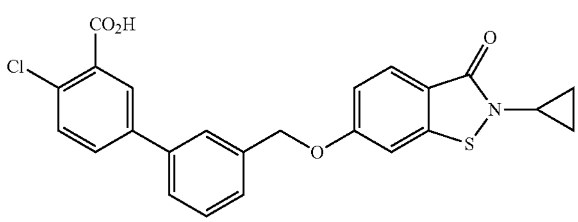 [SMILES: O=C(O)c1cc(-c2cccc(COc3ccc4c(=O)n(C5CC5)sc4c3)c2)ccc1Cl] | 0.134 | 0.199 |
| 46 | 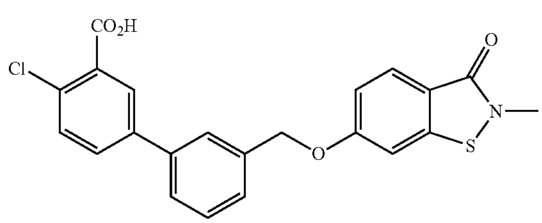 [SMILES: Cn1sc2cc(OCc3cccc(-c4ccc(Cl)c(C(=O)O)c4)c3)ccc2c1=O] | 0.644 | 1.05 |
| 47 | 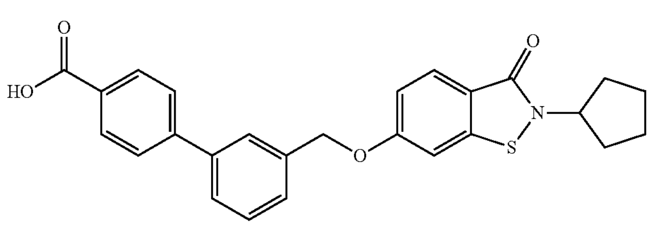 [SMILES: O=C(O)c1ccc(-c2cccc(COc3ccc4c(=O)n(C5CCCC5)sc4c3)c2)cc1] | 0.54 | 0.62 |

-continued

| Example | Structure | mGluR2 PAM EC$_{50}$(μM) | mGluR2 Ago EC$_{50}$(μM) |
|---|---|---|---|
| 50 | 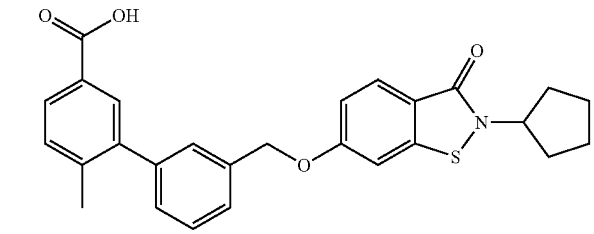 [SMILES: Cc1ccc(C(=O)O)cc1-c1cccc(COc2ccc3c(=O)n(C4CCCC4)sc3c2)c1] | 0.674 | NT |
| 51 | 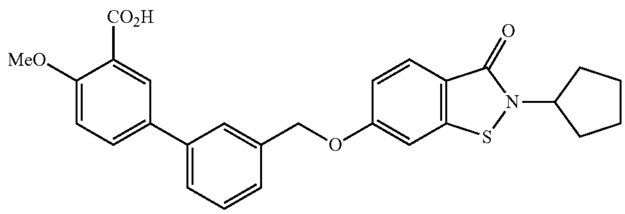 [SMILES: COc1ccc(-c2cccc(COc3ccc4c(=O)n(C5CCCC5)sc4c3)c2)cc1C(=O)O] | NT | NT |
| 52 | 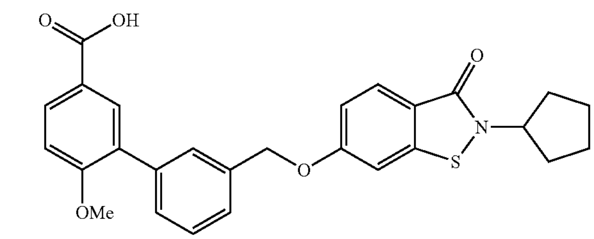 [SMILES: COc1ccc(C(=O)O)cc1-c1cccc(COc2ccc3c(=O)n(C4CCCC4)sc3c2)c1] | NT | NT |
| 53 | 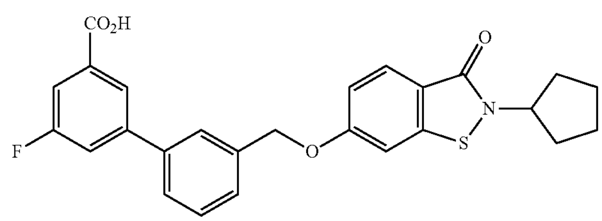 [SMILES: O=C(O)c1cc(F)cc(-c2cccc(COc3ccc4c(=O)n(C5CCCC5)sc4c3)c2)c1] | NT | NT |
| 55 | 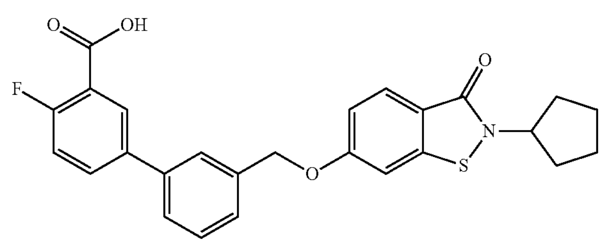 [SMILES: O=C(O)c1cc(-c2cccc(COc3ccc4c(=O)n(C5CCCC5)sc4c3)c2)ccc1F] | NT | NT |
| 56 | 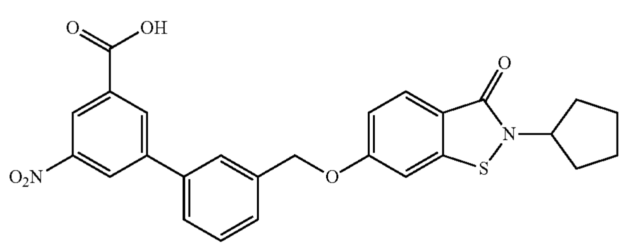 [SMILES: O=C(O)c1cc(-c2cccc(COc3ccc4c(=O)n(C5CCCC5)sc4c3)c2)cc([N+](=O)[O-])c1] | NT | NT |

-continued

| Example | Structure | mGluR2 PAM EC$_{50}$(µM) | mGluR2 Ago EC$_{50}$(µM) |
|---|---|---|---|
| 60 | 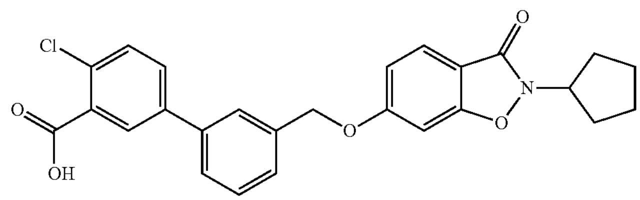 [SMILES: O=C(O)c1cc(-c2cccc(COc3ccc4c(=O)n(C5CCCC5)oc4c3)c2)ccc1Cl] | 0.31 | 0.34 |
| 61 | 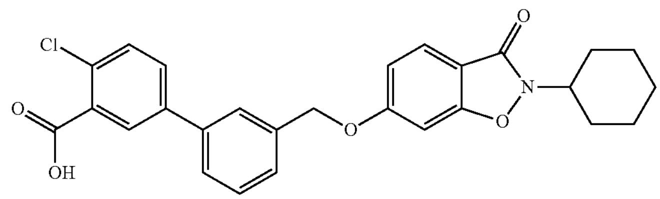 [SMILES: O=C(O)c1cc(-c2cccc(COc3ccc4c(=O)n(C5CCCCC5)oc4c3)c2)ccc1Cl] | desensitizes | 0.91 |
| | | >10 | >10 |
| 67 | 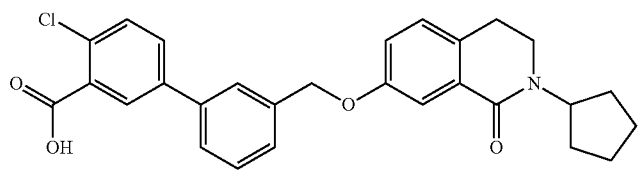 [SMILES: O=C(O)c1cc(-c2cccc(COc3ccc4c(c3)C(=O)N(C3CCCC3)CC4)c2)ccc1Cl] | >10 | >10 |
| 72 | 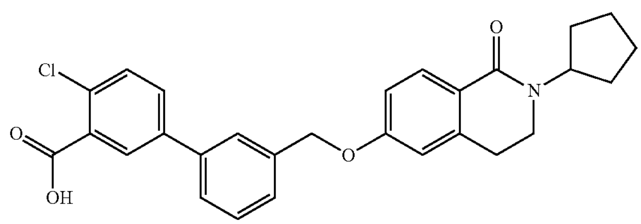 [SMILES: O=C(O)c1cc(-c2cccc(COc3ccc4c(c3)CCN(C3CCCC3)C4=O)c2)ccc1Cl] | 0.3 | 0.32 |
| 73 | 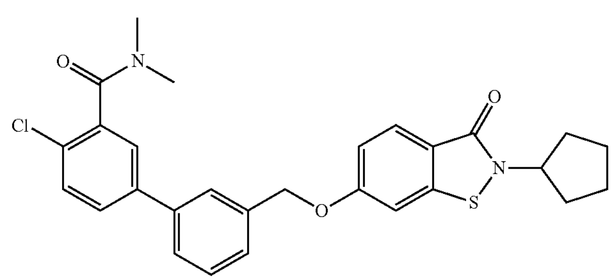 [SMILES: CN(C)C(=O)c1cc(-c2cccc(COc3ccc4c(=O)n(C5CCCC5)sc4c3)c2)ccc1Cl] | NT | NT |
| 74 | 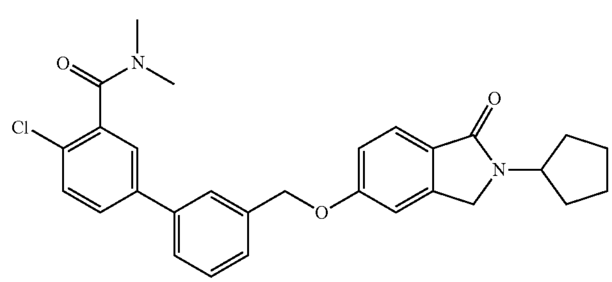 [SMILES: CN(C)C(=O)c1cc(-c2cccc(COc3ccc4c(c3)CN(C3CCCC3)C4=O)c2)ccc1Cl] | 1.46 | NT |

| Example | Structure | mGluR2 PAM EC$_{50}$(µM) | mGluR2 Ago EC$_{50}$(µM) |
|---|---|---|---|
| 77 | HO$_2$C—⬡(OMe)—O—(CH$_2$)$_4$—O—[benzisothiazolone]-N-cyclopentyl | 0.315 | NT |
| 78 | HO$_2$C—⬡(OMe)—O—(CH$_2$)$_4$—O—[isoindolinone]-N-cyclopentyl | 0.176 | 0.479 |

Although the disclosure has been described with reference to the above example, it will be understood that modifications and variations are encompassed within the spirit and scope of the disclosure.

What is claimed is:

1. A compound of Formula IV:

$$\text{(IV)}$$

(R$^1$)$_m$—(⬡)$_y$—X—(CH$_2$)$_q$—X'—[benzo-fused ring with W]—C(O)—N—R$^3$ wherein:

X and X' are each independently absent or are each independently O;

y is 1;

q is independently an integer selected from 0, 1, 2, 3, and 4;

m is an integer selected from 0, 1, 2, and 3;

W is independently selected from CH$_2$, O, S, and NCH$_3$;

R$^1$ is independently selected from hydrogen, halogen, cyano, nitro, unsubstituted C$_1$-C$_6$ alkyl, perfluoroalkyl, —(CH$_2$)$_j$OR$^5$, —(CH$_2$)$_j$C(O)OR$^5$, and (CH$_2$)$_j$C(O)NR$^6$R$^7$, wherein each j is 0;

R$^3$ is independently selected from hydrogen, branched or unbranched alkyl, cycloalkyl, phenyl, benzyl and cycloalkylalkyl, wherein benzyl is optionally substituted with perfluoroalkoxy; and R$^5$, R$^6$, and R$^7$ are each independently selected from hydrogen branched or unbranched alkyl.

2. The compound of claim 1, wherein the compound of Formula IV has Formula V:

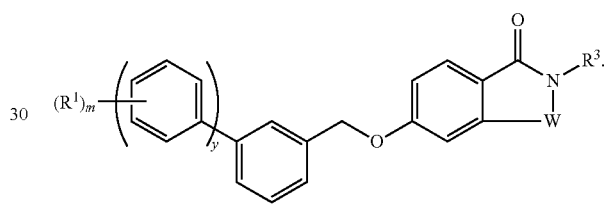

3. The compound of claim 1, wherein the compound of Formula IV is:

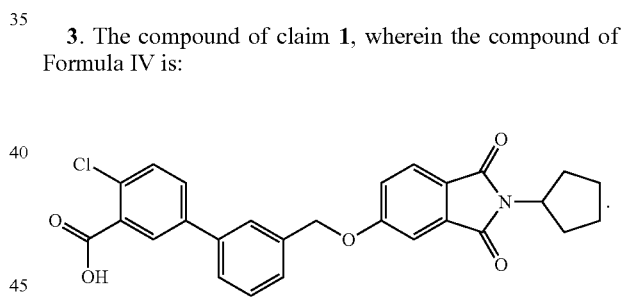

4. A method of treating a CNS disorder including schizophrenia, anxiety and addiction, the method comprising the step of administering to a subject in need thereof, an effective amount of the compound of claim 1 having Formula IV, thereby treating the disorder.

5. The method of claim 4, wherein the disorder is an addictive disorder.

6. The method of claim 5, wherein the addictive disorder is nicotine addiction, alcohol addiction, opiate addiction, amphetamine addiction, methamphetamine addiction, or cocaine addiction.

7. The method of claim 6, wherein the addictive disorder is nicotine addiction.

8. The method of claim 6, wherein the addictive disorder is cocaine addiction.

9. The method of claim 4, wherein the CNS disorder is schizophrenia.

10. A method of treating a warm-blooded animal having an addictive disorder or schizophrenia, the method comprising the step of administering to the animal an effective amount of the compound of claim 1 having Formula IV, thereby treating the disorder or schizophrenia.

11. A pharmaceutical composition comprising the compound of claim 1 having Formula IV, and a pharmaceutically acceptable carrier.

12. A method of treating substance abuse, the method comprising the step of administering to a subject in need thereof, an effective amount of the compound of claim 1 having Formula IV, wherein the effective amount is sufficient to diminish, inhibit or eliminate desire for and/or consumption of the substance in the subject.

13. The method of claim 1, wherein the substance is nicotine, alcohol, opiates, amphetamines, methamphetamines, or cocaine.

14. A method for treating an addictive disorder, the method comprising the steps of: a) administering to a subject in need thereof, an effective amount of the compound of claim 1 having Formula IV, during a first time period, wherein the first time period is a time period wherein the subject expects to be in an environment wherein, or exposed to stimuli in the presence of which, the subject habitually uses an addictive substance; and b) administering an effective amount of the compound of claim 1 having Formula IV during a second time period, wherein the second time period is a time period wherein the subject is suffering from withdrawal.

15. The compound of claim 1, wherein $R^3$ is cycloalkyl.

16. The compound of claim 1, wherein m is 2.

17. The compound of claim 1, wherein:
m is an integer selected from 1, 2, and 3; and
at least one $R^1$ is halogen.

\* \* \* \* \*

UNITED STATES PATENT AND TRADEMARK OFFICE
CERTIFICATE OF CORRECTION

PATENT NO. : 8,748,632 B2  
APPLICATION NO. : 13/051798  
DATED : June 10, 2014  
INVENTOR(S) : Nicholas D. P. Cosford et al.

Page 1 of 1

It is certified that error appears in the above-identified patent and that said Letters Patent is hereby corrected as shown below:

In the Claims

Claim 3; Column 94, Lines 38-45; delete the following structure:

"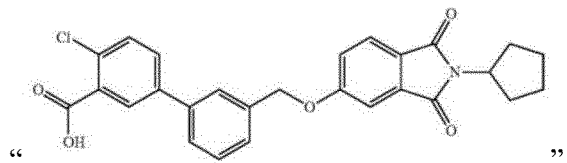"

And replace with:

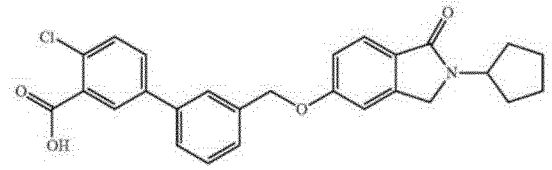

Signed and Sealed this  
Twenty-sixth Day of January, 2021

Drew Hirshfeld  
*Performing the Functions and Duties of the*  
*Under Secretary of Commerce for Intellectual Property and*  
*Director of the United States Patent and Trademark Office*